United States Patent [19]

Carim et al.

[11] Patent Number: 5,755,226
[45] Date of Patent: May 26, 1998

[54] METHOD AND APPARATUS FOR NONINVASIVE PREDICTION OF HEMATOCRIT

[75] Inventors: Hatim M. Carim, West St. Paul; Orlin B. Knudson, Vadnais Heights; Bruce P. Ekholm, Inver Grove Heights; David P. Erickson, Stillwater; William J. Kelliher, Jr., Shoreview; Michael J. Rude, St. Paul, all of Minn.

[73] Assignee: Minnesota Mining and Manufacturing Company, St. Paul, Minn.

[21] Appl. No.: 711,612

[22] Filed: Sep. 10, 1996

Related U.S. Application Data

[62] Division of Ser. No. 189,600, Jan. 31, 1994, Pat. No. 5,553,615.

[51] Int. Cl.$^6$ ........................................... A61B 5/00
[52] U.S. Cl. ...................... 128/633; 128/664; 356/39
[58] Field of Search ......................... 128/633, 664, 128/665, 666; 356/39, 40, 41

[56] References Cited

U.S. PATENT DOCUMENTS

| | | | |
|---|---|---|---|
| 3,923,397 | 12/1975 | Shuck | 356/39 |
| 4,227,814 | 10/1980 | Soodak et al. | 356/410 |
| 4,303,336 | 12/1981 | Cullis | 356/39 |
| 4,407,290 | 10/1983 | Wilber | 128/633 |
| 4,447,150 | 5/1984 | Heinemann | 356/41 |
| 4,548,211 | 10/1985 | Marks | 128/694 |
| 4,562,843 | 1/1986 | Djordjevich et al. | 128/672 |
| 4,586,313 | 5/1986 | Hamaguri | 128/633 |
| 4,621,643 | 11/1986 | New, Jr. et al. | 128/633 |
| 4,653,498 | 3/1987 | New, Jr. et al. | 128/633 |
| 4,685,464 | 8/1987 | Goldberger | 128/633 |
| 4,745,279 | 5/1988 | Karkar et al. | 250/343 |
| 4,776,340 | 10/1988 | Moran et al. | 128/634 |
| 4,805,623 | 2/1989 | Jobsis | 128/633 |
| 4,819,752 | 4/1989 | Zelin | 128/633 |
| 4,832,484 | 5/1989 | Aoyagi et al. | 356/41 |
| 4,869,254 | 9/1989 | Stone et al. | 128/633 |
| 4,883,353 | 11/1989 | Hausman et al. | 356/41 |
| 4,936,679 | 6/1990 | Mersch | 356/41 |
| 4,975,581 | 12/1990 | Robinson et al. | 250/339 |
| 5,078,136 | 1/1992 | Stone et al. | 128/633 |
| 5,101,825 | 4/1992 | Gravestein et al. | 128/633 |
| 5,137,023 | 8/1992 | Mendelson et al. | 128/633 |
| 5,193,543 | 3/1993 | Yelderman | 128/633 |
| 5,200,345 | 4/1993 | Young | 436/63 |
| 5,233,991 | 8/1993 | Wright | 128/653.2 |

(List continued on next page.)

FOREIGN PATENT DOCUMENTS

| | | | |
|---|---|---|---|
| 0 419 223 A2 | 3/1991 | European Pat. Off. | G01N 21/35 |
| 0 476 192 A2 | 3/1992 | European Pat. Off. | G01N 21/35 |
| WO 92/13482 | 8/1992 | WIPO | A61B 5/00 |
| WO 93/13706 | 7/1993 | WIPO | A61B 5/00 |

OTHER PUBLICATIONS

Claim 1 for U.S. Pat. No. 5,456,253, *Biomedical Technology Information Service*, Dec. 1, 1995.

(List continued on next page.)

*Primary Examiner*—Jennifer Bahr
*Assistant Examiner*—Eric F. Winakur
*Attorney, Agent, or Firm*—Gary L. Griswold; Walter N. Kirn; Kari H. Bartingale

[57] ABSTRACT

A method and apparatus for the direct noninvasive prediction of hematocrit in mammalian blood using photoplethysmography techniques and data processing. The method and apparatus also include optional prediction of other analytes of interest: percent oxygen saturation of mammalian blood and methemoglobin of stored blood. The method and apparatus can be used for the immediate, periodic, or continuous noninvasive diagnosis or monitoring of hematocrit levels in mammalian patients without pain to the patient or exposure of the health care practitioner to the blood of the patient.

11 Claims, 32 Drawing Sheets

Microfiche Appendix Included
(2 Microfiche, 128 Pages)

U.S. PATENT DOCUMENTS

| | | | |
|---|---|---|---|
| 5,277,181 | 1/1994 | Mendelson et al. | 128/633 |
| 5,297,548 | 3/1994 | Pologe | 128/633 |
| 5,337,745 | 8/1994 | Benaron | 128/633 |
| 5,355,880 | 10/1994 | Thomas et al. | 128/633 |
| 5,372,136 | 12/1994 | Steuer et al. | 128/633 |
| 5,406,223 | 4/1995 | Vulih et al. | 330/258 |
| 5,553,613 | 9/1996 | Parker | 128/633 |

OTHER PUBLICATIONS

The CRIT–Line™ System Brochure, In–Line Diagnostics Corporation.

Noninvasive Blood Volume Monitoring Brochure, In–Line Diagnostics Corporatiion, 1993.

Cope et al., "A CCD Spectrophotometer to Quantitate the Concentration of Chromophores in Living Tissue Utilising the Absorption Peak of Water at 975 nm", Adv, Exp. Med. Biol., Proc. 150TT88 Cont. Plenum.

Dickensheets et al., Pathlength Independent Spectrophotometric Measurement of Hemoglobin in Solution:, IEEE 11th Annual Conference, pp. 1090–1091 (1989).

Focus, "Near–Infrared Spectrometry in Clinical Analysis", Analytical Chemistry, vol. 58, No. 8, (1986).

Honigs, "Near Infrared Analysis", Analytical Instrumentation, 14(1), pp. 1–62 (1985).

Lee et al., "Measurement of Percent Carboxyhemoglobin with Pulse–Oximetry Technique", IEEE 10th Annual International Conference, pp. 1781–1782 (1988).

Lee et al., "Simultaneous Measurement of Percent Carboxyhemoglobin and Functional Oxygen Saturation", IEEE 11th Annual International Conference, pp. 1092–1093 (1989).

Ozanich, "Non Invasive Method For Determination of Blood pH based on Visible NIR Spectroscopy", University of Washington Ph.D. Dissertation: Chapter 3 Determination of Hematocrit By Short–Wave–Near –Infrared Spectrophotometry and Chapter 4 In–Vivo Spectrophotometry and Imaging of Biological Samples, pp. 1–3, catalogued Feb. 11, 1993.

Pries et al., "Microphotometric Determination of Hematocrit in Small Vessels", American Physiological Society H167–H177 (1983).

Schmitt, "Measurement of blood hematocrit by dual–wavelength near–IR photoplethsmography", SPIE, vol. 1641, pp. 150–161 (1992).

Steinke et al., "Reflectance measurements of hematocrit and oxyhemoglobin saturation", Am J. Physiol. (U.S.), 22(1), pp. H147–H153 (1987).

Steur et al., Evaluation of a noninvasive hematocrit monitor: A new technology, Amer. Clin. Lab., 10(6):20 (1991).

Takatani et al., "Experimental and Clinical Evaluatiion of a Noninvasive Reflectance Pulse Oximeter Sensor", Journal of Clinical Monitoring, vol. 8, No. 4, pp. 257–266 (1992).

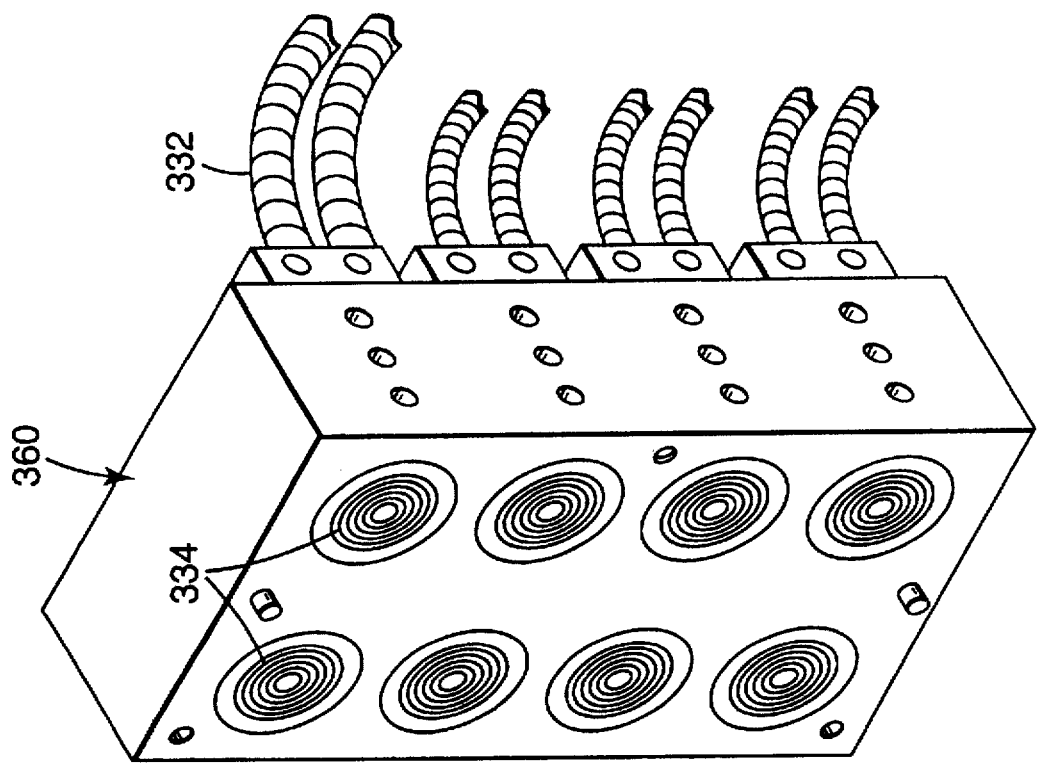
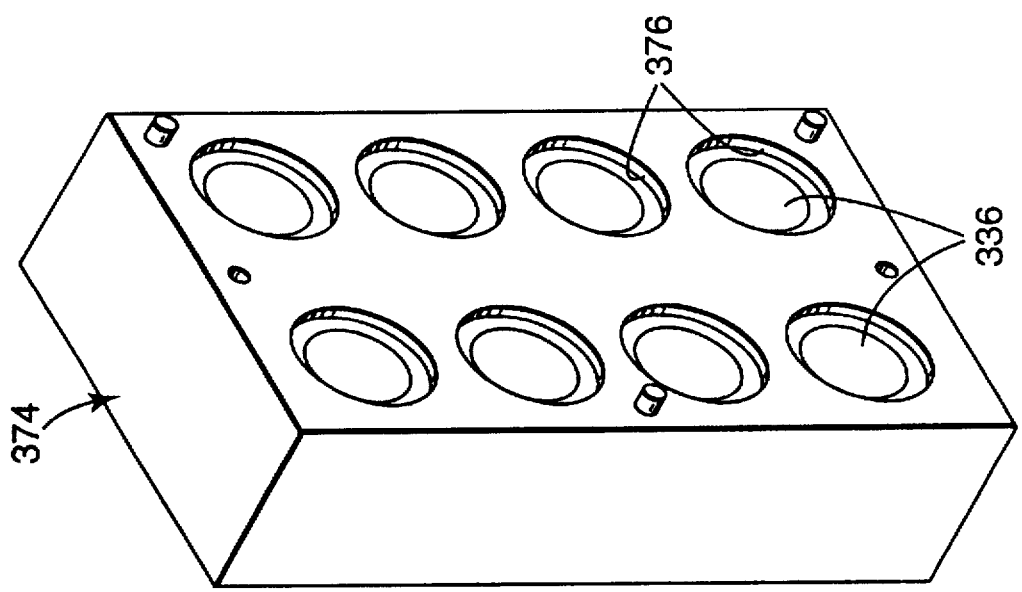

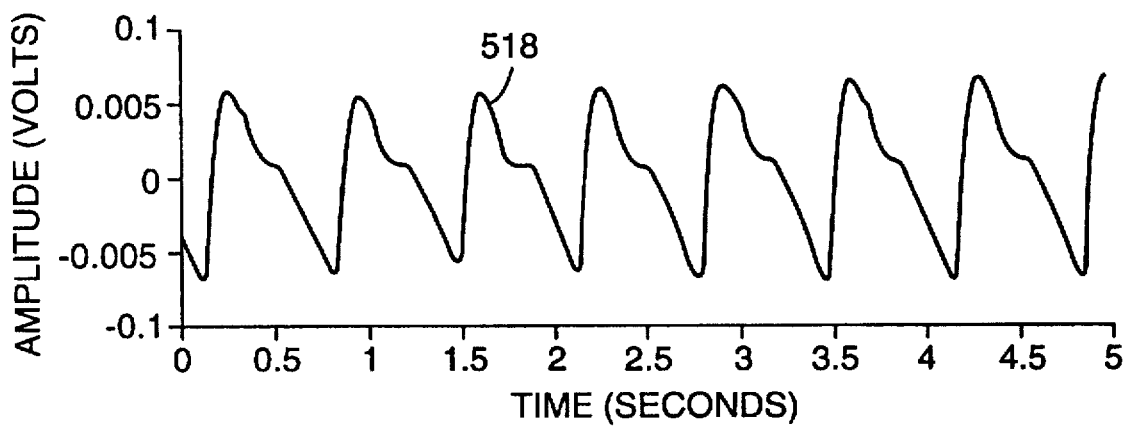
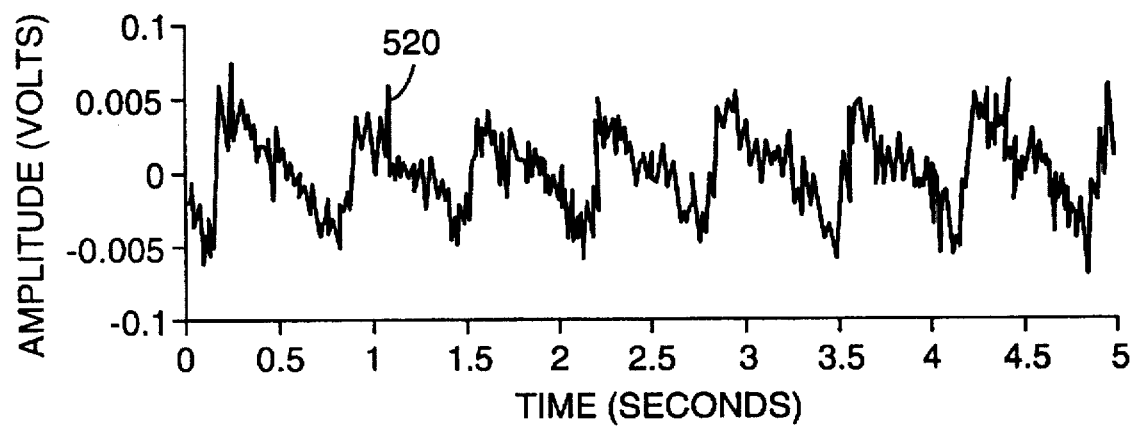
Fig. 21B

METHOD AND APPARATUS FOR NONINVASIVE PREDICTION OF HEMATOCRIT

This is a division of application Ser. No. 08/189,600 filed Jan. 31, 1994 now U.S. Pat. No. 5,553,615.

GOVERNMENT RIGHTS

This invention was made with Government support under Contract N00014-89-C-0024. The Government has certain rights in this invention.

REFERENCE TO MICROFICHE APPENDIX

This application incorporates by reference the computer program listing in the attached microfiche appendix, which includes 2 microfiche and a total of 128 frames.

FIELD OF THE INVENTION

This invention relates to a method and apparatus for noninvasive prediction of hematocrit.

BACKGROUND OF THE INVENTION

Hematocrit, the fractional percent volume of erythrocytes (red blood cells) in total volume of blood, is a vital blood constituent to be monitored to determine the physiological condition of a mammalian patient.

Hematocrit has been traditionally measured by withdrawing or diverting blood from the body of a mammalian patient. Such in vitro or in vivo techniques that are invasive to body cause complications in the condition of the patient and those treating the patient. Any invasive diagnostic or monitoring procedure is less preferred by a mammalian patient than a noninvasive procedure. Blood-borne diseases are a source of concern for those treating the patient.

Invasive procedures for determining hematocrit where a sample of blood is withdrawn are disclosed in U.S. Pat. Nos. 3,923,397 (Shuck) and 5,200,345 (Young) and in European Patent Publication 0 419 222 A2 (Callis et al.)

Invasive procedures for determining hematocrit where a sample of blood is diverted from the bloodstream of a patient are disclosed in U.S. Pat. Nos. 4,227,814 (Soodak et al.); 4,303,336 (Cullis); and 4,447,150 (Heinemann); and in European Patent Publication 0 419 223 A2 (Callis et al.).

Invasive procedures for determining hematocrit where a probe is inserted into the body is disclosed in U.S. Pat. Nos. 4,776,340 (Moran et al.) and 4,936,679 (Mersch).

Noninvasive procedures for predicting hematocrit can employ magnetic resonance, as disclosed in U.S. Pat. No. 5,233,991 (Wright); or impedance plethysmography, as disclosed in U.S. Pat. Nos. 4,562,843 (Djordjevich et al.) and U.S. Pat. No. 4,548,211 (Marks).

Noninvasive procedures for predicting percent oxygen saturation employing photoplethysmography, commonly called pulse oximetry, are disclosed in U.S. Pat. Nos. 4,819,752 (Zelin) and 5,193,543 (Yelderman). In Zelin, light emitting diodes at two different wavelengths are employed, with corrections made for the pulsatile nature of blood flow, variations in the strength of the light source, variations in the thickness of tissue through which the light passes, variations in placement of the detector in respect of the location of the light emitters, and changes in the physiology of the nonpulsatile component. In Yelderman, light emitting diodes at two different wavelengths are also employed, with corrections made to improve resistance to interference from ambient artificial light, BOVIE electrocautery interference using AM modulation/demodulation techniques.

Noninvasive procedures for predicting hemoglobin, arterial oxygen content and hematocrit employing photoplethysmography is disclosed in U.S. Pat. No. 5,101,825 (Gravenstein et al.). In Gravenstein et al., the blood constituents are predicted by measuring the change in the mass of hemoglobin resulting from a measured change in the volume of blood. After total hemoglobin is predicted, hematocrit is approximated by multiplying total hemoglobin by a factor of three.

None of the known invasive procedures are preferable to either patient or practitioner if a truly noninvasive technique were available that could predict hematocrit accurately. None of the known noninvasive procedures predict hematocrit directly.

European Patent Publications 0 419 222 A2; 0 419 223 A2 (both Callis et al.); and 0 476 192 A2 (Callis) disclose methods for prediction of hematocrit using chemometric techniques and regression analysis that uses the spectral absorbance of water in the near infrared spectrum to provide the basis of prediction based on a two compartment model where one compartment has a different amount of water than the other compartment. But none of the Publications disclose a method or apparatus to noninvasively predict hematocrit.

SUMMARY OF THE INVENTION

The treatment of patients needs a method and apparatus to predict hematocrit using photoplethysmography rapidly, directly, accurately, and mechanically noninvasively.

The present invention provides a method and apparatus for the mechanically noninvasive, rapid, direct and accurate prediction of hematocrit using photoplethysmography.

In one aspect of the invention, the method and apparatus also predicts oxygen saturation using photoplethysmography.

In another aspect of the invention, the method and apparatus also predicts methemoglobin using photoplethysmography.

In another aspect of the invention, the method and apparatus predict hematocrit and optionally oxygen saturation transcutaneously of a mammalian patient using algorithms that employ a plurality of wavelength ratio pairs.

In another aspect of the invention, the method and apparatus predict hematocrit and optionally methemoglobin noninvasively in blood stored in containers for later transfusion into a mammalian patient.

In another aspect of the invention, the method and apparatus provide corrections for oxygen saturation status in hematocrit to correct for variations in the amount of carboxyhemoglobin in the blood of a mammalian patient.

In another aspect of the invention, the apparatus provides a method for minimizing an undesirable effect of light causing an excessive change in the temperature in tissue being analyzed transcutaneously.

In another aspect of the invention, the apparatus provides a method for minimizing the effect of extraneous light interrogating mammalian tissue.

In another aspect of the invention, the apparatus provides a combination of fiber optics and lenses that maximize the shape and transmission of light emerging from interrogated mammalian tissue.

In another aspect of the invention, the apparatus optionally provides an order-adaptive filter for detrending photoplethysmographic signals.

In another aspect of the invention, the apparatus provides an adaptive peak and valley detector for waveforms generated in photoplethysmography.

In another aspect of the invention, the apparatus provides a high common mode rejection amplifier for use with photoplethysmographic signals.

In another aspect of the invention, the method and apparatus provide a method for estimating the confidence level of noninvasive photoplethysmographic signals.

In another aspect of the invention, the method and apparatus optionally provide quantifiable performance indices for photoplethysmographic waveforms.

In another aspect of the invention, the method and apparatus optionally provide a noise reduction technique for multi-wavelength photoplethysmography.

A feature of the invention is the ability to noninvasively predict hematocrit within plus or minus 5 hematocrit percent of the actual hematocrit value.

Another feature of the invention is the ability to noninvasively predict percent oxygen saturation within plus or minus 5 oxygen saturation percent of the actual oxygen saturation value.

An advantage of the invention is that the noninvasive prediction of hematocrit can proceed intermittently or continuously without disruption to the blood flow or blood stream of a mammalian patient.

Another advantage of the invention is that the noninvasive hematocrit prediction minimizes exposure of a health care practitioner to blood of the mammalian patient.

Another advantage of the invention is that the noninvasive hematocrit prediction can be made rapidly and accurately in intensive treatment environments, such as hospital emergency rooms, intensive care and surgical arenas, and in military triage.

Another advantage of the invention is that a simultaneous prediction of oxygen saturation and hematocrit can be made, thereby allowing the correction of one to allow for the effect of varying magnitudes of the other.

Another advantage of the invention is that the method and apparatus of the invention is adaptable to be miniaturized for portable use where health care is needed but facilities are unavailable.

Yet another advantage of the invention is that it allows the use of predicted quantities of hematocrit and percent oxygen saturation to calculate other meaningful predictions, such as the oxygen carrying capacity of mammalian blood, defined as the product of hematocrit and percent oxygen saturation assuming a normal amount of hemoglobin present in a red blood cell.

Other aspects, features, and advantages will become apparent as a description of embodiments proceeds with reference to the following drawings.

BRIEF DESCRIPTION OF THE DRAWINGS

FIGS. 8A and 8B are illustrations of two plattens used in an embodiment of the present invention.

FIGS. 21A–21D show exemplary waveforms associated with the template matching technique of the present invention.

EMBODIMENTS OF THE INVENTION

Photolethysmography

Figure 1:
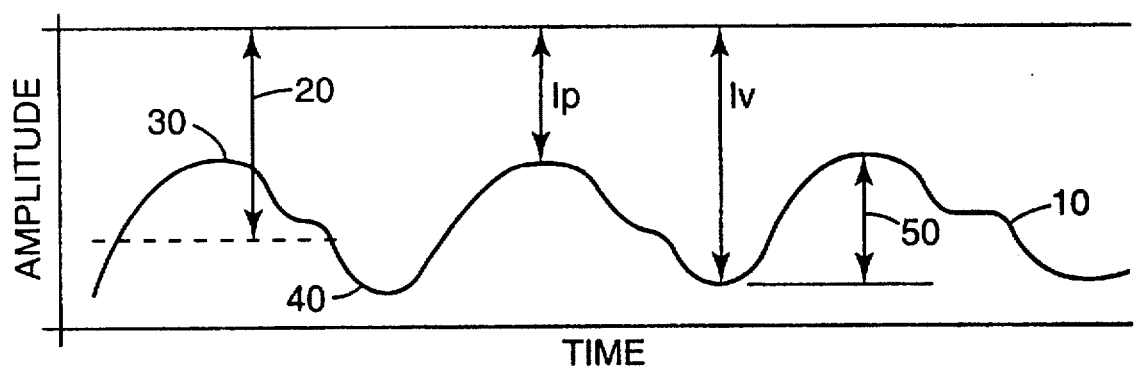
FIG. 1 is a typical photoplethysmograph.

In photoplethysmography, visible and near infrared (NIR) light is transmitted through mammalian blood to predict hematocrit and other analytes of interest in such blood. The transmission is noninvasive without diversion of the blood from the vessels in which the blood is contained.

In the embodiment of transcutaneous photoplethysmography, one must account or discount for a number of factors that are not encountered in the use of photoplethysmography in an in vitro or diverting in vivo environment used in the prior art. Nonlimiting factors one must consider are: oxygen saturation; the absorbance characteristics of mammalian tissue, mammalian bone, venous blood, and the capillary bed; the distance of light transmission; the avoidance of ambient light; the pigmentation of skin; blood pressure; and tissue temperature and compression.

In the embodiment of assessing the quality of mammalian blood stored for later transfusion, one must consider a number of factors that are not encountered in the use of photoplethysmography in noninvasive, transcutaneous embodiments. Nonlimiting factors one must consider are: size of the vessel; distance of light transmission; the absorbance characteristics of the containing vessel; temperature of blood; and substances added to blood to preserve blood acting as interferents.

Once the transmitted light is detected, one must consider the effects of noise; the effects of ambient light; and the effects of the settling rate of particulates and cells (i.e., scatterers of light).

Once the transmitted light is treated to maximize its usefulness in hematocrit prediction, then the prediction must be sufficiently accurate and precise to be useful as a substitute for invasive or diverting procedures. Nonlimiting factors one must consider are the robustness of the calibration equation, the inclusiveness of a broad representation of the general population when forming the training set; and a reliable reference method that also is accurate and precise.

The present invention has overcome these factors to provide a method and apparatus to noninvasively and directly predict hematocrit using photoplethysmography.

The Beer-Lambert law relates the light intensity exiting an optical absorber Io, to the light intensity incident on it, Ii, according to the following equation:

$$Io=Ii(e^{-k*l*c})$$

where k is the extinction coefficient of the absorber, l is the pathlength traversed by the light through the absorber and c is its molar concentration.

Optical absorbance A is therefore defined as:

$$A=ln(Ii/Io)=k*l*c$$

where ln is the natural logarithm. In traditional spectroscopy instruments the intensity Io represents the intensity of light that has gone through the sample (absorber) holder such as a cuvette and the absorber itself; and therefore a reference absorbance of the empty cuvette is taken prior to filling it up with the absorber and subsequently subtracted. In other instruments, two beams of light are used, with one going through an empty cuvette and the other through a cuvette filled with the absorber but otherwise identical to the first cuvette. The difference of absorption values then gives the true absorption of the absorber under test. In other words one needs to measure the intensity of light with and without the presence of the absorber in the path of the light.

In this invention, as is required in the field of pulse oximetry (c.f., U.S. Pat. Nos. 4,653,498; 4,621,643; and 4,685,464; among others) the light intensities Io and Ii as defined above are obtained from a well-vascularized body part such as a finger by measuring the light emerging from the finger at the points in time identified above in the photoplethysmograph as the "peak" and "valley" respectively.

It must be emphasized that any measurement of light attenuated by tissue in vivo is the result of the incident light being reflected, absorbed and significantly scattered. This last phenomenon, especially as it is spatially co-mingled with absorption inside the absorber has the multiple effects of:

(1) increasing the path length of photons relative to the geometric distance between the source and detector in contact with the finger;

(2) as a consequence of (1) above the optical absorption cross section is increased (i.e., the photons are bounced around inside the absorber increasing chances of being absorbed in it); and (3) the collimated or directional beam of incident light emerges from the finger as from a diffuse source.

Particularly, this scattering is also a function of the wavelength, and therefore the measurement of absorption at a given wavelength needs to be normalized by another wavelength to neutralize the effect of scattering. "Attenuated light" means the light emerging from mammalian tissue in a form diminished from irradiated light by the effects of reflection, refraction, absorbance, and scattering.

FIG. 1 shows a typical photoplethysmograph plotted in amplitude vs. time. Typical photoplethysmographs can be comprised of a desired pulsatile signal 10, a Direct Current (DC) average 20, various noise and other physiological and mechanical artifacts. Nonlimiting examples of these artifacts are physical movement between the sensor and interrogated mammalian tissue, respiratory-induced variations, and other artifacts. Repetitively within the pulsatile signal 10 are locations of peaks 30 and valleys 40, and their corresponding amplitudes or intensities $I_P$ and $I_V$, respectively. Pulsatile average 50 is the average AC value $(I_P-I_V)$ over a defined number of pulse periods.

While it is possible to visually evaluate the quality of a desired signal embedded in artifact and noise, such as using a digital oscilloscope, the process requires a repetitive application of an empirically derived and applied standard.

The present invention provides a repeatable, quantifiable method of prediction that evaluates the waveform for peaks, valleys, DC averages, and pulsatile averages. The method of prediction is predicated on proper selection of wavelengths related to the analytes of interest.

Selection of Appropriate Wavelengths

European Patent Publication 0 419 223 A2, corresponding to U.S. patent application Ser. No. 07/995,951 (Callis et al.), the disclosures of which are incorporated by reference, discusses both ratios of wavelength pairs and taking a multiple derivative of the relationship between the absorption as a function of the wavelength as alternative pre-processing techniques useful for the prediction of hematocrit. In both methods, wavelengths chosen are associated with absorbance peaks of water in blood where the two compartments of blood have differing amounts of water. In the ratio method, a second wavelength chosen preferably corresponds to an isosbestic point for absorbance of oxyhemoglobin and deoxyhemoglobin. A second ratio for correction of oxygen saturation is optionally included.

This invention unexpectedly requires additional and different ratios for noninvasive, transcutaneous prediction of hematocrit. Irradiation and detection of transcutaneously transmitted light is exceedingly more complex than such irradiation and detection in a stationary cuvette or a noninvasive but diverting blood flow loop with a viewing space of constant dimensions.

As in European Patent Publication 0 419 223 A2, corresponding to U.S. patent application Ser. No. 07/995,951 (Callis et al.), the selection of wavelengths for direct, noninvasive prediction of hematocrit is based on the components of water, oxyhemoglobin, and deoxyhemoglobin in mammalian blood.

But unexpectedly, the selection of wavelengths employs multiple wavelengths having significance for those components and their interrelationships. Depending on the mammalian species involved, the scope of the invention is not limited to a particular number of wavelengths employed. Desirably, from about 4 to about 14 wavelengths can be initially selected for statistical analysis to determine the best coefficients for prediction of hematocrit. Preferably between 5 and 8 wavelengths can be initially selected and used in statistical analysis for determining the best coefficients for prediction of hematocrit.

At a minimum, selection of wavelengths should include:

(1) a wavelength where the absorbance of water is at or near a measurable peak;

(2) at least one wavelength where the absorbance of oxyhemoglobin (oxyHb) and deoxyhemoglobin (deoxyHb) are predictable and represent total hemoglobin (Hb) content, i.e., the isosbestic region of hemoglobin (Hb Isos), it being preferred to use two wavelengths from this region;

(3) a wavelength where the absorbance of water greatly exceeds the absorbance of all forms of hemoglobin; and (4) a wavelength where the absorbance of all forms of hemoglobin greatly exceeds the absorbance of water.

One wavelength can satisfy two or more of the selection criteria. In European Patent Publication 0 419 223 A2, two wavelengths satisfied all four selection criteria.

Desirably, selection of wavelengths also includes:

(5) a wavelength where the absorbance of oxyhemoglobin greatly exceeds the absorbance of deoxyhemoglobin; and (6) a wavelength where the absorbance of deoxyhemoglobin greatly exceeds the absorbance of oxyhemoglobin. Again one wavelength in the set can satisfy two or more of the selection criteria. A ratio of the two selection criteria (5) and (6) is conventionally used for pulse oximetry. Unexpectedly, use of selection criteria (5) and (6) can correct for the effects of the presence of differing amounts of carboxyhemoglobin in mammalian blood as result of whether the patient smokes tobacco products or has inhaled smoke.

Preferably, the selection of wavelengths also includes:

(7) at least one different wavelength from selection criteria (1) where the absorbance of water is at or near a measurable peak or shoulder and is subjected to differing interferences than selection criteria (1); optionally (8) a wavelength where the absorbance of water is in or near a valley between peaks.

Optionally the selection of wavelengths can also include (9) a wavelength where water and hemoglobin are in an isosbestic relationship.

As stated above, optical absorbance is a natural logarithmic relationship. Discussion of the selection of wavelengths herein refer to absorbance intensity of ln(Io/Ii) or ln(Ii/Io) or other relationships between the analogues of Ii and Io, i.e., Iv and Ip, respectively, that may additionally involve $I_{DC}$ described below as forms of H Values described below.

Use of these selection criteria does not mean that the wavelength will be used in the ultimate prediction equation. Statistical analysis described below may be used to choose ratios among these selection criteria wavelengths to determine the best correlation.

Based on the required, desirable, and preferred selection criteria, Table 1 shows ranges and preferred wavelengths for use in the present invention.

TABLE 1

| Wavelength Criteria | Acceptable Range (nm) | Desirable Range (nm) | Preferred Range (nm) |
|---|---|---|---|
| 1. Water Peak | 1160–1230 | 1180–1215 | 1195–1207 |
| 2. Hb Isos | 800–850 | 800–840 | 805–837 |
| 3. Water >> Hb | 1150–2100 | 1290–1500 | 1300–1315 |
| 4. Hb >> Water | 450–690 | 600–685 | 630–680 |
| 5. Deoxy Hb >> Oxy Hb | 650–690 | 655–685 | 660–680 |
| 6. Oxy Hb >> Deoxy Hb | 890–920 | 895–925 | 900–910 |
| 7. Other Water Peak(s) | 960–990 | 970–990 | 972–985 |
| 8. Water Valley | 1100–1120 | 1105–1115 | 1110 |
| 9. Water & Hb Isos | 1130–1170 | 1140–1165 | 1160 |

For each of the pulses in an optical train at each wavelength selected, the apparatus picks out the numerical values at the locations of the photoplethysmograph peak, valley and the average value which represents the DC component. This is done for the simultaneously recorded pulse at each of the several wavelengths used.

Selection of "H Value" Equations

Because of the scattering encountered in the mammalian tissue, it is a discovery of the present invention that only a pseudo-absorption can be calculated by the natural logarithmic ratio of the light intensities Io and Ii.

For purposes of this invention, this pseudo-absorption is termed the "H Value" or "HV". In European Patent Publication 0 419 223 A2, where one ratio of two wavelengths is disclosed to predict hematocrit and one ratio of two other wavelengths is disclosed to optionally correct the hematocrit for oxygen saturation, a ratio of ln(Io/Ii)@ wavelength 1 divided by the ln(Io/Ii)@ wavelength 2 is used. But the effects of pulsatile flow in mammalian tissue were not considered in the static or dynamic conditions disclosed.

It is understood that ratios can be calculated by using ln(Io/Ii) or ln(Ii/Io). It is further understood that the H Values can be calculated by interchanging the numerator and denominator, each identified as ln(Io/Ii), or by forming other non-logarithmic and linear and nonlinear ratios as shown below.

Unexpectedly, the present invention has selected four H Values that approximate the effects of pulsatile blood flow in mammalian tissue. Depending on the mammalian species involved and the area of the patient being interrogated, any of these H Values could provide an acceptable result. But an H Value that takes into consideration pulsatile nature of the mammalian tissue during light interrogation and the effect of the DC component is preferred over an H Value that does not.

The four H Values equations useful in the present invention are shown below as equations. Moreover, the present invention contemplates that other H Values can be calculated empirically according to techniques known to those skilled in the art of waveform processing.

$$HV1 = \ln(Ip/Iv)@w1 / \ln(Ip/Iv)@w2$$
$$HV2 = \{\ln(Ip/Iv)@w1/\ln(Ip/Iv)@w2\}*\{Idc@w2/Idc@w1\}$$
$$= HV1*\{Idc@w2/Idc@w1\}.$$
$$HV3 = \{(Ip-Iv)@w1/(Ip-Iv)@w2\}*\{Idc\ @w2/Idc@w1\}.$$
$$HV4 = \ln\{(Ip-Iv)/Idc\}@w1/\ln\{(Ip-Iv)/Idc\}@w2$$

where Idc is the DC or average value of the light intensity for a pulse, w1 and w2 are two independent wavelengths, Ip is intensity at a peak, Iv is intensity at a valley, and the subscripts 1 to 4 for the H values HV are identifiers but do not indicate any ascribed wavelength. The difference between Ip and Iv is a single pulse peak to peak intensity; the average of several of these is the pulsatile average (AC).

HV1 is a ratio for two different wavelengths of a logarithmic relation between peak and valley of a pulse.

HV2 multiplies HV1 by an inverse ratio of the average DC value at the two wavelengths to normalize the AC component of the signal.

HV3 multiplies a ratio of the single pulse peak to peak intensity at two wavelengths by the same inverse ratio as used in HV2; an AC/DC ratio. The differences between HV2 and HV3 is the absence of any logarithmic relationship in HV3.

HV4 is a ratio for two different-wavelengths of the natural logarithm of the single pulse peak to peak intensity over DC average; a logarithmic AC/DC ratio.

Thus, for purposes of this invention, the term $HV3_{2,7}$ indicates a pseudo-absorbance calculated according to the formula for HV3 shown above with the two wavelengths w1 and w2 being identified as wavelengths 2 and 7, respectively.

Such pseudo-absorbance values are obtained from a broad cross-section of mammalian patients of the same species and preferably stored electronically. A look-up table can be prepared according to the teaching of European Patent Publication 0 419 223 A2 and patent application Ser. No. 07/995,951 identified above in conjunction with statistical analysis as described below.

As identified in European Patent Publication 0 419 223 A2 and patent application Ser. No. 07/995,951 identified above, the use of second derivative absorbance values at wavelengths in the regions of interest can be used and substituted for H Values to derive a multi-parameter regression equation for hematocrit prediction. A larger number of measurements is required. But the method of obtaining the pseudo-absorbance values of hematocrit is derived from pulsatile flow as treated according to the present invention.

Selection of Statistical Analysis

Generally, one of the four HV formulae, i.e., HV1 or HV2 or HV3 or HV4 is chosen for the purpose of approximating the absorption equation coefficients with the best correlation coefficient and standard error of prediction possible.

Statistical analysis can take several mathematical forms known to those skilled in the art. Nonlimiting examples include linear regression, non-linear regression, multiple linear regression, step-wise linear regression, partial least squares, principal component analysis, chemometrics, and other regression techniques as well as curve-fitting, neural networks, and other non-regression techniques.

For example, linear regression can be employed as disclosed in European Patent Publication 0 419 223 A2. If H Value, HV3, is chosen, then all possible wavelength pairs xy are chosen to form numerous HV3 values of the form $HV3_{x,y}$.

As disclosed in European Patent Publication 0 419 223 A2, one can calculate all possible wavelength pairs of a spectrum. But using the wavelength selection criteria of the present invention, one can confine the wavelength pairs only to those wavelengths actually selected for formation of the prediction equation.

This reduction in the number of wavelength pairs selected reduces the complexity of the light transmission and optics apparatus to require only those wavelengths actually used for statistical analysis of the H Value chosen.

For example, if photoplethysmographs were recorded at four wavelengths simultaneously, then the following HV3 values would be computed $HV3_{1,2}$; $HV3_{1,3}$; $HV3_{1,4}$; $HV3_{2,3}$; $HV3_{2,4}$ and $HV3_{3,4}$. Each of these H Values is computed for a large number of individual pulse pairs (recorded substantially simultaneously), generally 40, for a given patient, and the average is used as part of the equation to predict hematocrit. A smaller number of pulse pairs can be used if the variance from pulse to pulse is acceptably small. The aggregate of the H Values recorded establish a training set of H Values.

The average values of the H Values of each of the possible wavelengths of interest can be treated as variables for statistical analysis. The data can be analyzed using a personal computer, such as an IBM personal computer, utilizing commercially available computer software, such as the statistical computer software SAS/STAT (R) , Version 6, Fourth Edition sold by SAS Institute Inc., Cary N.C. 27512.

Data can be analyzed using various techniques including Forward Selection, Stepwise Regression, and Maximum $R^2$ Procedure. The latter two are preferred.

Ordinarily the FORWARD SELECTION (FS) technique begins with no variables in the mathematical model used to form the prediction equation. For each of the independent variables, FS calculates F statistics that reflect the variables' contribution to the model if it is included. The p-values for these F-statistics are compared to the significance level defined for entry into the model, "SLENTRY=" value that is specified in the Model statement. If no F statistic has a significance level less than the SLENTRY=value, FS stops. Otherwise, FS adds the variable that has the largest F statistic to the model. FS then calculates F statistics again for the variables still remaining outside the model, and the evaluation process is repeated. Thus variables are added one by one to the model until no remaining variable produces a significant F statistic. Once a variable is in the model it stays.

The STEPWISE REGRESSION method is a modification of the FS technique and differs in that variables already in the model do not necessarily stay there. As in the FS method, variables are added one by one to the model, and the F statistic for a variable to be added must be significant at the SLENTRY=level. After a variable is added, however, the SR method looks at all the variables already included in the model and deletes any variable that does not produce an F statistic significantly lower than the chosen significance level for staying in the model. Only after this check is made and the necessary deletions accomplished can another variable be added to the model. The SR process ends when none of the variables outside the model has an F statistic significant at the entry significance level and every variable in the model is significant at the staying significance level, or when the variable to be added to the model is the one just deleted from it.

The Maximum $R^2$ (MAXR) improvement technique does not settle on a single model. Instead it tries to find the best one variable model, the best two variable model, and so forth, although it is not guaranteed to find the model with the largest $R^2$ for each size. $R^2$ or R sqd. refers to the square of the correlation coefficient R.

The MAXR method begins by finding the one variable model producing the highest $R^2$. Then another variable, the one that yields the greatest increase in the $R^2$, is added. Once the two variable model is obtained, each of the variables in the model is compared to each variable not in the model. For each comparison, MAXR determines if removing one variable and replacing it with the other variable increases $R^2$. After comparing all possible switches, MAXR makes the switch that produces the largest increase in $R^2$. Comparisons begin again, and the process continues until MAXR finds that no switch could increase $R^2$. Thus, the two variable model achieved is considered the "best" two variable model the technique can find. Another variable is then added to the model, and the comparing-and-switching process is repeated to find the best three variable model, and so forth.

The difference between the Stepwise method and the MAXR method is that all switches are evaluated before any switch is made in the MAXR procedure. In the Stepwise method, the 'worst' variable can be removed without considering what adding the 'best' remaining variable might accomplish.

Selection of Prediction Equations

Using a statistical analysis described above on one or more H Value equations described above that employ wavelengths chosen according to the Selection Criteria described above, an equation for the prediction of hematocrit can be obtained.

When using MAXR or stepwise analysis to find the best correlation coefficients and $R^2$ value, the prediction equation can have a linear or nonlinear combination of n regression coefficients for n variables constituting the H Values at the pairs of wavelengths selected from the wavelength selection criteria. These regression coefficients are stored in a look-up table on the computer and are combined with the realtime photoplethysmograph to predict hematocrit.

Thus, an hematocrit prediction equation can be a plurality of ratios linearly or nonlinearly combined depending on the best correlation using statistical analysis to actually measured hematocrits for the same patients. Actual values of hematocrit are measured and stored according to a standard, accepted technique. Nonlimiting examples of such measurement techniques include cell counters, centrifuges, and indirectly from the amount of total hemoglobin measured on a co-oximeter.

Broadly, a prediction equation according to the present invention is represented by:

$$HCT = \alpha (HV_{a,b})^A + \ldots \omega (HV_{x,y})^Z + \phi$$

where HV is the H Value for wavelengths pairs a,b to x,y selected by the statistical analysis according to the step (e); A through Z are exponents of any value; $\alpha$ through $\omega$ are regression coefficients determined by the statistical analysis; and $\phi$ is the intercept also determined by the statistical analysis.

For example, the following equation shows an exemplary prediction equation according to the present invention:

$$HCT = \alpha HV2_{1,4} + \beta HV2_{2,3} + \chi HV2_{2,7} + \delta HV2_{3,7} + \epsilon HV2_{4,6} + \phi$$

where HV2 is the H Value described above for various wavelengths selected 1, 2, 3, 4, 6, and 7; $\alpha, \beta, \chi, \delta$, and $\epsilon$ are regression coefficients determined by statistical analysis; and $\phi$ is the intercept also determined by statistical analysis. $\alpha, \beta, \chi, \delta, \epsilon$, and $\phi$ can be positive or negative.

Depending on the mammalian species involved and the location of noninvasive hematocrit prediction transcutaneously, it is possible that one or more wavelengths selected for formation of a prediction equation are not in the ultimate prediction equation. That fact does not diminish the need for use of the wavelength selection criteria described above. From the presentation of wavelengths shown above, it is possible in the present invention to employ a wavelength, i.e., wavelength 5 or wavelength 8, that is not ultimately used in the prediction equation.

Once a prediction equation is established, it is validated. The accuracy in formation and performance is reviewed to assure reproducibility. European Patent Publication 0 419 223 A2 discloses the techniques for calculating standard error of calibration and standard error of prediction, also known as standard error of estimate.

It is desired to have a standard error of estimate of less than about 5% hematocrit and preferably less than about 2.5% hematocrit.

Use of A Prediction Equation

With the equation established and standard error of estimate confirmed to be acceptable, then the equation can be used to predict unknown hematocrit values noninvasively. Preferably an equation is stored electronically with the established regression coefficients from the training set and the specific wavelengths are irradiated and detected and analyzed according to the H Value(s) in the prediction equation.

Having provided a description of the establishment and rationale for a direct hematocrit prediction equation, an overview of the apparatus and method to achieve and use that equation follows.

System Overview

Figure 2:
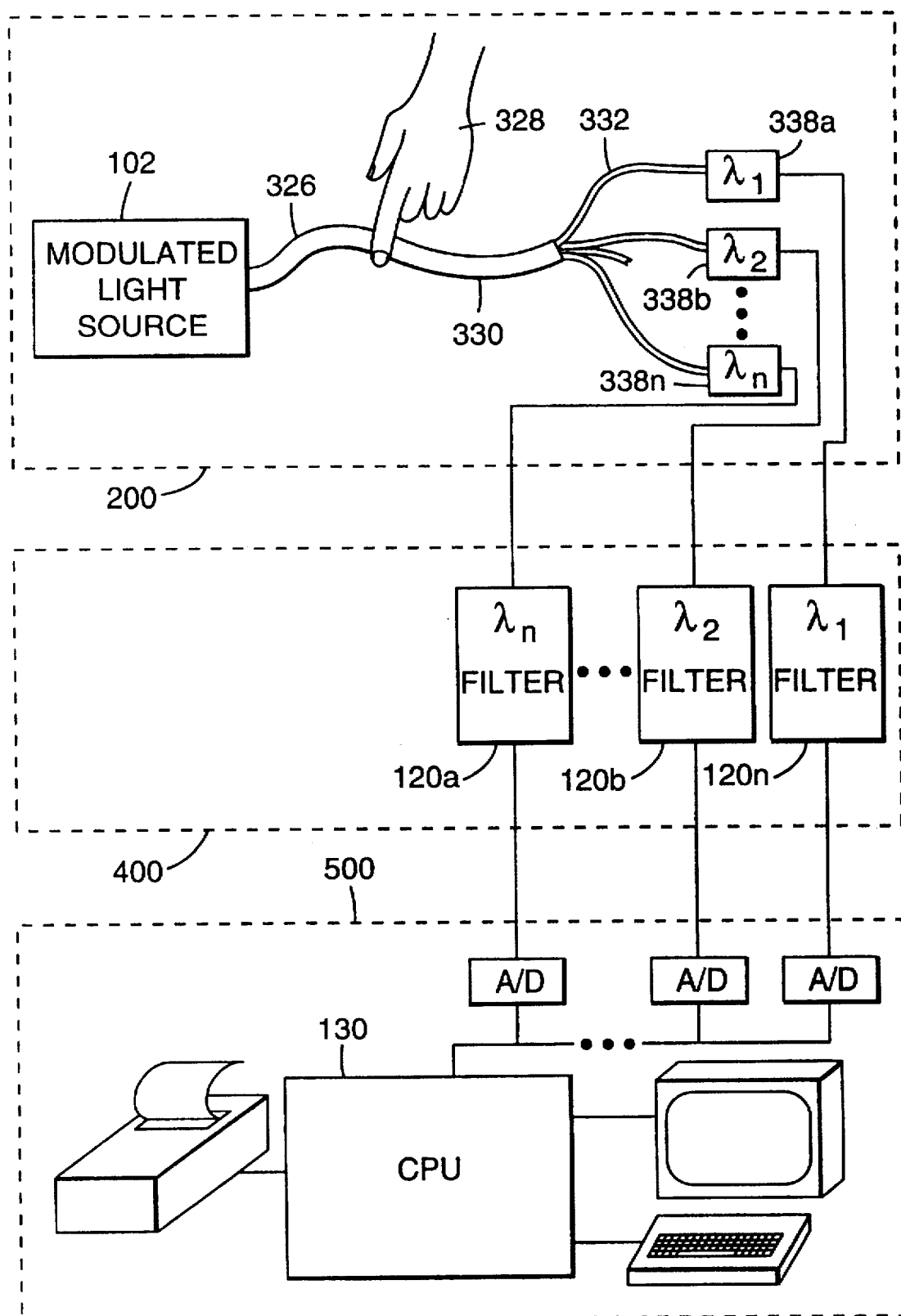
FIG. 2 is a simplified schematic illustration of a system of the present invention.

FIG. 2 shows a simplified block diagram of the present system 100 for noninvasive determination of hematocrit. System 100 includes an optics module 200, an electronics module 400 and a processing module 500. As described above, the present system measures hematocrit noninvasively by measuring absorbance of light through blood perfused tissue at appropriate wavelengths. The amount of light absorbed at each wavelength of interest is used to determine a correlation between the amount of light absorbed and the hematocrit level.

The present invention samples the blood perfused tissue at a predetermined rate. The minimum frequency at which the tissue is sampled must satisfy the Nyquist sampling criteria of at least twice the highest frequency present in the signal to be sampled. For purposes of the present invention, the signal of interest is the pulsatile blood flow through the mammalian tissue. This signal contains frequencies such as the pulse rate (1-2 Hz in humans) and other higher frequency components such as those present in the dichrotic notch. A preferred sampling frequency of 100 Hz was therefor chosen for purposes of the present invention to ensure capture of all relevant plethysmographic information.

A mammalian sample 328, such as a human finger, is interrogated by a modulated light source 102, which is controlled as described below with respect to FIG. 4. The light is modulated at the preferred sampling frequency of 100 Hz. The modulated light travels down fiber bundle 326 and is transmitted through the sample 328. The transmitted light is collected by a plurality of photodetectors 338, each of which corresponds to a different one of the wavelengths of interest.

The optical radiation collected by each photodetector is converted into a photocurrent by the electronics module 400. Each photocurrent is filtered and amplified by one of a plurality of amplifier/filter electronics 120, one for each wavelength of interest. The amplified and filtered signals are then digitized, stored and processed by processing module 500 as described in more detail below.

Method Overview

Figure 3:
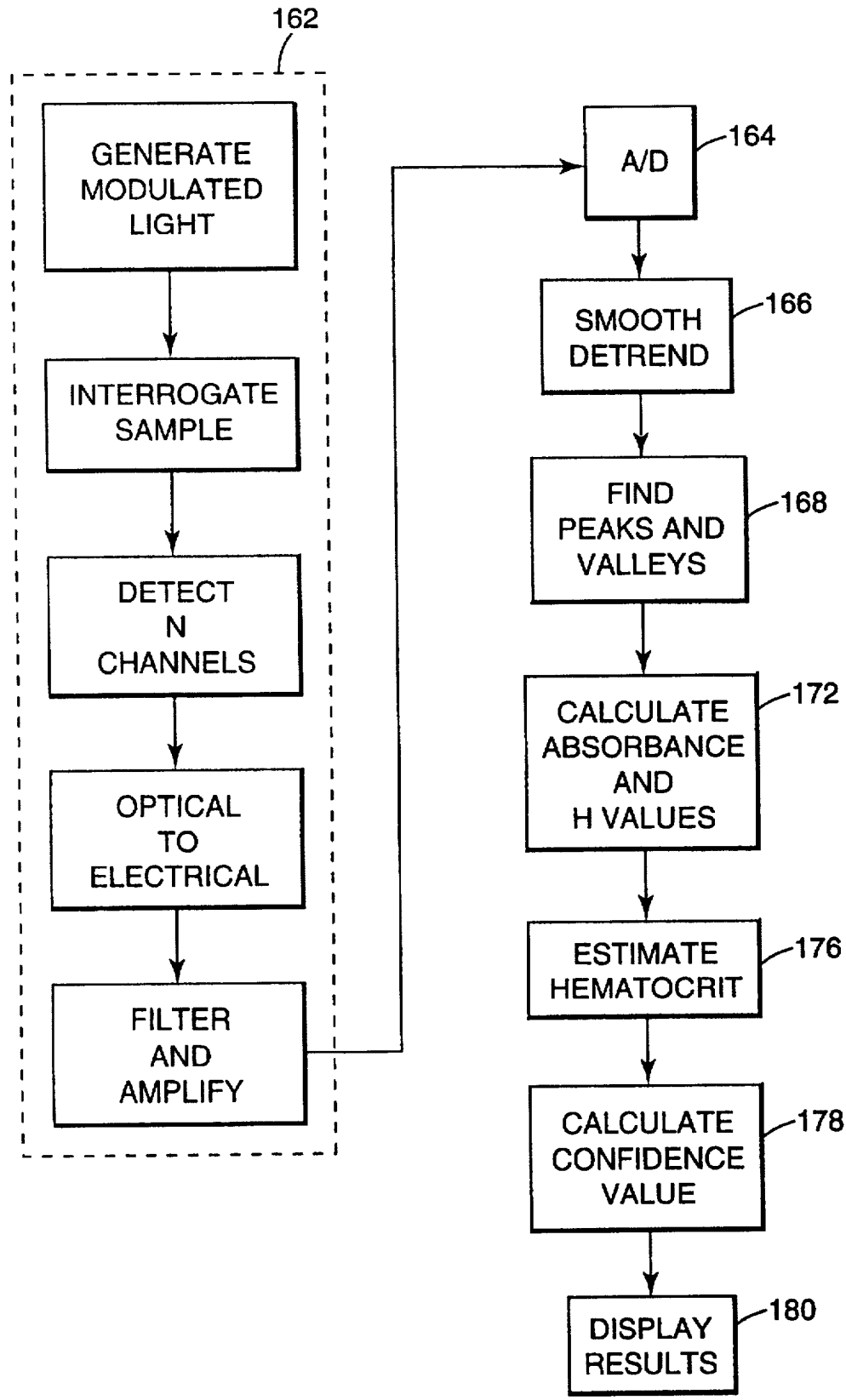
FIG. 3 is a simplified diagram of the method of the present invention.

FIG. 3 shows a simplified block diagram of the control flow through the system of FIG. 2. The preprocessing control 162 steps are performed as described above by optics module 200 and electronics module 400. The post-capture processing steps 164–180 are performed on the digitized photoplethysmographic signals by the processing module 500 to determine and extract the desired information. The sampled signals may be smoothed and/or detrended in control block 166 to remove undesirable low frequency components, such as DC drift, which may be induced into the photoplethysmographic signals due to artifacts such as respiration and movement of the subject. The location and magnitude of the peaks and valleys of the photoplethysmographic signals for each wavelength of interest are determined in control block 168.

Absorbances for each wavelength of interest are calculated in control block 172, as well as absorbance ratios of different wavelength pairs to form the H Values described herein. The H Values are then combined in control block 176 as described herein to predict the hematocrit.

Once the hematocrit is predicted, a measure of the level of confidence of the estimate is determined at control block 178. This is important in establishing confidence limits a clinician may have in the hematocrit estimate, and may indicate whether further tests or measurements need to be made. The waveforms, hematocrit, confidence value, oxygen saturation and other information determined by the present system are displayed as required at control block 180.

Having provided system and method overviews of the invention, a specific embodiment of the apparatus and methods follow.

Light Transmission and optics

Figures 4, 5:
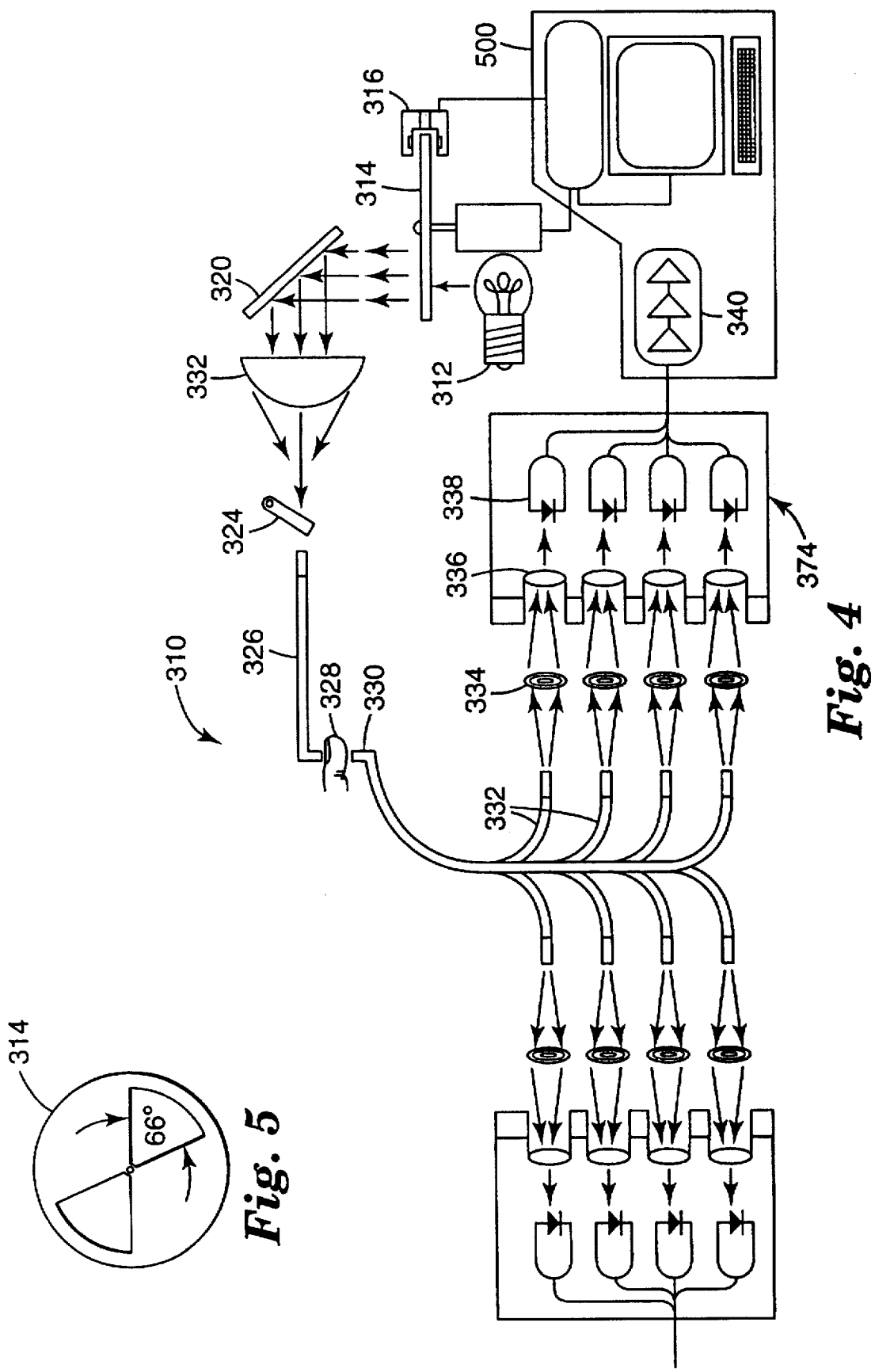
FIG. 4 is a more detailed schematic illustration of an embodiment of the invention for interrogating mammalian tissue using photoplethysmography.
FIG. 5 is an illustration of a "chopper wheel" used in an embodiment of the present invention.

FIG. 4 provides a schematic illustration of one embodiment of the invention that demonstrates how the invention has overcome difficulties in noninvasive photoplethysmography. FIG. 4 shows a system 310 for transmitting light transcutaneously and the optics for maximizing the reception of transcutaneously transmitted light. Briefly, light from a lamp 312 is chopped by disc 314 as detected by a LED-photo-detector pair 316 electrically connected to an electronics and processing module 500. The light is reflected by a mirror 320 and sent through an aspheric lens 322, past a mechanical shutter 324, into a light source fiber optic bundle 326 where it reaches mammalian tissue 328.

After transversing the mammalian tissue 328, the light is received into a light collection fiber optic bundle 330 and divided into between 6 and 10 channels 332, one or each wavelength of interest. Each channel 332 merges into a fresnel lens collimator 334 (as shown ore completely in FIG. 9), which directs the interrogated light in each channel through an interference filter 336. The filtered light from each channel 332 shines on a photodiode 338 for each channel, each diode configured to receive light in a specific light range. Each photodiode 338 converts the received light to an electronic signal which is filtered and amplified as described below with respect to FIG. 11. Software executed by the computer processes the signals as described herein to predict hematocrit, determine a confidence level, and display the photoplethysmographic waveforms and other information of interest.

Transmission of light begins with the generation of broad wavelength light by an incandescent lamp 312. Lamp 312 is commercially available from a number of commercial sources. Preferably, the lamp 312 has multiple filaments and is a unit similar to ones used in overhead projectors commercially available from Minnesota Mining and Manufacturing Company (3M), and is identified as 3M part no. 78-8000-7618-0.

Lamp 312 from 3M was chosen because it has a large filament area which is advantageous for further optical processing of this light, and also has a high energy output being rated at 900 watts at 120 V of supply. In addition this halogen-gas-filled lamp 312 has a built in metal reflector behind the filament, as is commonly employed in overhead projectors. Because the lamp 312 is used in the system 310 at a supply voltage of about 73 V from the power supply (not shown), its output is 37% of the rated output at 120 V (power is proportional to the square of the voltage). This increases the life of lamp 312 significantly.

A precision DC power supply at about 73 V is preferably used. Thus, the power fluctuations in the output of the lamp 312 are minimized to acceptable levels. It is an aspect of the invention to recognize that the relative spectral power output of the lamp 312 should not vary significantly every time it is used. Otherwise, the calibration constants used in the algorithm used to predict hematocrit do not maintain accuracy and precision.

Because the relative spectral output is also a function of the temperature of the filament, by assuring a constant power output, this condition is satisfied.

Alternatively, one could provide a diode feedback loop (not shown) to assist in controlling the relative spectral output.

The incandescent light in the range of 300 nm to greater than 20,000 nm from the lamp 312 is periodically interrupted by a 10 cm (4 inch) diameter disc 314 rotating at high speed about 1 cm above the lamp 312 that has pie-shaped open sectors for transmission of light, as seen in FIG. 5. The disc 314 is preferably made from a metal such as aluminum and preferably has two diametrically-opposed open pie sectors of about 66° opening each. Thus, the disc blocks light during about 228° of each revolution. It is within the scope of the invention to vary either the rotation speed or the amount of blockage, size, and number of the open sectors in order to adjust the amount and duration of light passing disc 314. It is also within the scope of the invention to use opto-electronic shutters such as those that vary the light transmitted through them between various levels depending on the applied electrical signal and at the rate of change of the applied signal.

The light from the lamp 312 is "chopped" for several reasons. The "chopping" of the optical beam sing open pie-shaped sectors on disc 314 unexpectedly reduces excess heating of mammalian tissue that could alter the conditions affecting a noninvasive, transcutaneous prediction of hematocrit. This chopping can also be used to facilitate a lock-in amplification of the signal, thus increasing signal to noise ratio. During the "off" period of the disc 314 when the light from lamp 312 is blocked from the optical train, and a background reading of the signal indicating ambient noise can be subtracted.

A motor drives disc 314 at a speed of from about 2000 revolutions per minute to about 4000 revolutions per minute, and preferably 3000 revolutions per minute. Rotation at the preferred rate gives one open slot passing over the lamp at a preferred sampling frequency of 100 Hz (cycles per second, here 100 pulses/flashes of light per sec.) Each open sector allows about 3.33 milliseconds of complete filament exposure. This time period is referred to as the "sample window". The computer is synchronized as described below such that the computer samples the photoplethysmographic waveform of each wavelength of interest during this 3.33 millisecond sampling window.

Thus, the preferred total duty cycle or light "on" time is about 33.3%. Configuration of lamp 312 and disc 314 in this manner minimizes the undue heating of the rest of the components 320, 322, 324, and 326 in the optical train that follows as shown in FIG. 4 and more importantly limits the temperature rise of the mammalian tissue 328, e.g., the finger which this chopped light eventually interrogates.

The disc 314 is spun by a motor (not shown), preferably obtained from an optical chopper unit model SR540 sold by Stanford Research Systems Inc., of Sunnyvale, Calif.

Preferably, the disc 314 is gold plated on the upstream side exposed to lamp 312 and has an anodized black matte finish on the other or downstream side. The gold plating, by virtue of its low emissivity, minimizes heating of the disc 314, and the black matte maximizes loss of any acquired heat.

Motor Control and Trigger Module

Figure 6:
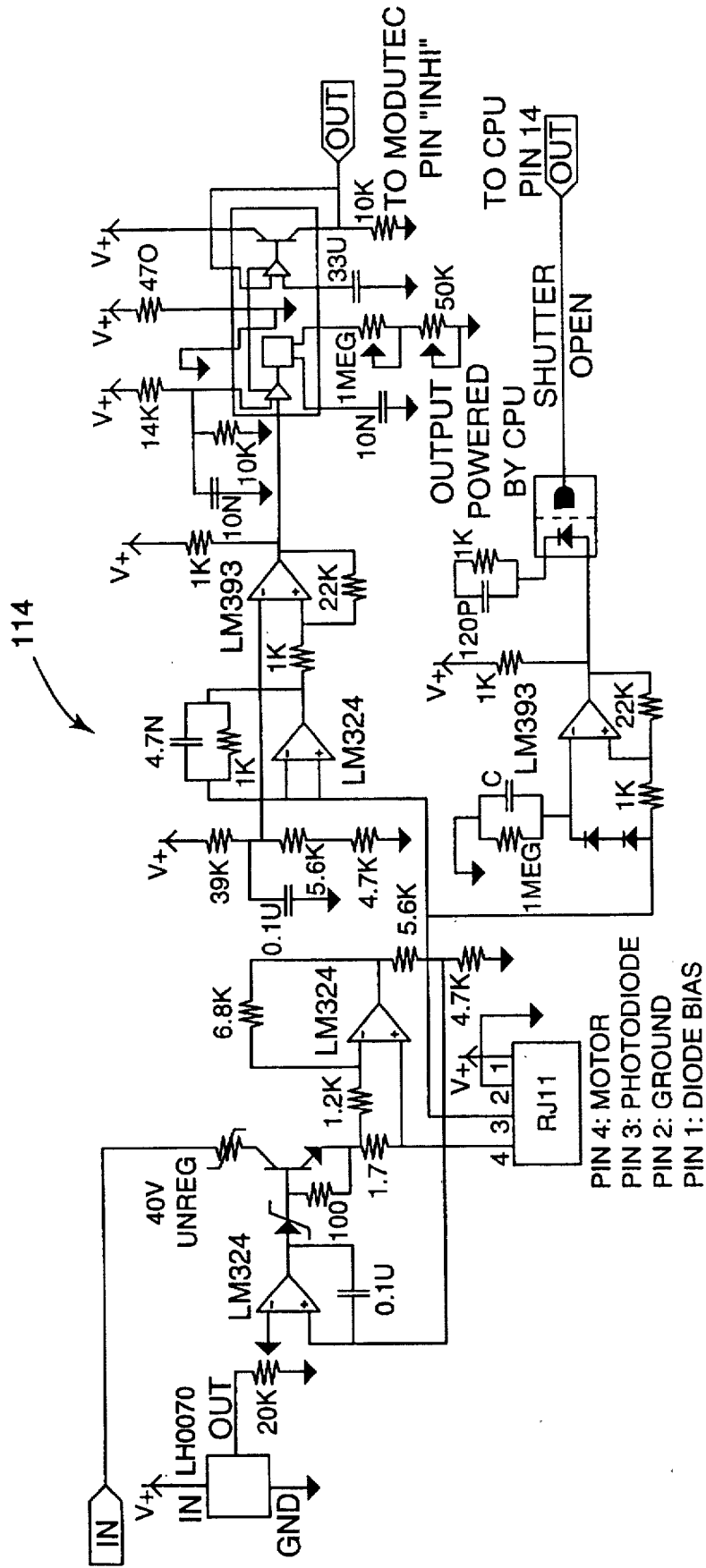
FIG. 6 is an electronic schematic diagram of the motor control circuit for the chopper wheel.

To ensure that the light from the lamp 312 is modulated at the preferred sampling frequency of 100 Hz, the motor control circuit 114 shown in FIG. 6 controls the speed at which the motor rotates disc 314. A panel mounted potentiometer and corresponding meter readout shown in the upper right portion of FIG. 6 allow the clinician to adjust the motor speed by setting the frequency desired. An precision 10 Volt source LH0070 is buffered by amplifier LM324. A motor driving stage consisting of a transistor, Schottky diode and a nonlinear resistor RXE-030 converts this voltage into a corresponding current which is sensed by a 1.7 ohm resistor and LM324 amplifier. This current is connected to pin 4 of a standard RJ11 telephone jack. A photodiode 316 embedded in the motor senses the transitions at which the chopper wheel shutter begins to open over the lamp. The photodiode produces a corresponding pulsed signal which is connected to the motor control circuit via pin 3 of the RJ11 jack. This pulsed signal is used to determine and display the frequency on the aforementioned meter, and also produces the signal SHUTTER OPEN.

The SHUTTER OPEN signal is isolated from the rest of the circuit by optoisolator HP2231. The SHUTTER OPEN signal is used to synchronize the CPU such that the CPU samples the photoplethysmographic signals of all wavelengths of interest during the 3.33 millisecond sampling window.

Referring again to FIG. 4, the light allowed through an open disc sector of disc 314 is then reflected off a "hot" dichroic mirror 320 set at a 45 degree angle to the light beam. This mirror preferably has an area of about 6.5 cm square (2 inches square) and preferably is constructed of a pyrex base and coated with dielectric films manufactured by Omega Optical, Inc. of Brattleboro, Vt. that allows it to transmit through light impinging on it at a 45 degree angle and consisting of wavelengths that are both (a) less than about 650 nm in the visible region and (b) greater than 1350 nm in the near infrared region. The mirror reflects, therefore, preferably all wavelengths in the bandwidth of about 650 nm to 1350 nm onto a about 7.6 cm (3 inches) diameter pyrex glass aspheric condenser lens 322 of about 7.6 cm (3 inches) focal length, i.e., an f/1 lens. Thus, only that light used in predicting hematocrit is processed; extraneous light that might interfere with the prediction or heat the mammalian tissue 328 is discarded through the mirror 320.

The light from the lens 322 is focussed onto one end face of a fiber optic bundle 326 about 0.9 meter long (3 feet) and having about 1.0 cm (0.39 inch) core diameter. This bundle 326 consists of thousands of individual fibers whose jacketing was removed to improve the "packing fraction". Packing fraction refers to the ratio of the true geometrical area computed by adding together the area of each individual fiber to total area occupied by the individual fibers at the end face and the dead space between them. The higher the packing fraction, the more efficient the use of the core diameter. Bundles are made by Fiberguide Industries Inc. of Sterling, N.J.

Another feature of the fibers is that they are made from low water (OH—) content silica. This is important because this invention relies on the efficient measurements of light absorbed by the tissue water. Hence losses of light at wavelengths corresponding to water absorption wavelength bands in other parts of the system are undesirable.

The fibers in the bundle 326, and therefore the bundle's numerical aperture or its light collection ability is chosen to be high, at least 0.5 and preferably about 0.52 so that maximal light is gathered from a wide angle of an acceptance cone of light striking the bundle face from the lens.

Another feature of the optical system 310 is a mechanical shutter 324. This is a piece of metal sheet painted flat black and placed between the lens 322 and the face of the fiber bundle 326 about 3 to 4 mm away from the bundle 326. The shutter can also be made from opaque materials with a plurality of holes or openings of varying intensity such as a wire mesh. This shutter 324 is operated by a small metal rod lever (not shown) so that it can be positioned to partially cover or open a fraction or all of the face of the bundle 326. This allows one to mechanically interrupt the amount of light entering the bundle 326 from the lamp 312. The importance of the shutter 324 lies in the fact that it is possible to vary the light intensity interrogating the mammalian tissue (e.g., a finger) without altering the relative spectral intensity of the light. If the power to the lamp 312 were altered, then the filament temperature and hence the relative spectral intensity would change which would cause an alteration of the system 310 calibration constants used in the prediction of hematocrit. The need to alter the light intensity arises due to the large differences in the thickness of fingers in the general population. Thin fingers that allow more light to be transmitted can saturate the electronic amplifiers 340. Thus, the amount of light used to interrogate a finger must be reduced without changing the relative spectral intensities that could otherwise affect the accuracy and precision of the prediction of hematocrit.

All of the above described components 312, 314, 316, 320, 322, and 324 can be mounted using optical and ordinary laboratory fixtures and mounts. All of the above components can be enclosed in a sheet metal housing (not shown) which is preferably painted flat black to minimize multiple light reflections and effectively remove heat. All the holders of the components of system 310 are preferably similarly painted for the same reason. The housing preferably also includes a 20 watt fan blowing air over the components to maintain an acceptable temperature condition of about 65° C. and minimize a rise in temperature of greater than about 80° C. during operation of the system. The housing and the enclosed components can be mounted on a larger plate, preferably made of aluminum about 0.7 cm (0.3 inch) thick.

Loss of available light for interrogation of tissue 328 is a factor to be overcome. Because of the limited wavelengths needed (650–1330 nm) and because of the use of various components to attain, with stability and reproducibly, light of a relative spectral intensity, loss of light is a necessary compromise for the effectiveness of the system. Mirror 320 loses about 10% of the light intended for lens 322. Lens 322 loses about 20% of the light intended for bundle 326. Within bundle 326, more than 40% of the light intended for tissue 328 is lost. It is understood that other schemes such as allowing light from lens 322 to directly impinge on finger 328 by removing fiber bundle 326 would significantly increase the light but decrease the flexibility of using the device. In all cases, particularly the bundle, the amount of loss is function of the wavelength.

Transmitted Light Reception and Data Acquisition

Figure 7A:
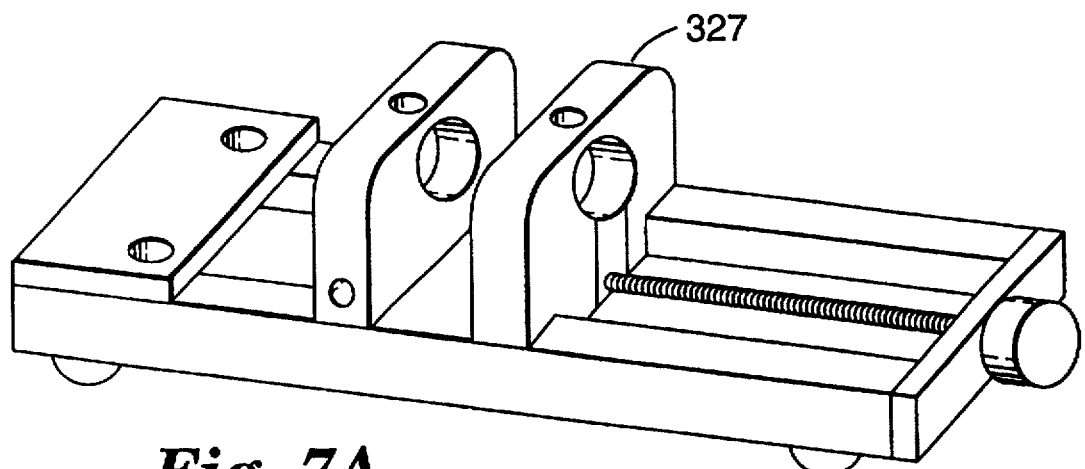
FIGS. 7A and 7B are perspective illustrations of a finger holding device in an embodiment of the present invention.
Figure 7B:
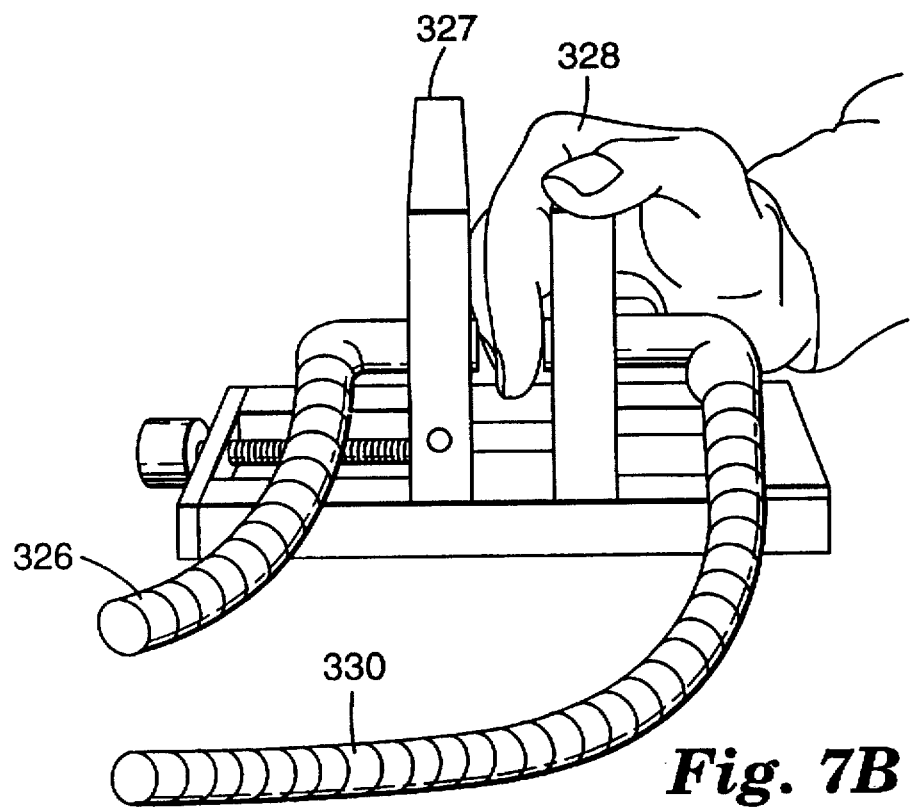

The optical fiber bundle 326 carrying the selected wavelength light from the lamp 312 has its other end terminating in a finger holder device 327. Referring to FIGS. 7A and 7B, this device 327 preferably comprises two vertical plates of acrylate plastic. The first plate receives the light emitting bundle 326 into an about 1.2 cm (0.5 inch) diameter hole in it, anchored by a set screw, such that the bundle 326 is in a horizontal position with its end protruding on the other side of the plate. This acrylate plate also swivels around a vertical axis located at the hole. A second acrylate plate with a hole similar to the first receives a second bundle 330, that collects light after transmission through the finger 328.

While in the embodiment shown in FIG. 7, a finger is chosen as the mammalian tissue through which light travels from bundle 326 to bundle 330, it is understood that system 310 and particularly device 327 can be modified to interrogate other types of mammalian tissue. In the case of humans, the device 327 can be reconfigured to an earlobe, the bridge of a nose, or buccal mucosa inside a mouth without departing from the scope of the present invention.

While in the embodiment shown in FIGS. 7A and 7B, a transmission system is shown, it is to be understood that the scope of the present invention includes the use of optical reflectance techniques in order to noninvasively predict hematocrit.

The finger holding device 327 allows one operating system 310 to position a finger in it, such that the light emitting bundle 326 from the lamp 312 is in contact with the nail of the finger and the second bundle 330 is in contact with the palmar side of the finger opposite the nail. A screw with a thumbwheel allows the two plates to be brought together so that the finger 328 is squeezed gently in the device 327 between the two bundles 326 and 330. A swivel on the first plate (not shown) is used so that the bundle 326 face is parallel to the nail of finger 328 due to the fact that the finger 328 is almost wedge-shaped at its extremity.

The collecting bundle 330 is also about 0.9 meter (36 inches) in length and made from high numerical aperature (NA) fibers similar to those of the first bundle 326. After about 330 cm (12 inches) from the common end (core diameter of about 1.2 cm) of bundle 330 that collects light from the finger 328, the bundle 330 splits into several smaller-diameter channels that can transmit light in different channels to specialized photodetectors 338 for spectral intensity detection. Each channel and associated photodetector corresponds to a different one of the wavelengths of interest.

Preferably the bundle 330 splits into as many channels 332 as are needed to transmit light to photodetector 338. As the core area of the bundle 330 at the common end is split into multiple smaller core area channels 332, using too many channels 332 can further cause a loss of interrogated light. Using too few channels 332 will not provide sufficient number of wavelengths in the system 310.

The total number of channels 332 and photodetectors 338 depends on the number of discrete wavelengths used in the algorithm to predict hematocrit. The number of wavelengths can range from about 2 to about 12 as described below. The number of wavelengths desirably ranges from about 5 to about 10, with 8 discrete wavelengths preferred. Thus, in a preferred embodiment shown in FIGS. 8A and 8B (also shown in FIG. 4), there are eight channels 332 of bundle 330, each providing light into a discrete channel.

As seen in FIGS. 8A and 8B, because the light incident on the mammalian tissue 328 has unequal intensities at the various wavelengths and because the wavelengths longer than 1000 nm are more strongly absorbed by mammalian tissue, the channels 332 carrying the light intended for analysis at these wavelengths exceeding 1000 nm have a larger core diameter. In channels 332, two channels 332 have a core diameter of about 7 mm for use with Germanium photodetectors described below for wavelengths greater than 1000 nm, while six channels 332 have have a core diameter of about 2.5 mm for use with silicon detectors, as explained below for wavelengths less than 1000 nm.

All bundles 326 and 330 and channels 332 preferably have a braided cloth covering and enclosed in a stainless steel flexible monocoil sheathing. The end faces of each bundle 326, 330 and channels 332 are preferably made from stainless steel and utilize medical grade epoxy with an ability to withstand high temperatures (up to 80° C.). All bundles 326 and 330 and channels 332 were made by Fiberguide Industries of Sterling, N.J.

As seen in FIGS. 8A and 8B, the eight channels 332 of the collecting bundle 330 terminate at a platten holder 360. This platten holder 360 is preferably a vertical piece of about 1.2 cm (0.5 inch) thick aluminum with eight holes, four in each of two columns.

Figure 9:
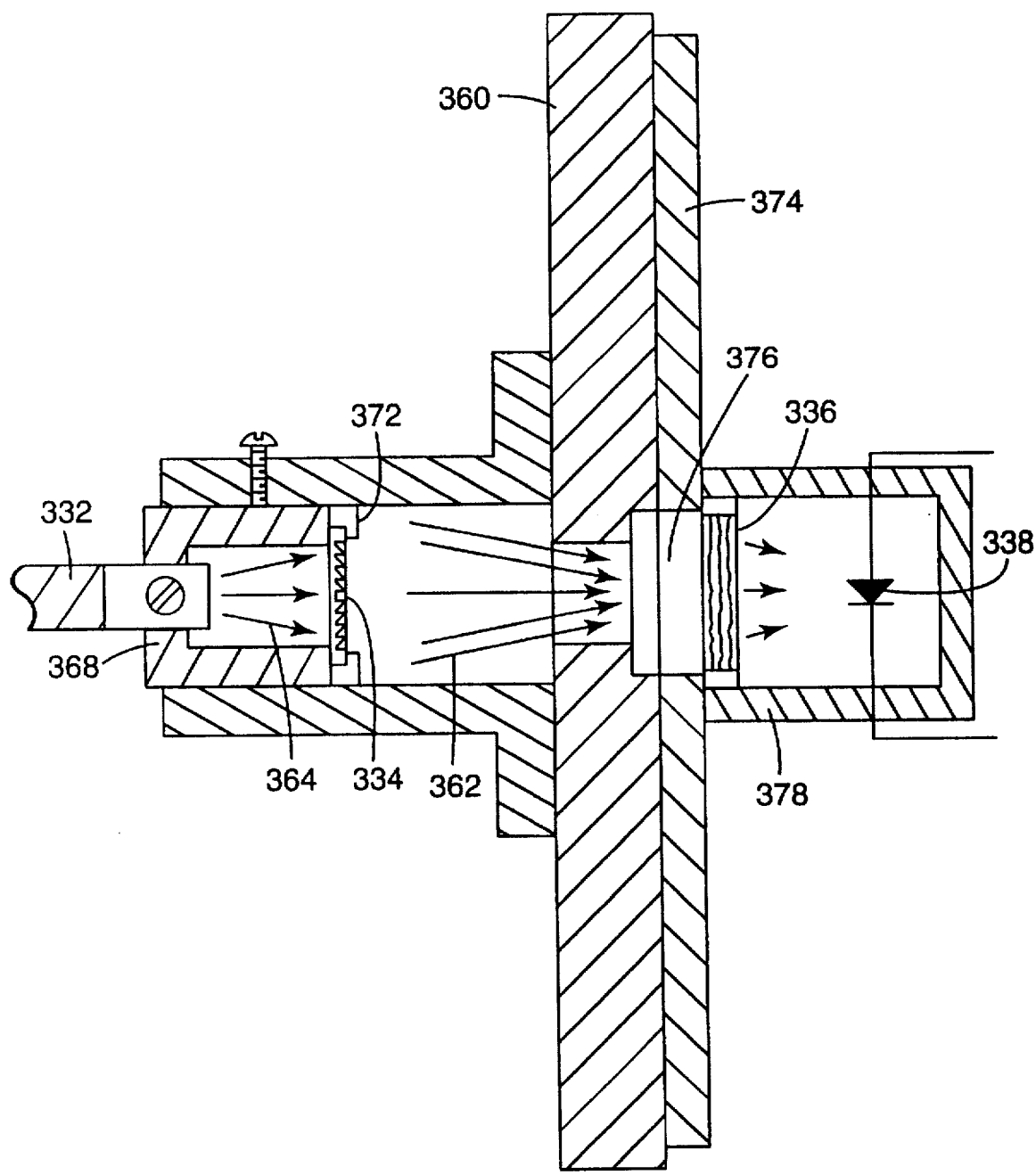
FIG. 9 is a schematic illustration of an embodiment of the invention for collimating and filtering light from interrogated tissue.

As seen in FIG. 9, on one side of the holder 360 are affixed cylindrical tubular pieces 362 that receive a lens-bundle assembly 364. Each lens-bundle assembly 364 can be adjusted to fit inside the tubular piece 362 at variable depths and fixed in position by set screws 366. Each assembly 364 preferably comprises a ferrule 368 that accepts the end face of one channel 332 of the collecting bundle 330; at the other end of ferrule 368 is a lens 334 (as seen in FIG. 9), preferably a circularly cut 0.158 cm (1/16 inch) thick acrylate Fresnel lens 334 (as seen in FIG. 9) held in place by a retaining ring (not shown). All machined parts are preferably made from black anodized aluminum. First, the Fresnel lens 334 is set in the ferrule 368, and then the channel 332 is inserted into the other end of the ferrule 368, such that the distance between the lens 334 and the inserted channel 332 face is exactly equal to the focal length of the Fresnel lens 334.

This arrangement in ferrule 368 produces a shaped beam (e.g. a fairly collimated beam) of light exiting from the Fresnel lens 334. This lens-assembly ferrule 368 is inserted into the tubular piece 362 on the platten holder 360 and preferably fixed at a distance such that the light striking the photodetectors 338 on the other side of the platten 360 gives a maximum optical signal.

Considering the platten holder 360, on the side opposite the channels 332, there is affixed a removable platten 374, preferably a metal machined plate that is easily screwed on to the platten holder 360 by thumbscrews (not shown) that has machined wells 376: one opposite each hole that correspond to the eight channel-lens assemblies 362. In each well fits a module 378.

Each module 378 preferably comprises an interference filter 336 (as seen in FIGS. 4, 8, 9, and 10), each generally of a specified, known center wavelength and about 10 nm full width at half power. These filters 336 are about 2.5 cm (1 inch) in diameter and 2 to 5 mm in thickness. The center wavelengths vary as specified. In a preferred embodiment, the filters 336 include the water band in the 1165 to 1330 nm range, the oxyhemoglobin-deoxyhemoglobin isosbestic points in the 800 nm range, the arterial blood oxygen saturation measurement wavelengths in the vicinity of 660 nm and 910 nm, and the water band wavelengths in the 965 nm range.

Figure 10:
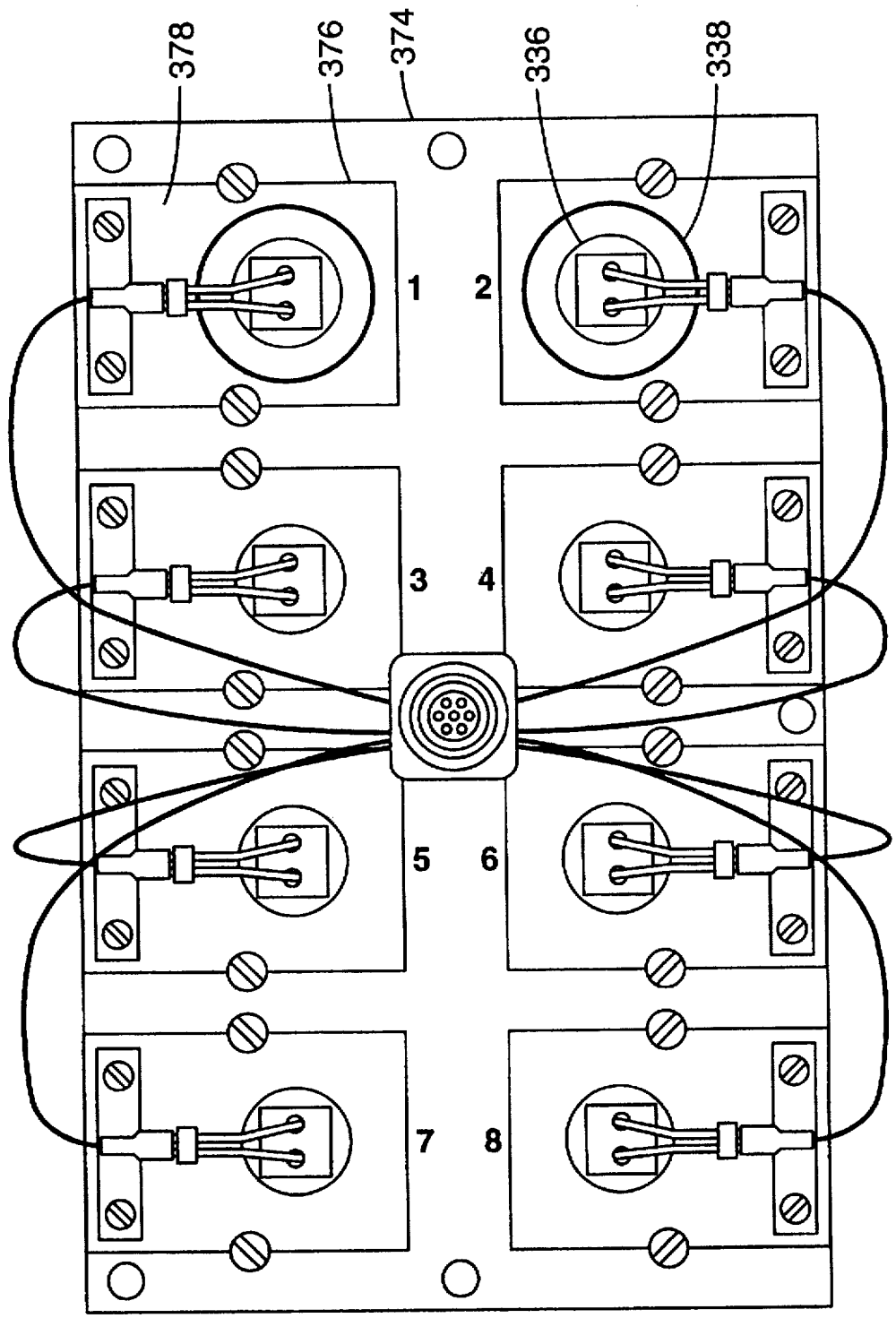
FIG. 10 is an illustration of one platten shown in FIG. 8, showing photodetectors used in the present invention.

As seen in FIG. 10, each platten contains germanium photodetectors having a 10 mm diameter and 79 mm$^2$ active area and upper water band filter (1165–1330 nm) 336 in each of the first two wells. The other six wells contain square silicon photodetectors having 100 mm$^2$ active area and filters 336 for wavelengths under 1000 nm.

The germanium photodetectors are commercially available from EG&G Judson of Montgomeryville, Pa., while the silicon photodetectors are commecially available from Hamamatsu Corporation of Bridgewater, N.J. The interference filters are commercially available from Omega Optical Inc., of Brattleboro, Vt.

In a preferred embodiment, the two, upper water band filters filter for 1300 nm and 1195 nm light plus/minus 2 nm for each. The commercially available Germanium photodetectors used with such filters are Model #RJ16R10MSC sold by EG&G Judson.

Also in the preferred embodiment, the other six filters filter for 972 nm, 1100 nm, 820 nm, 805 nm, 910 nm, and 660 nm light, respectively, plus/minus 2 nm for each filter. The commercially available silicon photodetectors used with such filters are S2387-10.10R sold by Hamamatsu Corporation.

The selection of wavelengths depends on the choice of the equations used to predict hematocrit or other analytes of interest as described above. Preferably, the selection of wavelengths can be each of the Preferred Range wavelengths described in Table 1 above. More preferably, the wavelengths can be the set of 680, 810, 837, 900, 972, 985, 1207, and 1315 nm. Most preferably, the wavelengths can be the set of 660, 805, 820, 910, 972, 1100, 1195, and 1300 nm.

Referring again to FIG. 4, as stated previously, there is known to be a severe loss of light intended to interrogate tissue 328. Within tissue 328, there is considerable light scattering of the interrogating light. Only about 5% of the light entering a finger 328 is collected by bundle 330. Then bundle 330 splits that diffusely transmitted light from the tissue 328 into several channels 332, eight in a preferred embodiment based on the number of wavelengths to be analyzed. Lenses 334 and filters 336 also have some loss of light transmitted.

Thus, from lamp 312 to the photodetectors 338, the drop in wattage of light is severe, to the range of nanowatts of light detected. Unexpectedly, the system 310 can use such miniscule amounts of light in several, discrete wavelengths to provide a prediction of hematocrit. Alteration of system 310 to provide an increased amount of light reaching photodetectors 338 could change the temperature of tissue 328 being interrogated. Thus, the method and apparatus of the present invention unexpectedly achieves delivery of an effective amount of interrogated light to photodiodes for signal processing and prediction of hematocrit.

Referring again to FIG. 10, all eight photodetectors 338 are connected by shielded wires to a miniature 20 pin connector (not shown) for electrical connection to amplifier 340 (See FIG. 4). An easily removable electrical connector with a cable attaches the platten 374 to the electronics box containing amplifier 340. The photodetectors 338 convert the time variant wavelength specific optical signals contained in the light collected from the finger 328 into equivalent electronic signals to be processed by the rest of the system 310. The output from the photodetectors 338 (photocurrent) goes to the input of the electronics portion of the system 310 through a shielded twisted pair cable; the photocurrent is input to a differential pre-amplifier as described below with respect to FIG. 11.

Alternatively, the present invention can replace the broad band light source 312, disc modulator 314, fiber bundles 326 and 330 and optical wavelength filters 336 and Fresnel lenses 334 with small solid state modulated monochromatic light sources such as light emitting diodes, super light emitting diodes, laser diodes and similar devices in order to achieve a more compact and less mechanically and optically cumbersome system 310.

Signal Processing

Figure 11:
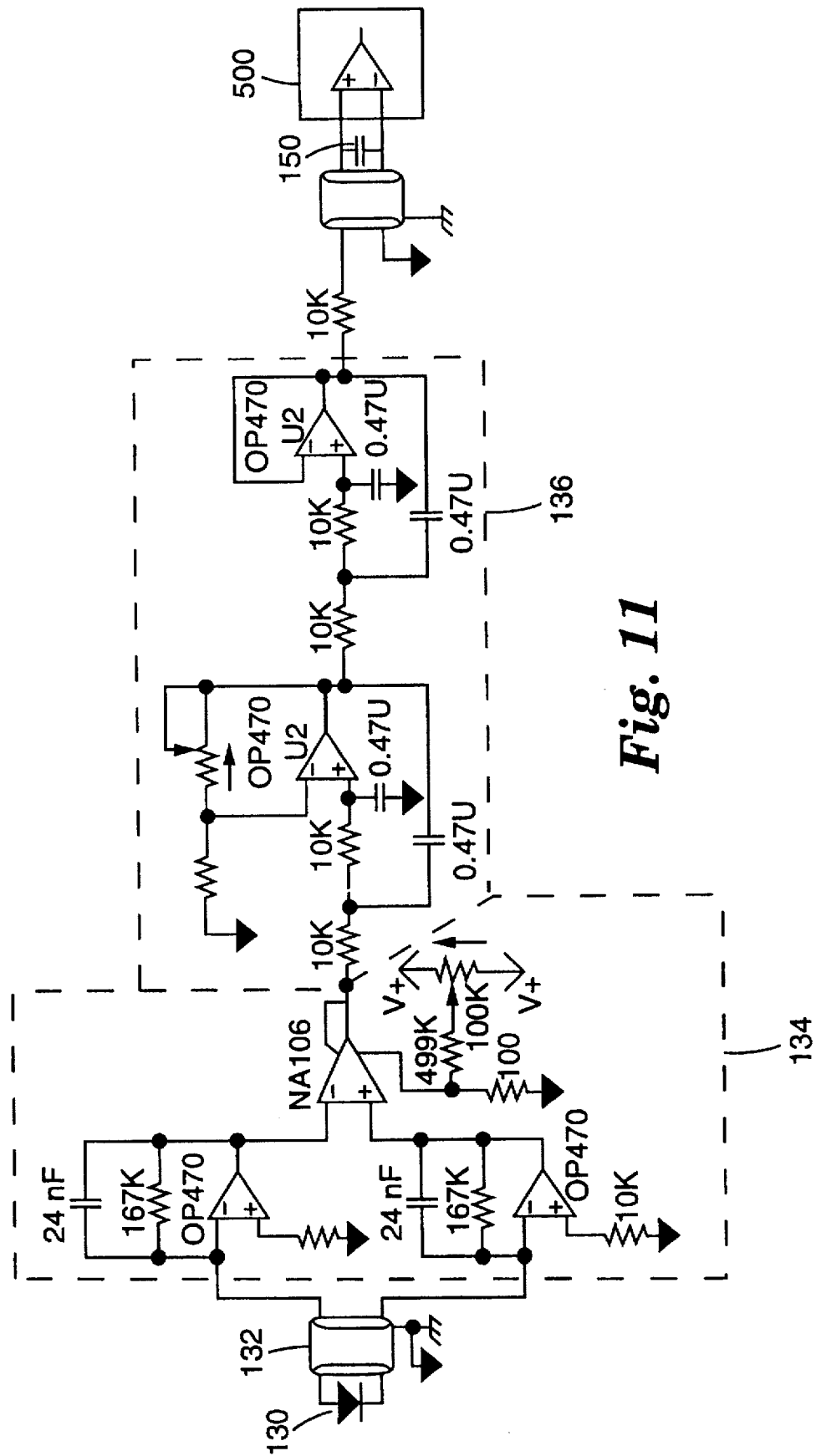
FIG. 11 is an electronic schematic diagram for amplification and filtering of the photoplethysmographic signals.

FIG. 11 shows an electrical schematic diagram of the amplifier and filter electronics 120 shown in FIG. 2 corresponding to one of the wavelengths of interest. Each set of amplifier and filter electronics 120a–n are preferably implemented with the identical circuitry as shown in FIG. 11. However, in some circumstances it may be desirable to tune the electronics to the specific type of photodetector used.

In FIG. 11, the optical radiation from the fiber bundles is incident on a photodetector 338, which converts the optical radiation into a corresponding photocurrent. The photodetector is connected to the inputs of an instrumentation amplifier 134 via individual, shielded twisted pair wires 132. The cable shields are connected to chassis ground to reduce common mode noise. The instrumentation amplifier 134 is comprised of a differential pre-amplifier and a precision device (INA106). The differential pre-amplifier configuration also results in very high rejection of common mode signals, and includes two operational amplifiers U1 and associated circuit components. A 167K ohm feedback resistors is coupled to the inverting input of each operational amplifier U1. An 24nF capacitor in parallel with each feedback resistor reduces the high frequency content (i.e., reduces high frequency peaking) of the signal at the output of each operational amplifier U1. The cutoff frequency of this RC pair is 40.8 Hz. 10K ohm resistors connected to the non-inverting terminals of the operational amplifiers U1 reduce noise by compensating for unequal operational amplifier bias currents. The output of the pre-amplifier stage is a differential signal comprised of a negative voltage at the output of the top operational amplifier and a positive voltage at the output of the bottom operational amplifier.

In the preferred embodiment, low noise operational amplifiers are used for the pre-amplifiers. Low current noise operational amplifiers are preferred for high shunt resistance photodetectors, while low voltage noise operational amplifiers are preferred for low shunt resistance photodetectors.

Immediately following the pre-amplifier stage is a precision device (INA106) which converts the differential signal from the preamplifier stage into a single ended electrical output. When properly configured, this device subtracts the output of the top operational amplifier from the output of the bottom operational amplifier, resulting in a conversion of the two individual signals to one voltage signal. This device also amplifies the converted signal by a factor of ten.

Two operational amplifier circuits U2 configured as a fourth order low pass Butterworth filter 136 further reduce the high frequency content of the signal. The low pass filters are preferably comprised of two consecutive second order Butterworth filters U2, each having a cutoff frequency of 33.8 Hz. The frequency response of the combined filters U2 is a fourth order low pass filter with a cutoff frequency of 33.8 Hz.

An RC filter, comprised of 10 ohm resistor and capacitor 150, further low pass conditions the signal. The RC filter ground is tied to the ground of the processing module 500. The resistor, R, also serves to decouple the distributed capacitance of the cable that connects the electronics to the processing module 500. The cable is 360 degree shielded with the shield tied to ground at the ground of Butterworth filter 136.

The processing module 500 is preferably implemented with a Keithley-Metra Byte Analog to Digital Converter board and a Toshiba 3200 portable computer. The computer includes a 80386 microprocessor augmented by the Keithley-Metra Byte analog-to-digital (A/D) converter board. The processing module 500 receives the analog signal and converts it to a digital representation via the A/D board.

Figure 12:
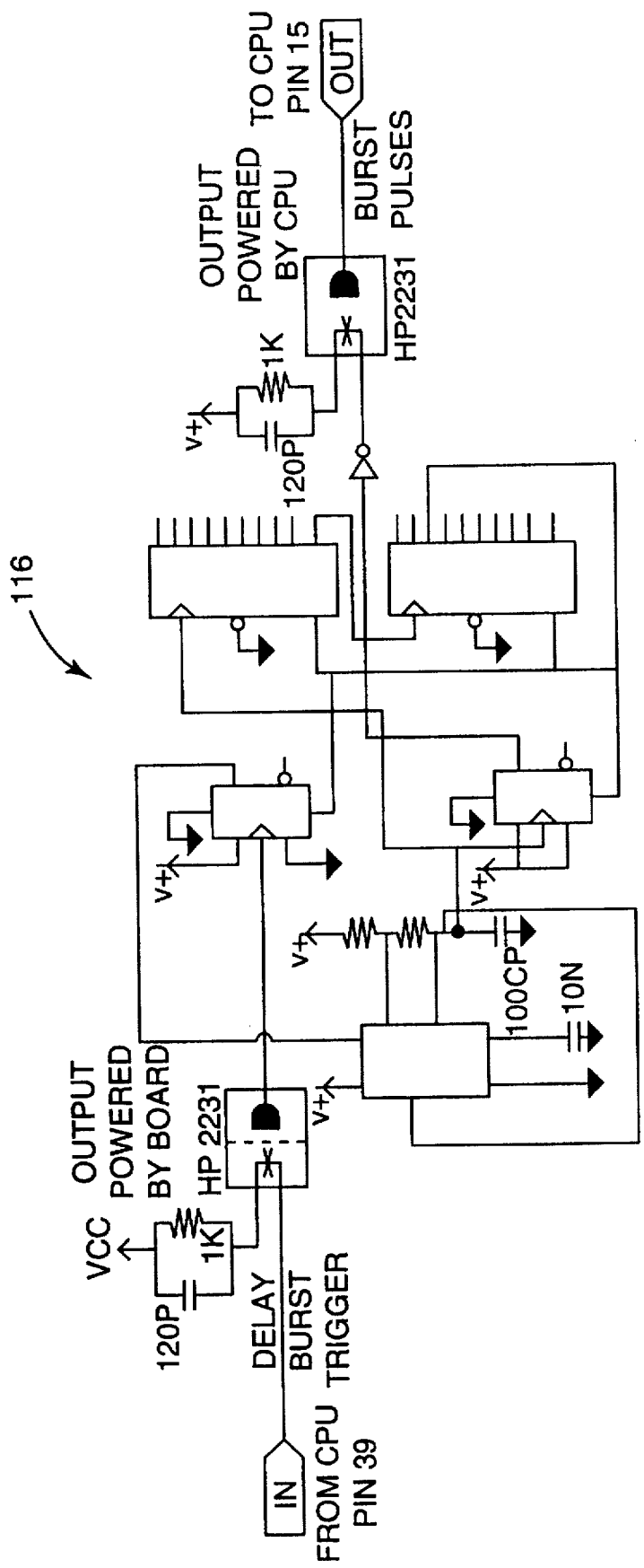
FIG. 12 is an electronic schematic diagram of the trigger control module.

Samples of the digitized plethysmographic waveforms are preferably captured by the CPU during the 3.33 milliseconds of complete lamp filament exposure (the sampling window). As described above with respect to FIG. 6, the SHUTTER OPEN signal is used to synchronize the CPU such that the CPU samples the photoplethysmographic signals of all wavelengths of interest during the 3.33 millisecond sampling window. The SHUTTER OPEN signal corresponds to the time at which the pie-shaped sectors of disc 314 just begin to open over lamp 312. After receipt of the SHUTTER OPEN signal, the CPU waits for a delay corresponding to the time between receipt of the SHUTTER OPEN signal and the time when the lamp filament is completely exposed. After that delay has elapsed, the CPU generates the signal DELAY BURST TRIGGER, shown in FIG. 12. Upon receipt of the DELAY BURST TRIGGER signal, the trigger control circuit 116 of FIG. 12 generates a series of burst pulses.

Upon receipt of each burst pulse, the CPU samples the waveform for one of the wavelengths of interest. In the preferred embodiment, for example, eight burst pulses, each corresponding to one of the eight wavelengths of interest, are generated by trigger control module 116 over a period of about 60 microseconds. Upon receipt of each burst pulse, the CPU samples the corresponding waveform of interest.

Thus, in the preferred embodiment, all eight waveforms are sampled in a serial fashion over a time frame of approximately 60 microseconds during each 3.33 milliseconds of complete lamp filament exposure. Although all wavelengths are not sampled simultaneously, the samples are taken over a time frame of about 60 microseconds in the preferred embodiment. This 60 microsecond time frame is very small when compared to the time frame of any relevant photoplethysmographic information in the signal of interest, such that for practical purposes, the samples are essentially captured "simultaneously". However, it shall be understood that the waveforms for all wavelengths of interest could also be sampled in parallel without departing from the spirit and scope of the present invention.

Data Storage

Figure 13A:
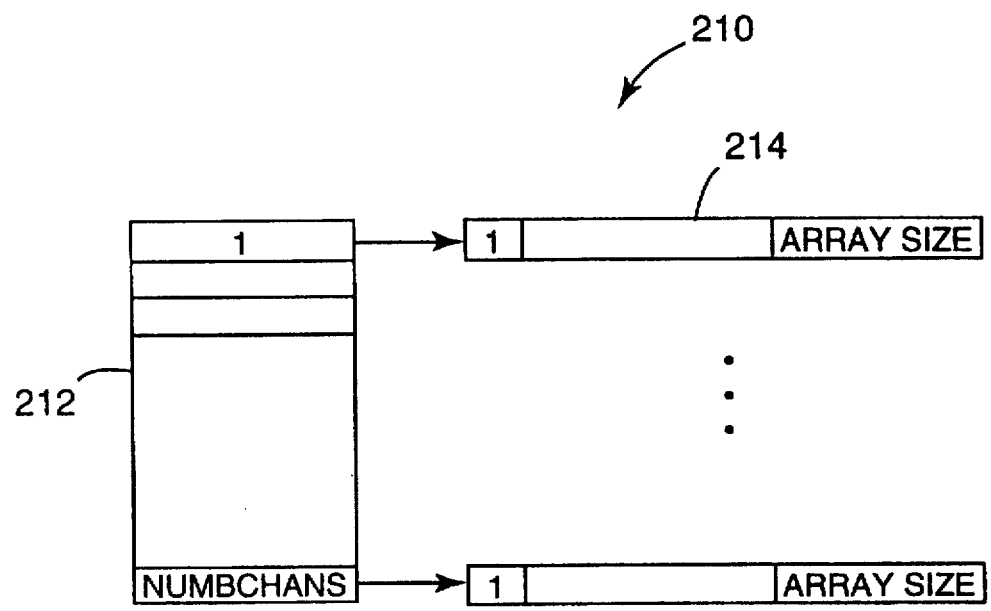
FIGS. 13A and 13B show exemplary two dimensional arrays in which raw data and peak and valley locations are stored, respectively.

After the waveform samples are captured, the raw data is converted to volts and is stored in two-dimensional arrays 210 such as that shown in FIG. 13A. This structure is an array of pointers 212, one for each channel, to an array of raw data such as array 214. In the preferred embodiment, the total number of channels is stored in the variable "Numbchans" and in the preferred embodiment is equal to eight. Also in the preferred embodiment, each array can store up to 512 data points per channel, so the variable "ArraySize" in FIG. 13A is equal to 512 in the preferred embodiment.

The memory used for the actual sampling is preferably configured to act as a ring buffer. The DMA buffer used by the Keithley-MetraByte A/D card is split into two blocks. Using the DMA, the processing control procedures described below read from one block of DMA while writing into another. When one block has been completely written, post-processing is performed on that block of data. All of this is accomplished while the CPU continues to sample data into the next block of dynamic memory.

Processing Control

Figure 14:
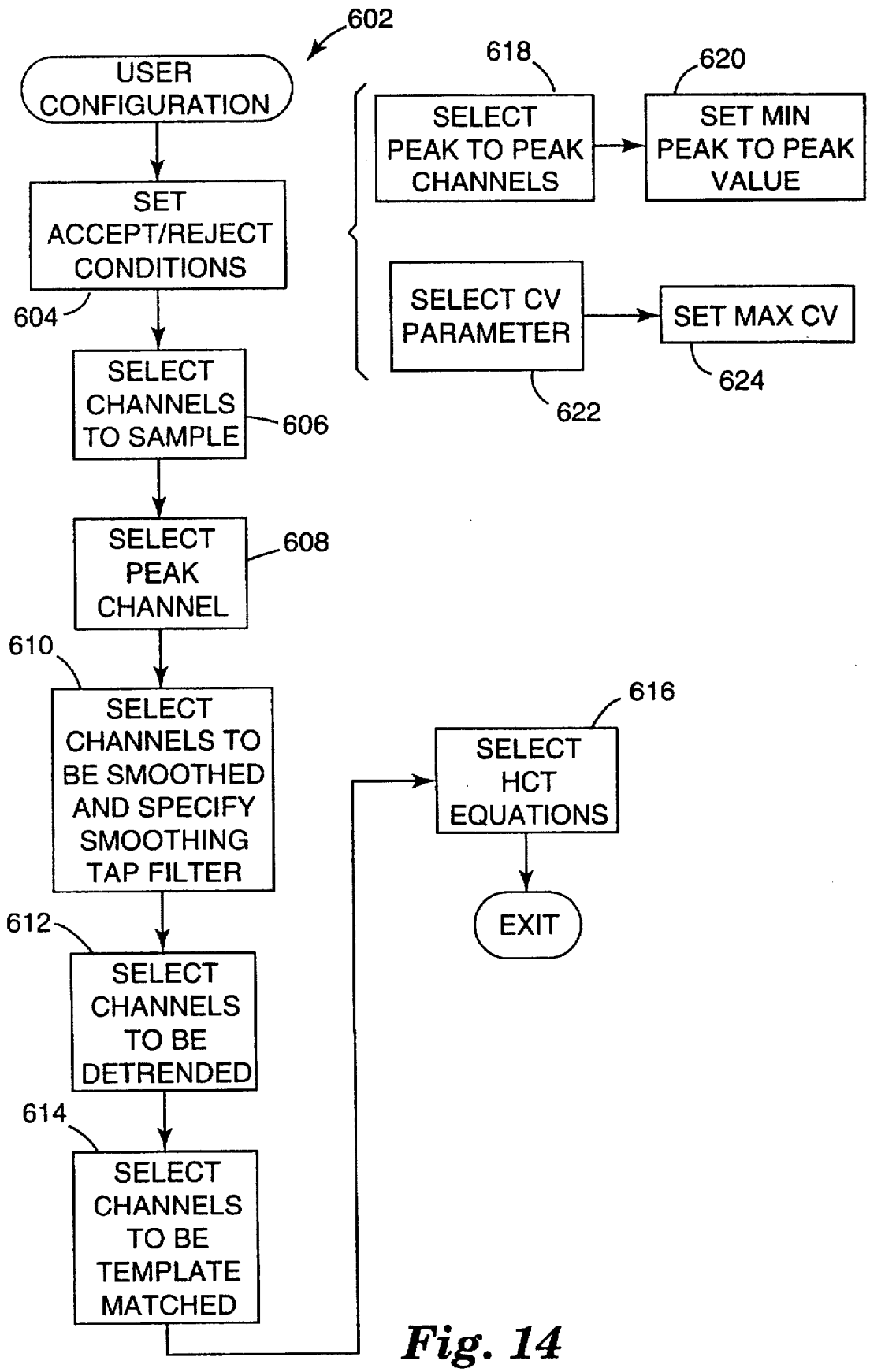
FIG. 14 is a flow chart of the user preconfiguration process.

FIG. 14 shows the process by which a user is able to configure several system parameters. First, while it is possible to visually evaluate the quality of the waveforms obtained, it is a feature of the present invention to provide and apply repeatable, quantifiable measures which evaluate the waveforms and produce numerical "figures of merit" which are displayed to the screen. To this end, the user is able to set quantifiable performance indices against which the waveforms are evaluated for their ability to convey an accurate prediction of hematocrit. In the preferred embodiment, the two parameters used for this are the peak to peak voltage of two user configurable channels, and the coefficient of variation of a user configurable parameter.

In general, the two channels having the lowest pulsatile power (and hence a low signal to noise ratio) are specified for the former purpose at blocks 618 and 620. If the peak to peak amplitude of these channels falls below the user specified minimum, a REJECT message is displayed, indicating to the user that further data should be obtained.

The other performance index of the preferred embodiment is the coefficient of variation of at least one H Value (described in more detail below). If the CV of the specified H Value exceeds the limit set by the user at blocks 622 and 624, the REJECT message will be displayed. If both the peak to peak amplitudes and the CV are within the user specified limits, an ACCEPT message is displayed (see FIG. 28).

FIG. 14 also shows that the user is also able to select which channels are to be sampled at block 606, and which channel is to be used for peak and valley detection at block 608. This designated "peak channel" is typically the isosbestic channel as described in more detail below with respect to FIGS. 19A and 19B.

If upon visual inspection the displayed waveforms are excessively noisy or contain considerable drift, or where the displayed peak to peak amplitudes and/or coefficient of variation measure are unacceptable, the user may, on a channel by channel basis, choose to process the signals further in an attempt to improve the confidence in the hematocrit prediction. When the signals for one or more channels appear excessively noisy, the user may elect to smooth the raw data for those channels before the signals are further processed. In doing so, the user selects which channels are to be smoothed and the order of the tap filter that is to be used on the raw data for the channels selected at block 610.

On channels where considerable drift or baseline trend is present, the user may, on a channel by channel basis, detrend those channels at block 612. The detrending procedure is described in more detail below with respect to FIG. 16.

On channels having a low signal to noise ratio (SNR), the user may elect, on a channel by channel basis, to template match the low SNR signals to a higher SNR signal (usually the designated peak channel) at block 614. The template matching procedure is described in more detail below with respect to FIG. 20.

The user is also able to input the equations which are used in the hematocrit prediction at block 616.

Figure 15:
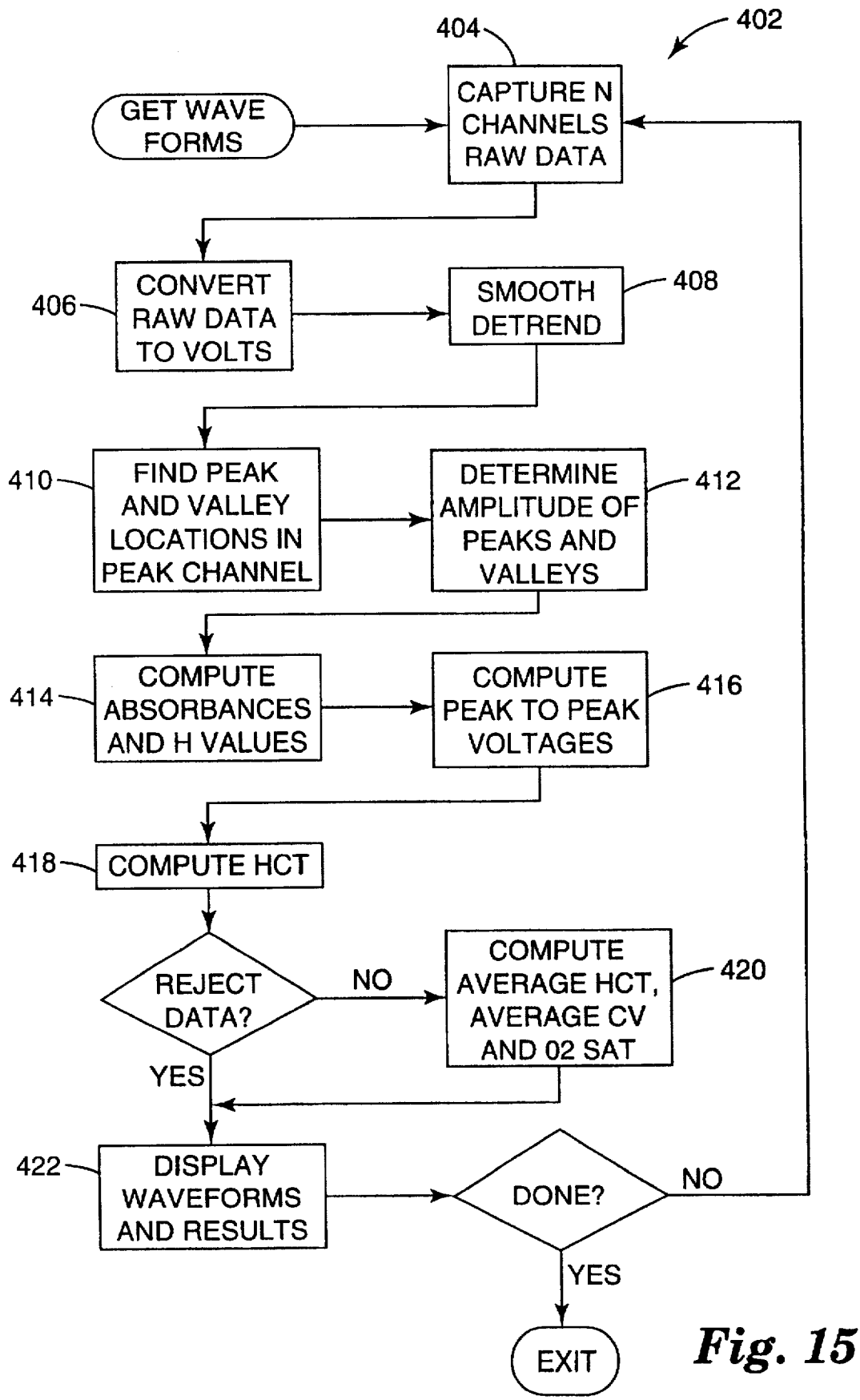
FIG. 15 is a flow chart of the processing control steps of the present invention.

FIG. 15 shows a simplified flow chart of the control software for the present apparatus for noninvasive determination of hematocrit. A detailed computer program listing of the control software can be found in the attached Microfiche Appendix.

As shown in FIG. 15, the CPU first captures the raw data for each of n channels (eight in the preferred embodiment). The raw data is converted to volts and is stored in memory as described above. Control block 408 will smooth and/or detrend selected channels if so configured by the user as described above with respect to FIG. 14. Next, the location of the peaks and valleys of the designated "peak channel" are computed and stored by control block 410. In control block 412, the amplitude, or voltage value, of the peaks and valleys for the photoplethysmographic waveform for each wavelength of interest are computed.

Once the values of the peaks and valleys for each channel are known, a pseudo-absorbance for each peak/valley pair is calculated in control block 414.

Also, the values of these pseudo-absorbances are combined in control block 414 to compute the H Values, which are combined in a prediction of the hematocrit in control block 418. The peak to peak voltages (the AC component) of the user selected channels, most preferably the two channels with the lowest pulsatile power and/or lowest signal to noise ratio, are also calculated. These peak to peak voltages are used by the present system as described above to reject the data if the peak to peak value falls below a user settable threshold.

If the data is not rejected for the reasons cited above and because of patient movement artifact, instrument disconnection, or unacceptable coefficient of variation, as described below, control block 420 computes the average hematocrit, average oxygen saturation and an average coefficient of variation.

Whether or not the data is rejected, the waveforms and results are displayed at control block 422. The entire process continues while the CPU continues to sample each channel until the user signals to quit sampling data.

Detrending

Although non-invasive measurement of hematocrit can be accomplished by measuring the transmission of light through blood perfused tissue at appropriate wavelengths, in practice these measured signals can be corrupted by artifact due to respiration and movement, particularly when collected in a clinical environment. This artifact is a form of low-frequency noise that can also be described as data trend or baseline drift. When this drift or trend is significant the hematocrit measurement is subject to error. The present invention therefor provides an order-adaptive filter for de-trending data to improve the accuracy and precision of hematocrit measurement via photoplethysmography.

Figure 16:
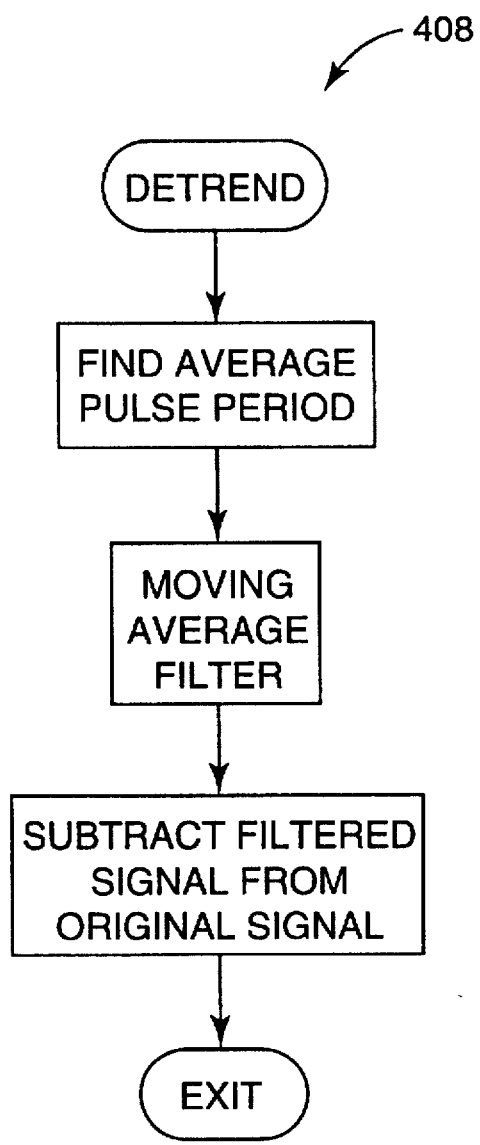
FIG. 16 is a flow chart of the detrending procedure of the present invention.

The de-trending process itself is straightforward and the processing steps are shown in FIG. 16. First, the average pulse period is found over the data interval of interest. Typically, the data is detrended in blocks of from 4 to 8 pulse periods. The measured pulse period 'x' in seconds corresponds to N discrete time steps in the sampled waveform. More precisely, N='x'·fs where fs is the sampling frequency in Hz (100 Hz in the preferred embodiment. N is then rounded to the nearest odd integer. Next, the pulsatile signal is filtered with a Moving Average (MA) filter of length N using the following equation:

$$\mu(n) = 1/N \sum_{k=n-\frac{(N-1)}{2}}^{k=n+\frac{(N-1)}{2}} x(k)$$

The detrended signal x*(n) is then obtained by subtracting the filtered signal from the original signal using the equation:

$$x^*(n) = x(n) - \mu(n)$$

By tuning the MA filter to the pulse period, the moving average is always calculated over a pulse period. This blocks the pulsatile variation from leaking into the baseline waveform $\mu(n)$ leaving only the true drift or trend signal component. When the filter length N (averaging interval) is equal to the pulse length, the pulse frequency and its harmonics are essentially nulled. This approach has a significant advantage in that nulling of the pulse frequency is guaranteed. Other filtering approaches will not necessarily null the pulse frequency and therefore their baseline waveforms may be contaminated with residue of the pulsatile waveform. Additional advantages of this MA filter include ease of implementation, unconditional stability, and linear phase response.

If the data has been detrended, the calculation of H Values for detrended data requires that the intensity values be calculated in a specific manner. The detrended peak and valley levels $I^*_p$ and $I^*_v$ are determined from the detrended signal x*(n). Then the baseline component $I_{BL}$ is added back on in order to provide the appropriate offset:

$$I_p = I^*_p + I_{BL}$$
$$I_v = I^*_v + I_{BL}$$

The particular baseline value for a peak-valley combination is the value of $\mu(n)$ that is halfway between the peak and valley time indices. For example, if valley I occurs at time p and peak I occurs at time q then $I_{BL}$ is given by:

$$I_{BL} = \mu\left(\frac{q-p}{2}\right)$$

It shall be understood that these peak and valley intensity values are not the same as those calculated from the original data. It may appear that the baseline value is removed and then simply added back on again. This is not the case. When the data is de-trended, the MA value $\mu(n)$ that is subtracted from the peak is different from the MA value subtracted from the valley, because $\mu(n)$ is a time-varying waveform. However, when the intensity values are reconstructed, the baseline value is the same for both the peak and the valley.

Table 2 shows H Value data for two patients. The asterisk on the H Value indicates that it is calculated on detrended data. Note that in all cases the de-trended H Values have a lower coefficient of variation.

| | Patient A | | | | | | | | Wavelength Ratio |
|---|---|---|---|---|---|---|---|---|---|
| | hv1 | hv1* | hv2 | hv2* | hv3 | hv3* | hv4 | hv4* | |
| Mean | 0.2409 | 0.2518 | 0.0360 | 0.0376 | 0.2409 | 0.2517 | 1.3220 | 1.3106 | 1–3 |
| SD | 0.0485 | 0.0205 | 0.0072 | 0.0030 | 0.0485 | 0.0205 | 0.0434 | 0.0179 | |
| CV | 20.1261 | 8.1553 | 20.0565 | 8.0755 | 20.1261 | 8.1610 | 3.2848 | 1.3680 | |

-continued

| | | | | | | | | | |
|---|---|---|---|---|---|---|---|---|---|
| Mean | 0.3357 | 0.3499 | 0.2761 | 0.2787 | 0.3356 | 0.3498 | 1.2299 | 1.2203 | 1–4 |
| SD | 0.0620 | 0.0277 | 0.0509 | 0.0226 | 0.0620 | 0.0277 | 0.0369 | 0.0163 | |
| CV | 18.4633 | 7.9080 | 18.4207 | 7.8579 | 18.4642 | 7.9137 | 2.9977 | 1.3394 | |
| Mean | 1.2417 | 1.2378 | 1.5355 | 1.5308 | 1.2418 | 1.2380 | 0.9551 | 0.9554 | 2–4 |
| SD | 0.0301 | 0.0260 | 0.0372 | 0.0323 | 0.0301 | 0.0261 | 0.0043 | 0.0043 | |
| CV | 2.4205 | 2.1026 | 2.4237 | 2.1115 | 2.4241 | 2.1065 | 0.4549 | 0.4535 | |

Patient B

| | hv1 | hv1* | hv2 | hv2* | hv3 | hv3* | hv4 | hv4* | Wavelength Ratio |
|---|---|---|---|---|---|---|---|---|---|
| Mean | 0.2986 | 0.2992 | 0.3391 | 0.3399 | 0.2985 | 0.2991 | 1.2938 | 1.2926 | 1–3 |
| SD | 0.0243 | 0.0111 | 0.0272 | 0.0137 | 0.0243 | 0.0111 | 0.0183 | 0.0143 | |
| CV | 8.1384 | 3.7115 | 8.0129 | 4.0221 | 8.1349 | 3.7087 | 1.4146 | 1.1091 | |
| Mean | 0.2587 | 0.2595 | 0.1459 | 0.1463 | 0.2586 | 0.2593 | 1.3405 | 1.3390 | 1–4 |
| SD | 0.0217 | 0.0106 | 0.0121 | 0.0066 | 0.0217 | 0.0106 | 0.0209 | 0.0179 | |
| CV | 8.4011 | 4.0954 | 8.2977 | 4.5419 | 8.3992 | 4.0950 | 1.5586 | 1.3346 | |
| Mean | 0.8367 | 0.8375 | 1.0921 | 1.0932 | 0.8365 | 0.8374 | 1.0449 | 1.0446 | 2–4 |
| SD | 0.0120 | 0.0108 | 0.0159 | 0.0148 | 0.0120 | 0.0108 | 0.0044 | 0.0041 | |
| CV | 1.4333 | 1.2900 | 1.4604 | 1.3564 | 1.4386 | 1.2951 | 0.4179 | 0.3905 | |

Figure 17:
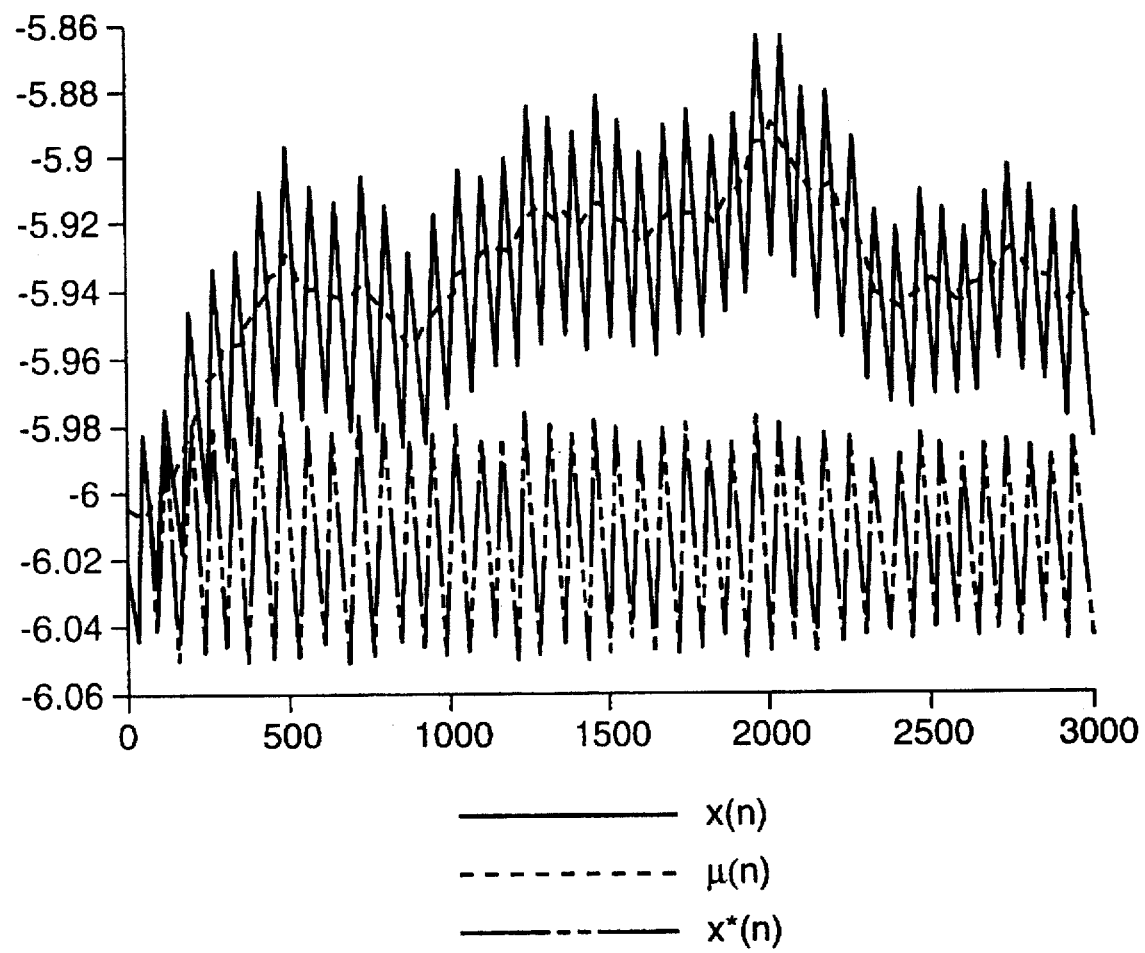
FIG. 17 is a graph showing the original, detrended and DC signals.

The plot shown in FIG. 17 shows the three relevant signals for a typical case. The original signal x(n) is shown by a solid line, the MA filtered signal μ(n) shown by a dashed line, and the de-trended signal x*(n) shown by a dot-dashed line. In FIG. 17, the de-trended signal x*(n) has been offset so that the three graphs can be shown on the same page. It shall be understood, however, that the de-trended signal is zero-mean.

Adaptive Peak and Valley Detector

Once the sampling of each channel is complete and the raw data is stored and detrended, the present invention processes the captured data to estimate hematocrit and other characteristics of interest. The preferred method used to determine the correlation between absorbed light and hematocrit is the ratio of the photoplethysmographic values at the peak and valley for an individual heartbeat. An exemplary photoplethysmograph 210 is shown in the upper portion of FIG. 18. One full heartbeat is indicated by reference numeral 208. It is very important that the actual peaks, such as peak 204, of the waveform 210 are detected and the false peaks due to noise and the dichrotic notch 206 are ignored. A dichrotic notch 206 is created by the closure of the aortic valve and can be more pronounced in some individuals. In some individuals, the dichrotic notch is very weak during sampling. The present invention provides a real time adaptive peak and valley filter which determines the actual peaks 204 and valleys 202 of the waveform 210 while filtering out any false peaks and valleys. This is an important feature of the present invention as the underlying pulsatile signal, and hence the associated peaks and valleys, are highly variable and potentially non-periodic.

Figure 18:
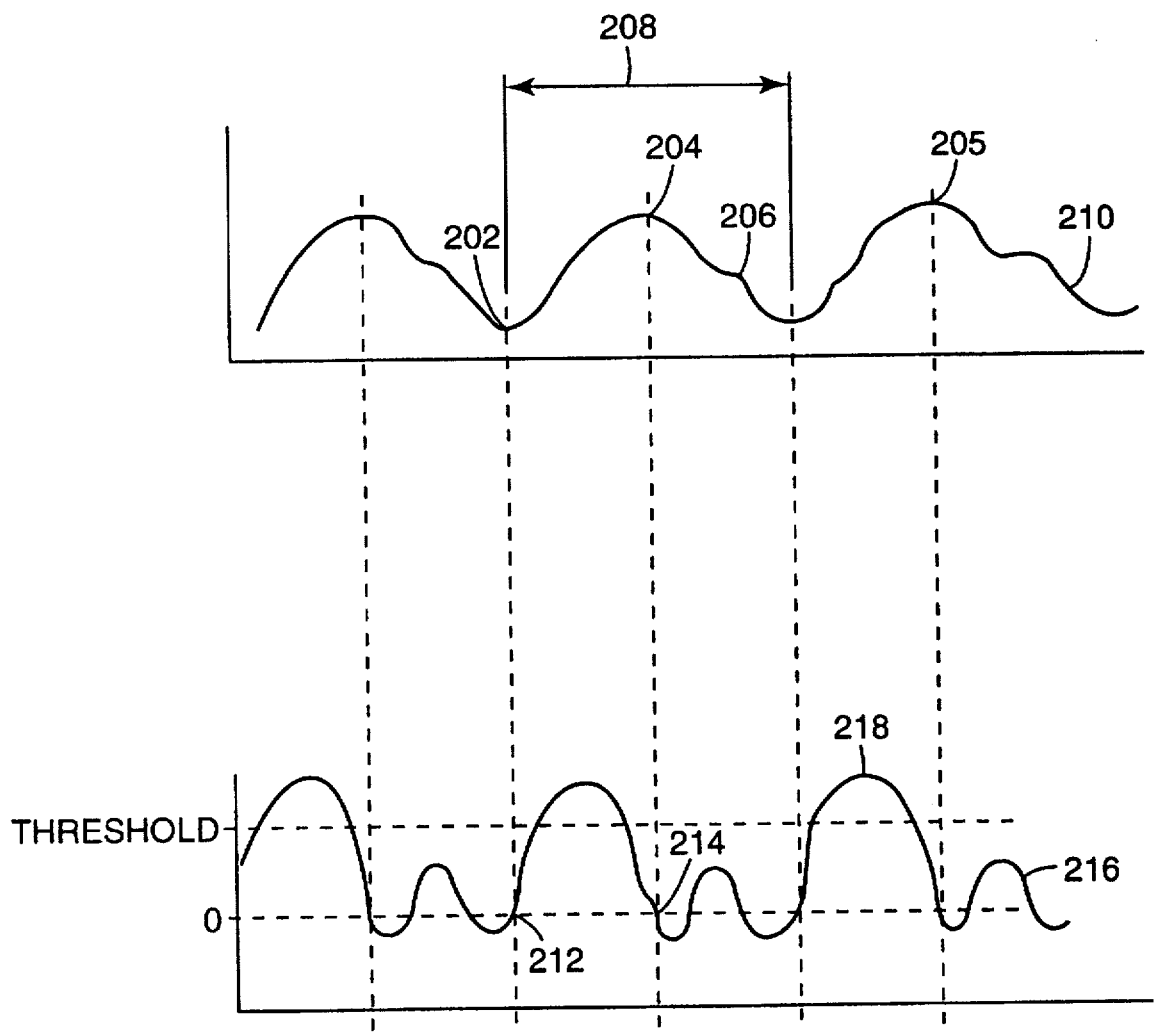
FIG. 18 shows an exemplary photoplethysmographic waveform and an associated differentiated photoplethysmographic waveform.
Figure 19A:
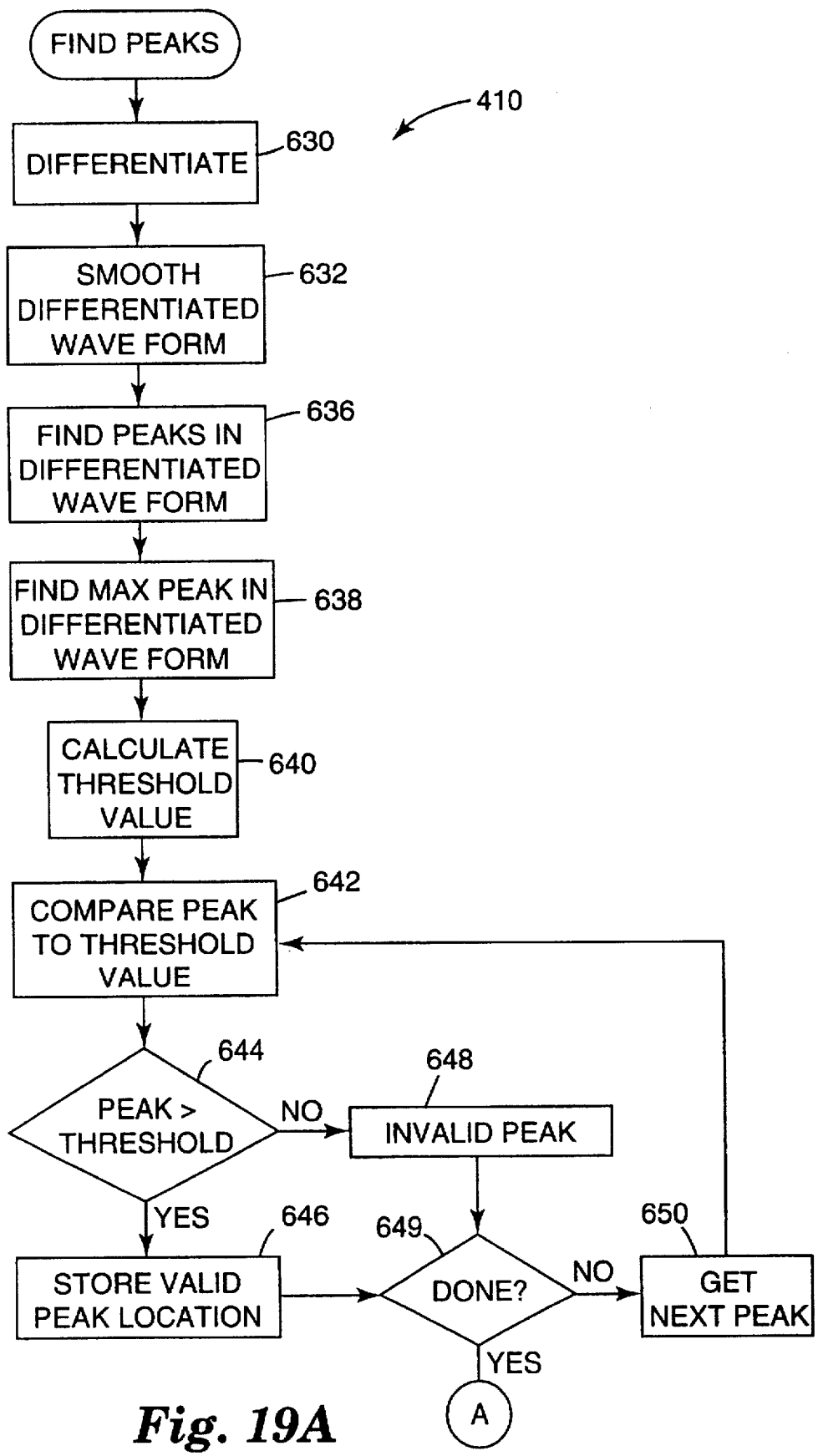
FIGS. 19A and 19B show the procedure for finding actual peak and valley locations.

FIG. 19A shows the process 410 by which the actual peaks and valleys are found. First, the sampled waveform is differentiated. An exemplary differentiated photoplethysmographic waveform 216 is shown in the lower portion of FIG. 18. An 11 tap smoothing filter is applied to the differential waveform at block 632. Next, all peaks in the differentiated waveform are found, and the value of the maximum peak in the differentiated waveform, peak 218 in FIG. 18, is determined at block 638. A threshold value is calculated for comparison purposes at block 640. In the preferred embodiment, the threshold value is 50% of the value of the maximum peak 218 in the differentiated waveform. This threshold value is also shown on the differentiated waveform in FIG. 18. Valid peaks in the differentiated waveform are determined from invalid peaks in the differentiated waveform by comparing the actual value of each peak with that of the threshold value at block 642. If the peak in question has a value less than that of the threshold value at block 644, that peak is determined to be due to noise or the diacrotic notch and is therefore an invalid peak at block 648. Any peak that is determined to be part of an incomplete pulse is also as designated invalid to avoid false peaks. If the peak in question has a value at block 644 greater than the threshold value, that peak is a valid peak at block 646.

Figure 19B:
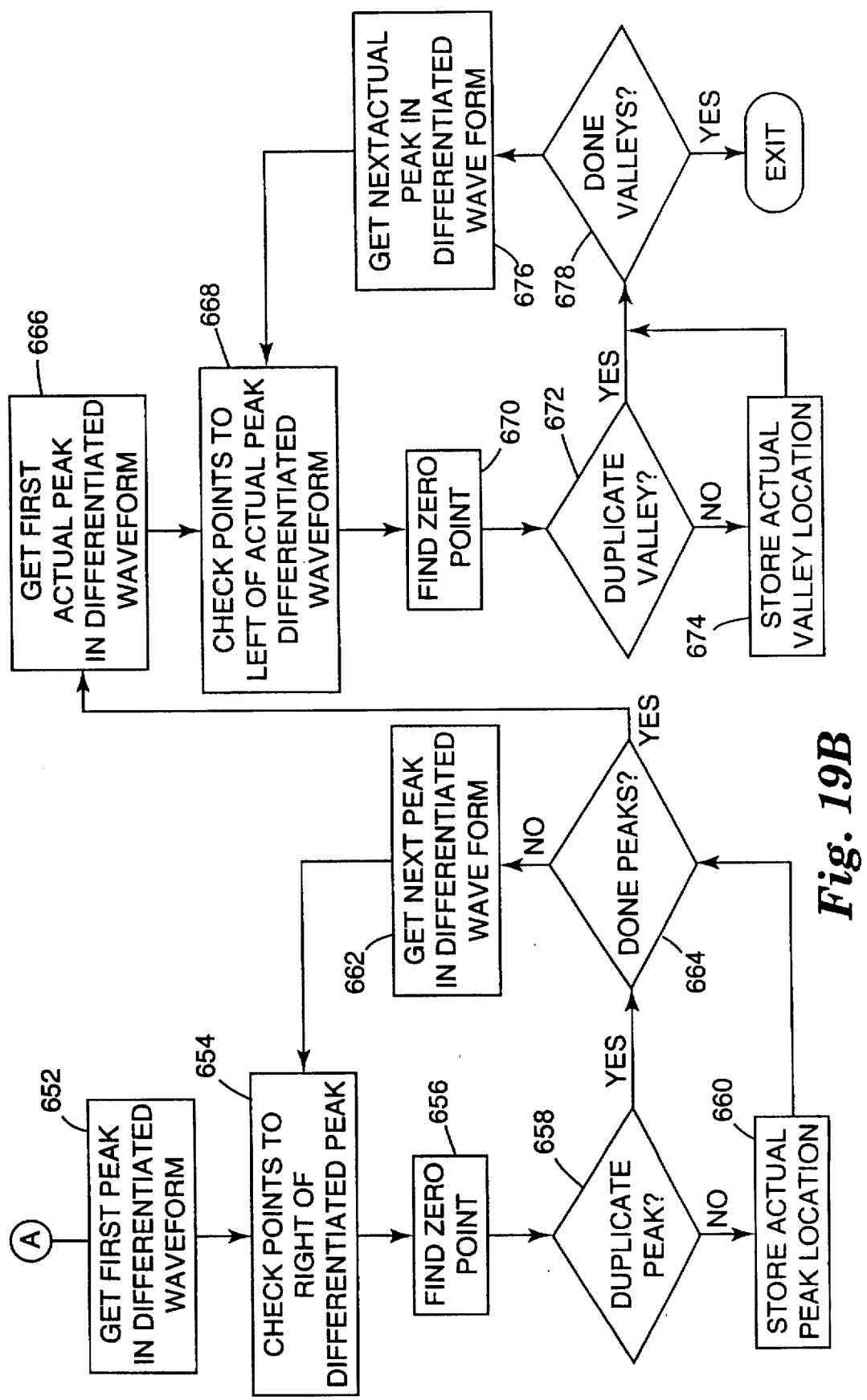

After determining valid peaks in the differentiated waveform at block 649, the actual peaks and valleys for the original waveform are determined as shown in FIG. 19B. The differentiated waveform is scanned looking for points at which the differentiated waveform amplitude equals zero, such as point 214 in FIG. 18. This corresponds to the point where the slope of the actual waveform equals zero, thus, the location of an actual peak or a valley. The process starts at a peak in the differentiated waveform at block 652, for example, peak 218 in FIG. 18, and examines data points to the right of this peak at block 654. The zero crossing point is determined to be the data point at which an actual peak at block 656, 205 in the example of FIG. 18, occurs. If this point has been already found from previous peak candidates the duplicate peak is discarded at block 658. Otherwise, the location of the actual peak is stored in a one dimensional array 220 at block 660 such as that shown in FIG. 13B. This process is continued for all candidate peaks through blocks 664 and 662.

The right portion of FIG. 19B shows the process by which valid valley locations are found. After all peaks are tested, the valleys are found by scanning to the left of a determined peak at blocks 666 and 668 (such as peak 204 in FIG. 18) in the differentiated waveform for the zero crossing point at block 670 (point 212 in FIG. 18). This zero crossing point is determined to be a valley (valley 202 in FIG. 18), and this valley location is also saved for further calculations at block 674. The process continues through blocks 678 and 676 for all candidate valleys.

Figure 13B:
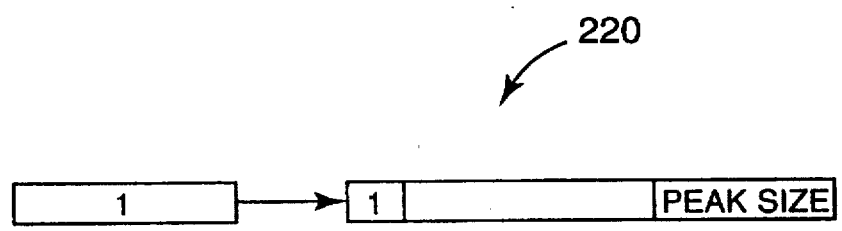

The locations of all valid peaks for each wavelength of interest are stored in a one-dimensional array such as that shown in FIG. 13B. The number of elements in this array is equal to the maximum number of valid peaks (100 in the preferred embodiment) which can be stored. The location of each actual peak is stored in the array. For example, if a peak is determined to exist at the 23rd and 60th data point, the array would contain 23 and 60. The same is true for each valley found. If a valley is determined to be at the 19th and 48th data points, then a similar array for storing valley locations would contain 19 and 48, etc.

Peak and Valley Value Determination

Once the location of the peaks and valleys is determined and stored, the voltage values or amplitude of the peaks and valleys are determined.

For each wavelength band there is a time dependent voltage level corresponding to the energy received in that band. The correlation between voltage value and location is maintained in the array where the raw data is stored.

Where the signal levels are relatively high, i.e., a high signal to noise ratio (SNR), a direct reading of the raw data of the voltage value of a peak or valley of a particular location can be confidently made. Due to differences in absorption and, scattering for the various wavelengths, however, the pulsatile signals for some channels have weaker signal to noise ratios than others. The underlying signals in the absence of noise all have the same underlying shape, since each channel will yield a photoplethysmograph having the characteristic shape of the pumping and flowing bloodstream. The only difference between signals for different channels is their pulsatile amplitude and DC offset. It is this amplitude and DC offset that are critical to the accurate measurement of hematocrit. However, on low SNR signals the peak and valley values contain significant noise and this inaccuracy leads to error in the hematocrit calculation. The present invention therefore provides a technique for improving the measurement of amplitude of the peaks and valleys for channels with low SNRs. This technique is called "template matching" and is shown in FIG. 20.

Figure 20:
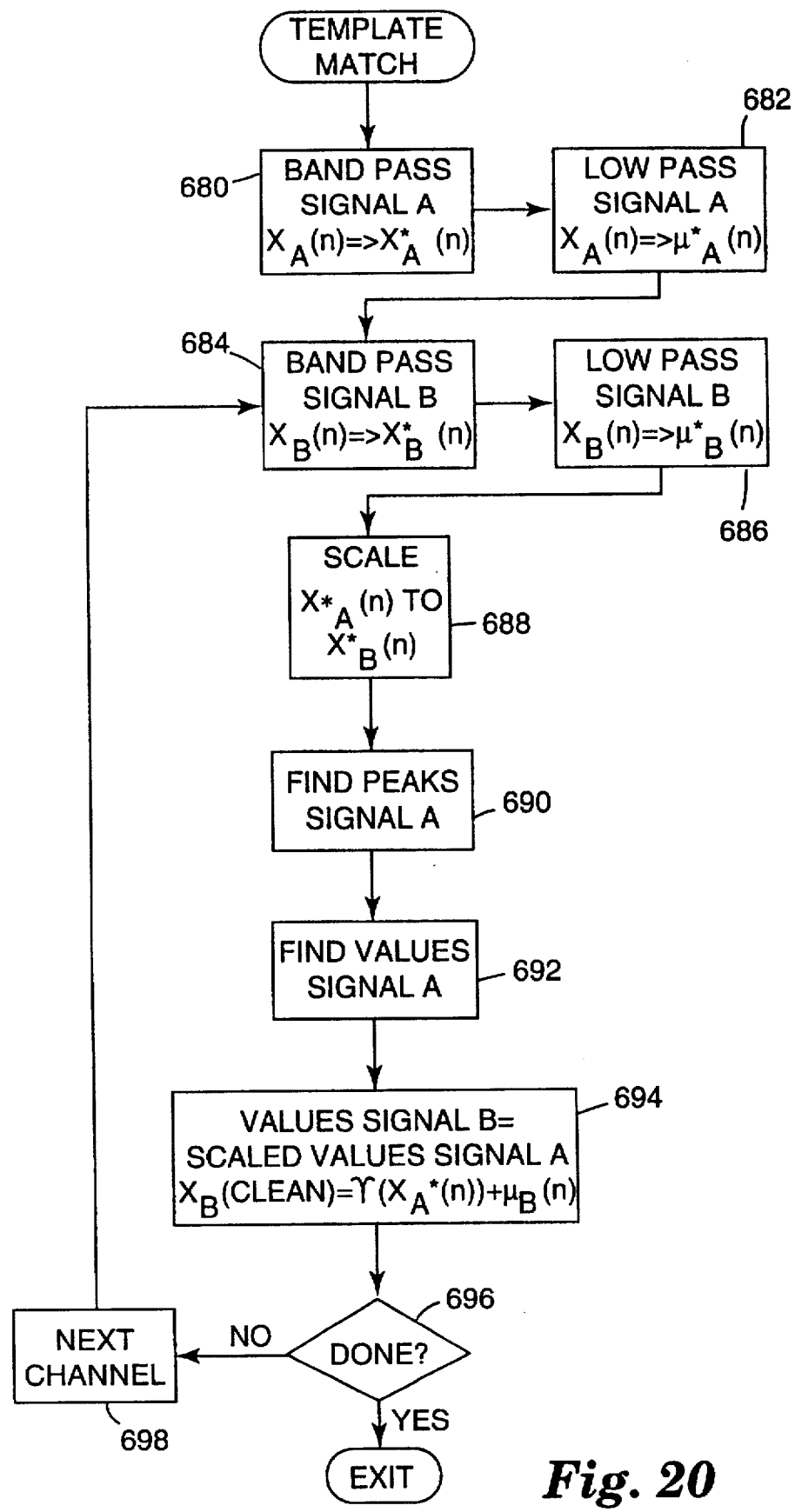
FIG. 20 shows the procedure for finding the the values associated with peak and valley.

FIG. 20 shows the present template matching technique 412 for finding the values of peaks and valleys at low SNRs. In the preferred embodiment, the user is able to select whether template matching should be performed on a channel by channel basis.

For example, if the peak to peak voltages of the user selected channels falls below the specified threshold, the user may infer that template matching may be appropriate.

The present template matching technique 412 has the advantage that peak and valley voltage measurement need only be performed on the wavelength with the highest SNR (in the preferred embodiment, this is most typically the isosbestic channel, corresponding to a wavelength in the range 800–840 nm). The high SNR wavelength is scaled to determine the values of peaks and valleys at wavelengths having low SNRs.

Figure 21A:
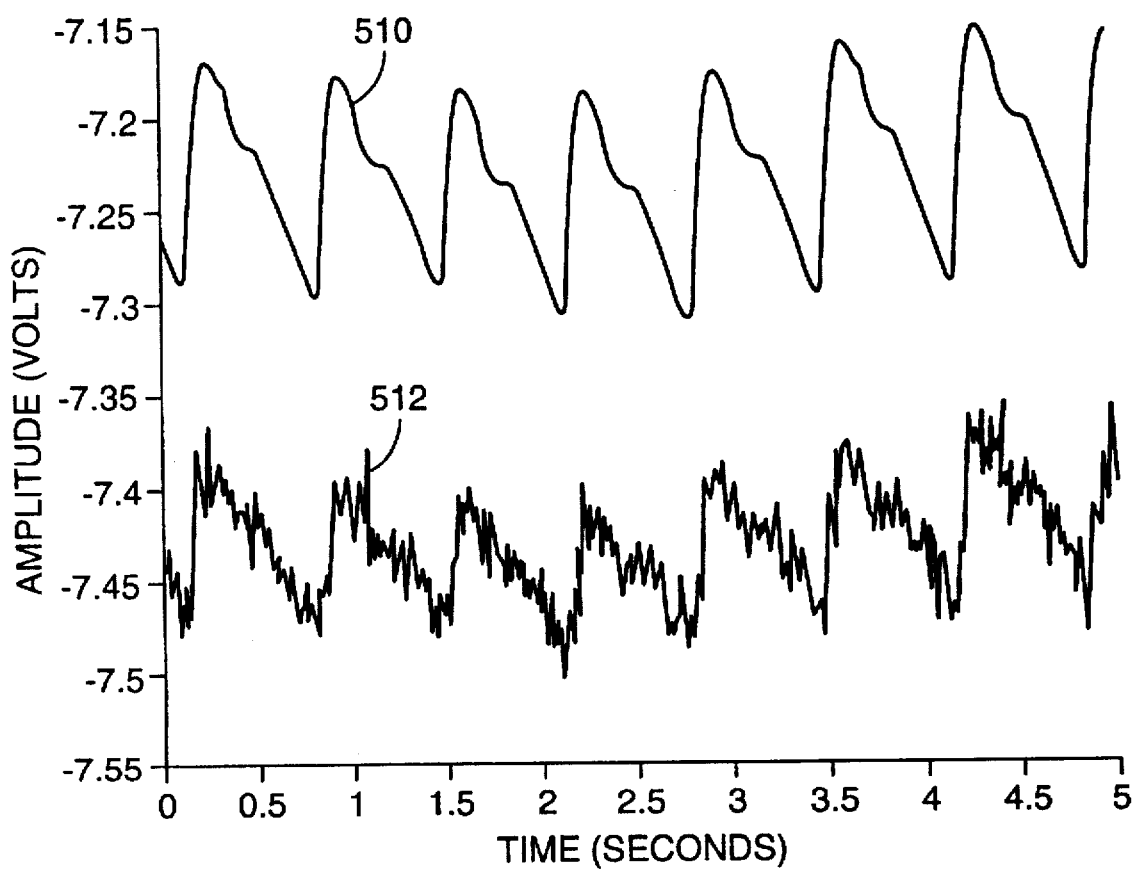

For purposes of illustration and the processing steps shown in FIG. 20, assume channel A is the high SNR signal and channel B is a low SNR signal. Exemplary waveforms of signal A and signal B are shown as waveforms 510 and 512, respectively, in FIG. 21A. The first step is to band pass both signal A in block 680 and signal B in block 684. The band passed waveforms of signal A and signal B are shown in FIG. 21B as waveforms 518 and 520, respectively. The linear phase band pass filter removes the DC offset, rejects high frequency noise and detrends the signals such that only the AC or pulsatile portion of the waveform remains.

Figure 21C:
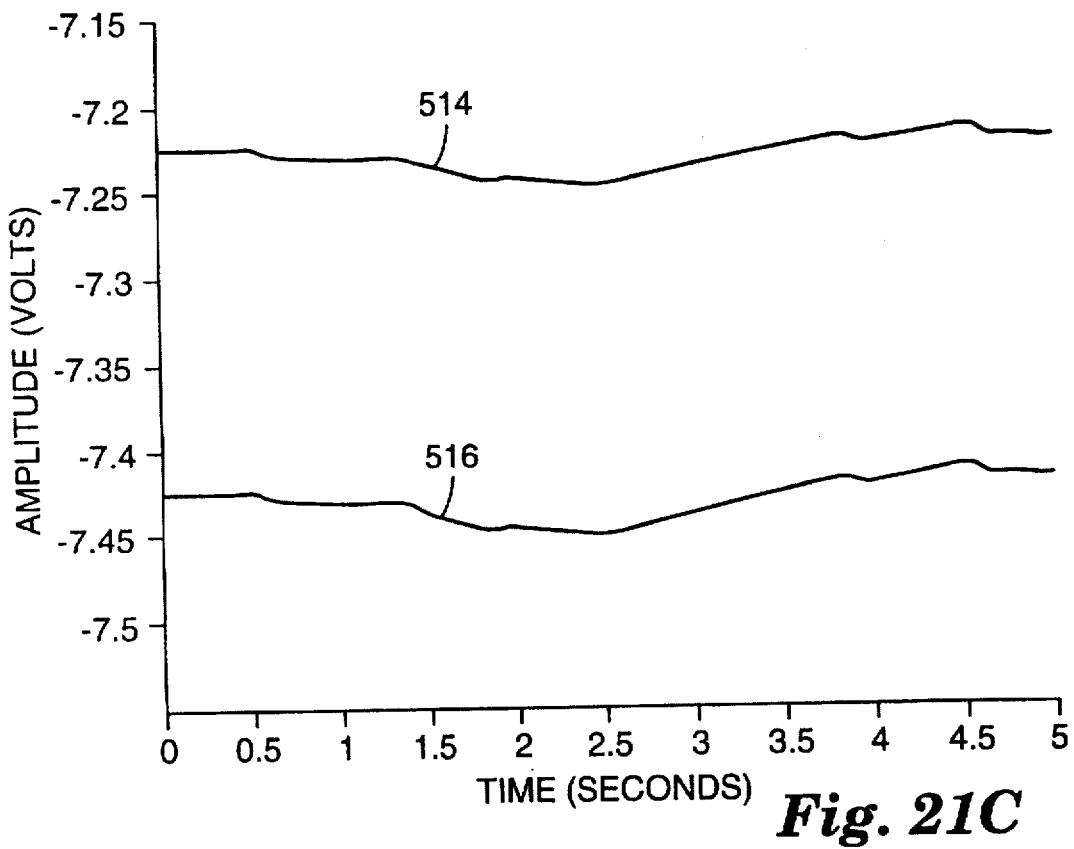

Both signal A and signal B are also low pass filtered in blocks 682 and 686, respectively. The low passed waveforms of signal A and signal B are shown in FIG. 21C as waveforms 514 and 516, respectively. The low pass filter rejects the AC component and passes the DC offset and any trend or low frequency noise such as respiratory artifact. The signal $\mu(n)$ described above with respect to FIG. 16 can be used for the low passed signal.

Next, a least square fit between band passed signal A and band passed signal B is calculated. This consists of scaling band passed signal A such that it is the best match for band passed signal B in the least square sense at block 688. As previously stated, the signals for all channels of interest have the same underlying pulsatile waveform. The least square fit approach of the present invention simply exploits this fact. The advantage is that the location and amplitudes of the peaks and valleys need only be performed on the highest SNR signal at blocks 690 and 692. The amplitudes of the peaks and valleys for the lower SNR signals are found by scaling the high SNR peaks and valleys with the scale factor from the least square fit optimization.

In the preferred embodiment, the scale factor is calculated in a block fashion. The block approach operates on signals that are segmented into blocks of data or vectors, as follows:

Let $x_A(n)$=high SNR signal;

$x_B(n)$=low SNR signal;

$x^*_A(n)$=band passed high SNR signal;

$x^*_B(n)$=band passed low SNR signal;

$\mu_A(n)$=low passed high SNR signal;

$\mu_B(n)$=low passed low SNR signal; and $\gamma$=scale factor, where $x^*_A(n) = x_A(n) - \mu_A(n)$.

The least square minimization is defined as $$\min_\gamma \| x^*_B(n) - \gamma x^*_A(n) \|^2$$

and the solution is given by $$\gamma = \frac{x^{*+}_A(n) x^*_B(n)}{x^{*+}_A(n) x^*_A(n)}$$

where $x^{*+}_A(n)$ and $x^{*+}_B(n)$ are the transpose of $x^*_A(n)$ and $x^*_B(n)$, respectively.

The "clean" or noise reduced version of $X_B(n)$ at block 694 then becomes $$\begin{aligned} x_{B(clean)} &= \gamma(x_A(n) - \mu_A(n)) + \mu_B(n) \\ &= \gamma(x^*_A(n)) + \mu_B \times (n) \end{aligned}$$

Figure 21D:
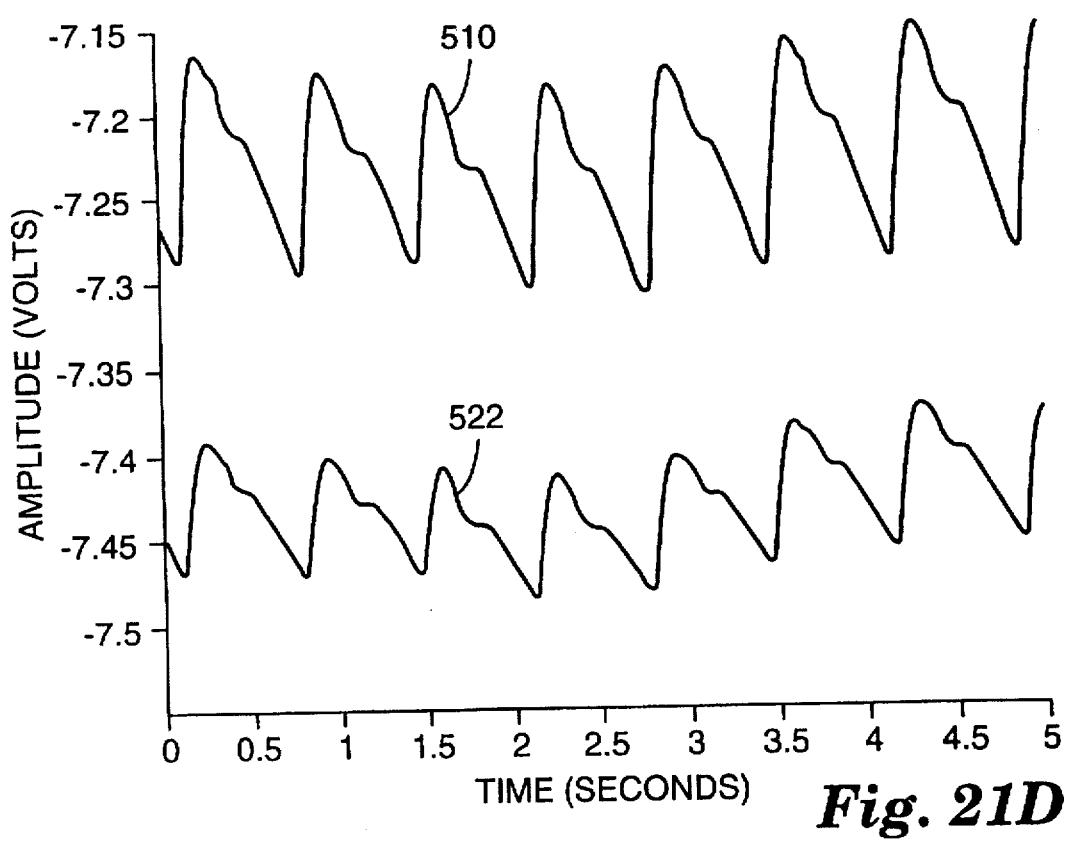

FIG. 21D shows the "clean" version of signal B as waveform 522.

Note that the clean version of $x_B(n)$ is a linear (affine) transformation of $x_A(n)$. Therefore, the peaks and valleys of the noisy vector $x_B(n)$ can be calculated from the peaks and valleys of the clean vector $x_A(n)$. In a multichannel system, this means that the peaks and valleys (both location and amplitude) need only be calculated for the channel with highest SNR (typically the isosbestic channel). The values of the peaks and valleys for those channels having low SNRs can be calculated using the above affine transformation.

Although the preferred embodiment is described as calculating the scale factor in block fashion, it shall be understood that the scale factor could also be calculated in many other ways, such as by recursion, without departing from the scope of the present invention.

In practice, there are several options for adding the low pass filtered signals $\mu_A$ and $\mu_B$ back into the AC pulsatile signals before calculating hematocrit. In the simplest case, the low pass signals may be added back to the AC signal without further processing. If the baseline value drifts considerably during a pulse, the baseline waveform could be set to the average value during that pulse. This would produce a stair-step DC waveform if considerable drift was present.

In U.S. Pat. No. 4,869,254, the equivalent DC value is set to either a peak or valley value of the unfiltered waveform. Then a peak or a valley value is adjusted to correspond to the DC shift. This is an alternative approach.

Determination of Prediction Equation

Using the MAXR statistical analysis method described above, and selecting from the Preferred Range of wavelengths described above in Table 1, and using either HV1 or HV2, the following equations can be used alternatively in the direct prediction of hematocrit of humans, noninvasively and transcutaneously:

$$HCT = 55.3(HV1_{1207,660}) - 563(HV1_{1302,805}) + 596(HV1_{1302,910}) - 58(HV1_{837,805}) + 93.2$$

Figure 22:
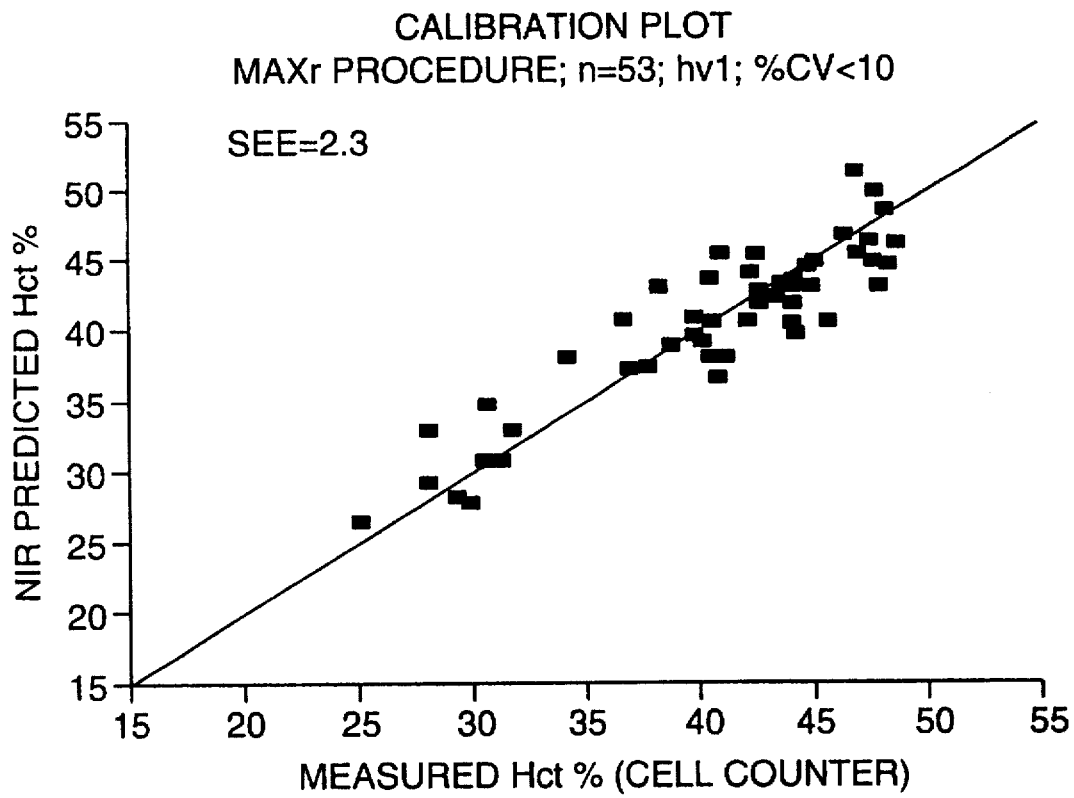
FIG. 22 is a calibration plot of results using a first equation used according to the present invention for the direct prediction of hematocrit compared with actual hematocrit.
Figure 23:
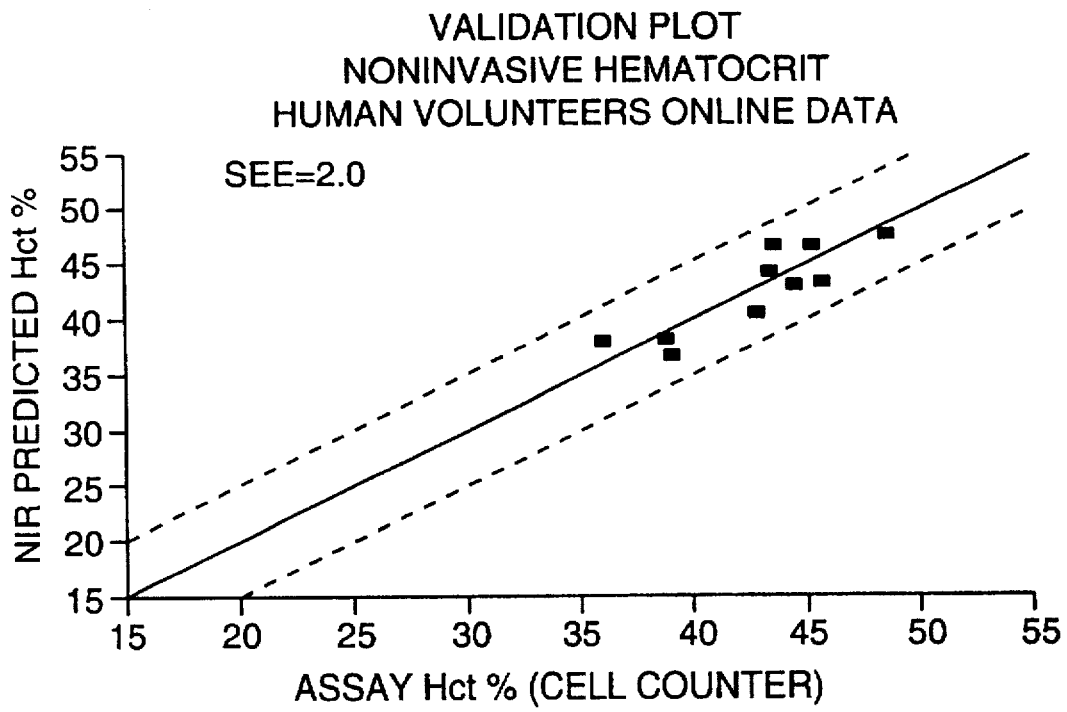
FIG. 23 is a validation plot of results using the first equation.

This equation was developed using data collected from about 53 healthy individuals, chronic renal failure patients, and postoperative patients to form the training set. FIG. 22 shows a calibration plot with an $R^2 = 0.83$ and all hematocrit values within +/-5 hematocrit percent. To validate this prediction equation, the hematocrit of 10 new individuals was predicted noninvasively and transcutaneously using the apparatus and method described above. The prediction equation for these 10 individuals was plotted and is shown as FIG. 23. All prediction points fell within +/-3 hematocrit percent.

Figure 24A:
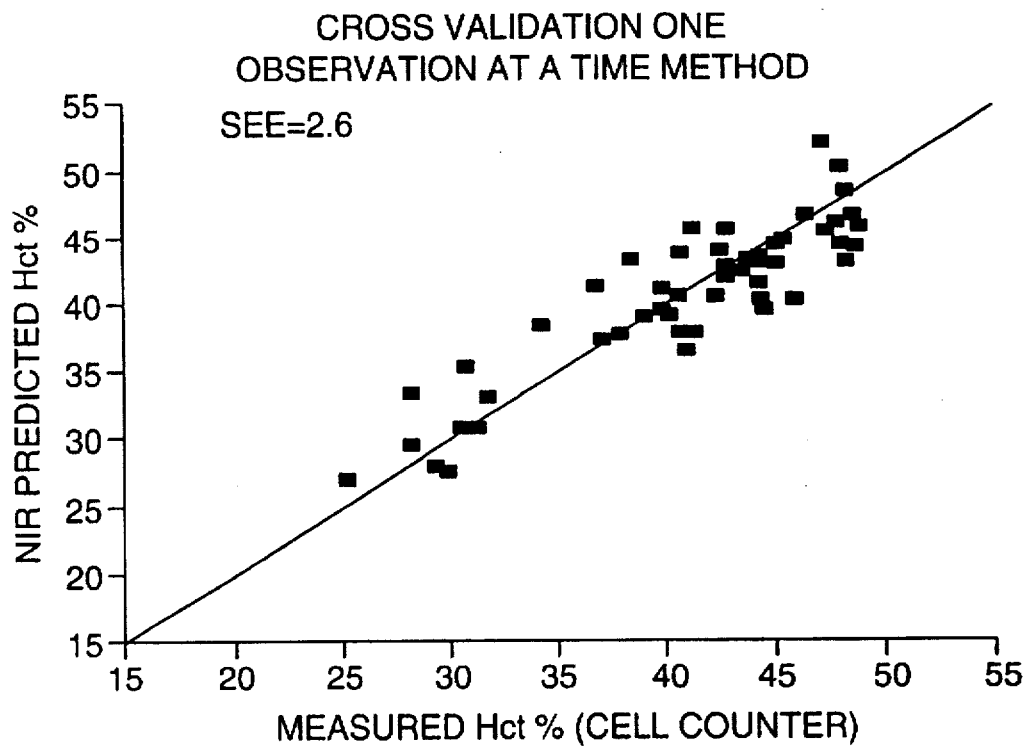
FIGS. 24A and 24B are a cross validation plot of results using the first equation.
Figure 24B:
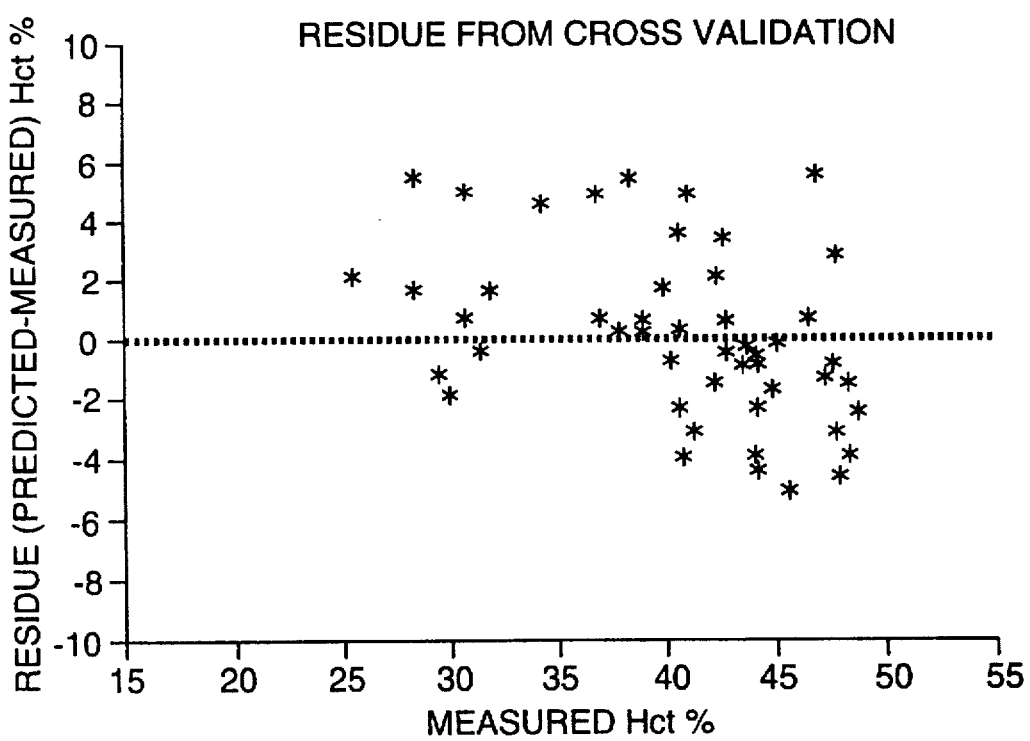

Another technique of validating the prior equation of FIG. 22 is to use a statistical program that removes one datum and predicts its value based on a regression equation derived from the remaining data points. This procedure is repeated for all data points in the set. The results are shown in FIGS. 24A and 24B.

The following equation below used the apparatus and method described above, HV2, MAXR, and the most preferred set of wavelengths: 660, 805, 820, 910, 972, 1100, 1195, and 1300 nm.

$$HCT = -54.85(HV2_{1300,1100}) - 34.72(HV2_{1195,972}) + 26.38(HV2_{1195,660}) - 7.418(HV2_{972,660}) + 3.105(HV2_{1100,910}) + 71.03$$

Figure 25:
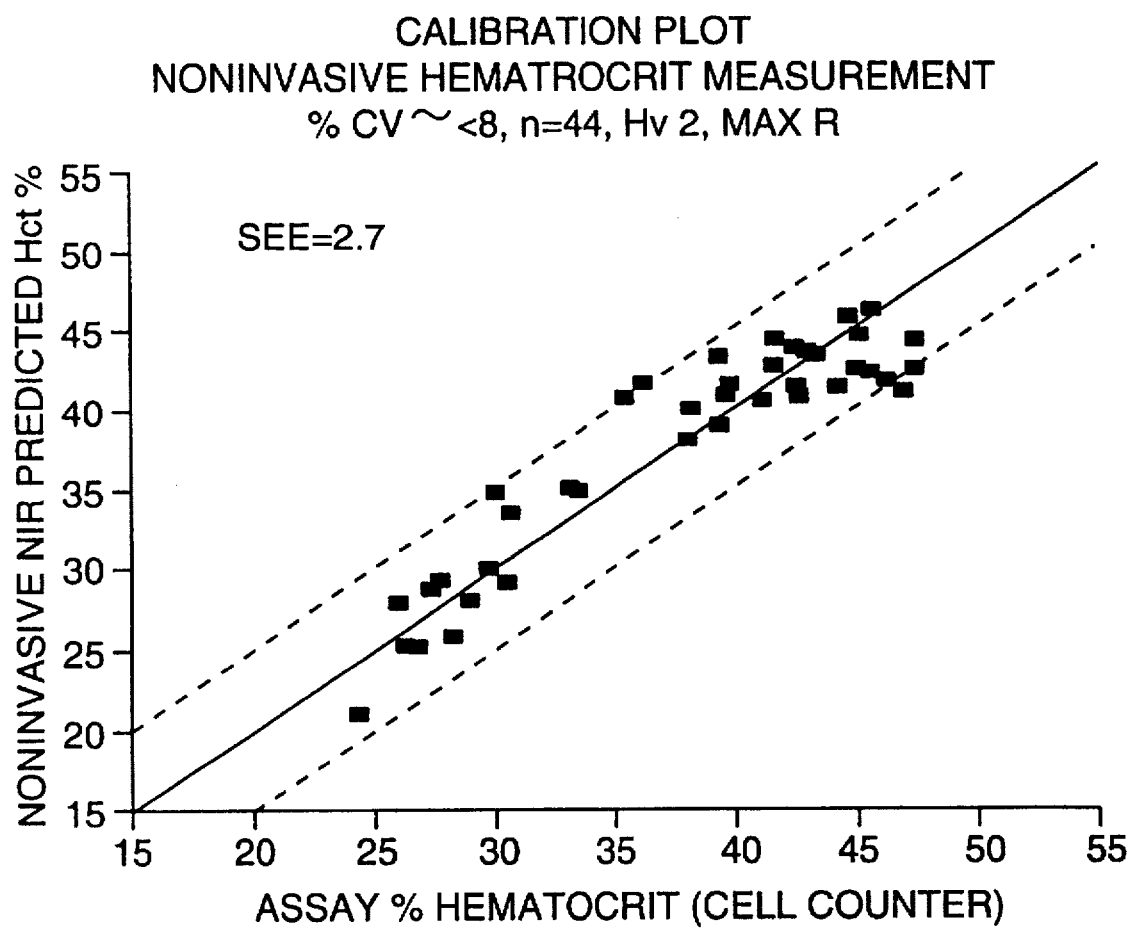
FIG. 25 is a calibration plot of results using a second equation used according to the present invention.
Figure 26:
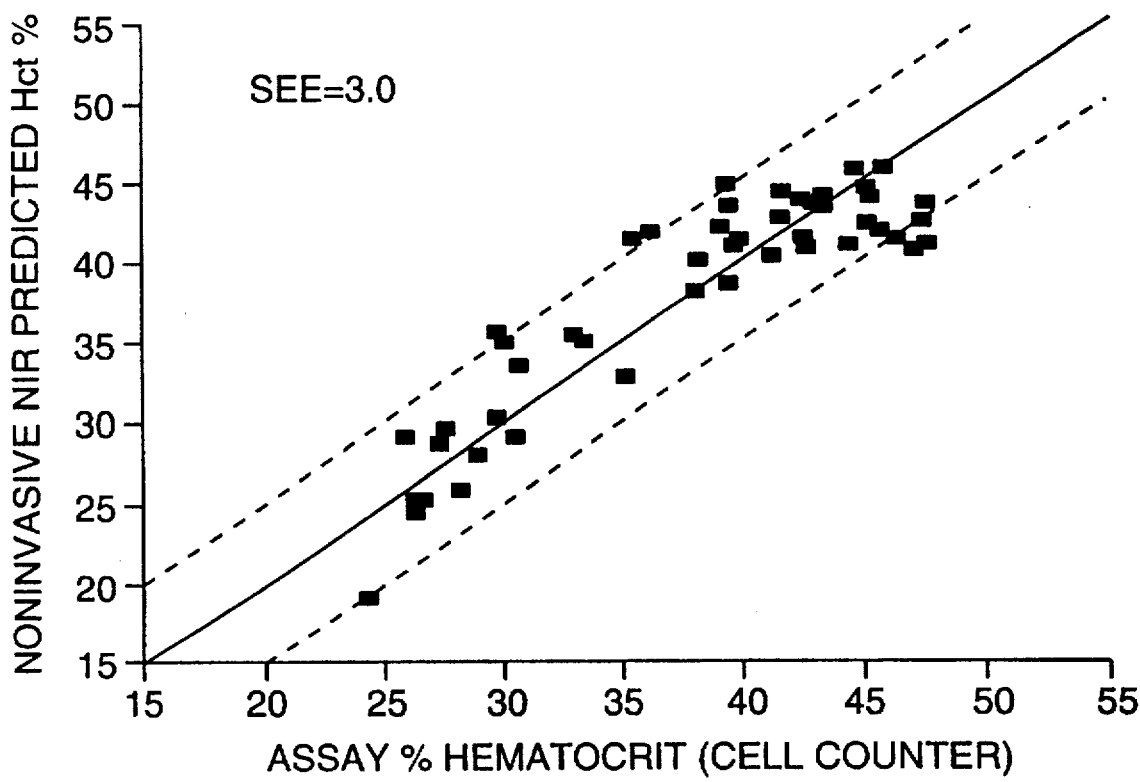
FIG. 26 is cross validation plot of results using the second equation.
Figure 27:
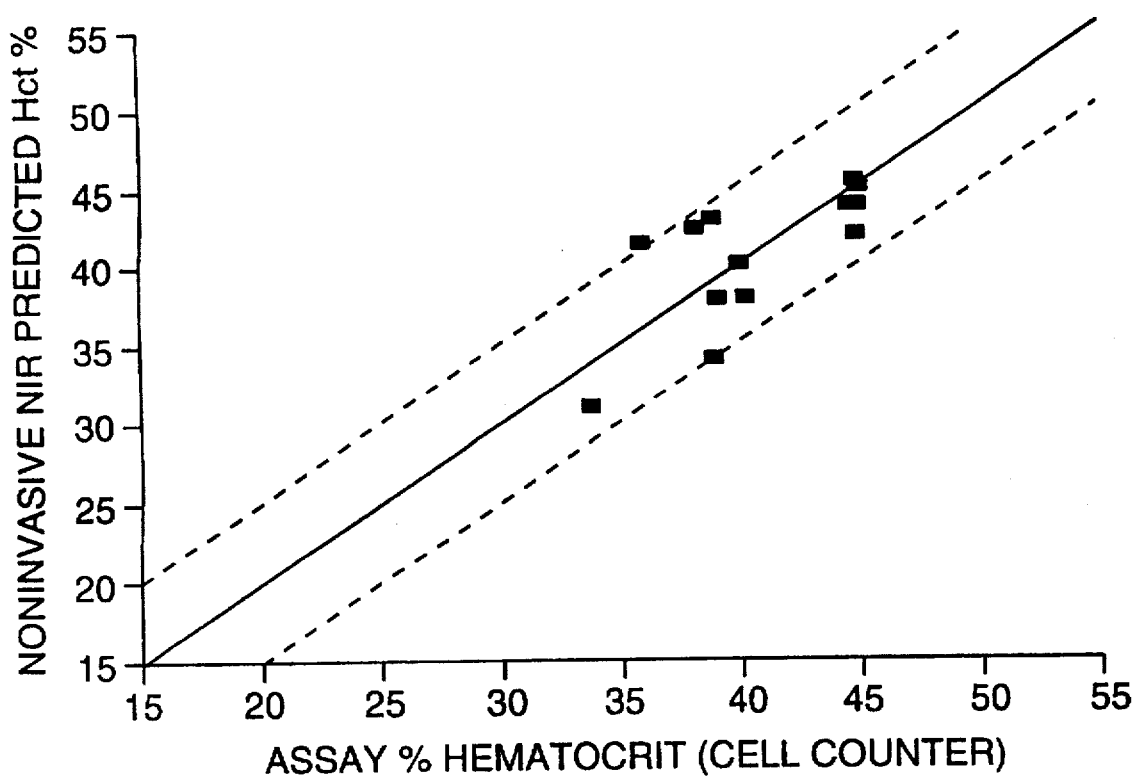
FIG. 27 is a validation plot of results using the second equation.

A complete calibration/validation sequence was run, using about 40 healthy volunteers and 25 chronic renal failure patients to provide a wider range of actual and training hematocrit values to establish the training set. FIG. 25 shows the calibration plot using the above equation with an $R^2$ of 0.85 and virtually all hematocrit values within +/-5 hematocrit percent. This equation was validated using the cross-validation, one point at a time method, which gave a prediction plot seen in FIG. 26 with an $R^2$ of 0.80 and only a slight increase in the spread of hematocrit values. FIG. 27 shows the results of an on line prediction performed by programming the coefficients of the above equation into the computer. Volunteer human subjects' photoplethysmographs were recorded and individual hematocrit values were displayed and recorded "online". As usual, venous blood samples withdrawn from the subjects were analyzed with a cell counter reference method. The results are displayed in FIG. 26.

Once the prediction equation is established, the geometry of the device shown in FIG. 4 needs to remain fixed. Alteration of the device requires recalculation of the prediction equation.

The sensitivity of the above is dependent upon changes in individual H Values, shown in the sensitivity equation below.

$$Sensitivity = [-54.85 - 34.72 + 26.38 - 7.418 - 3.105]^T$$

e.g., a change of 10% in $HV2_{1300,1100}$ results in a change of 3 HCT %.

Figure 28:
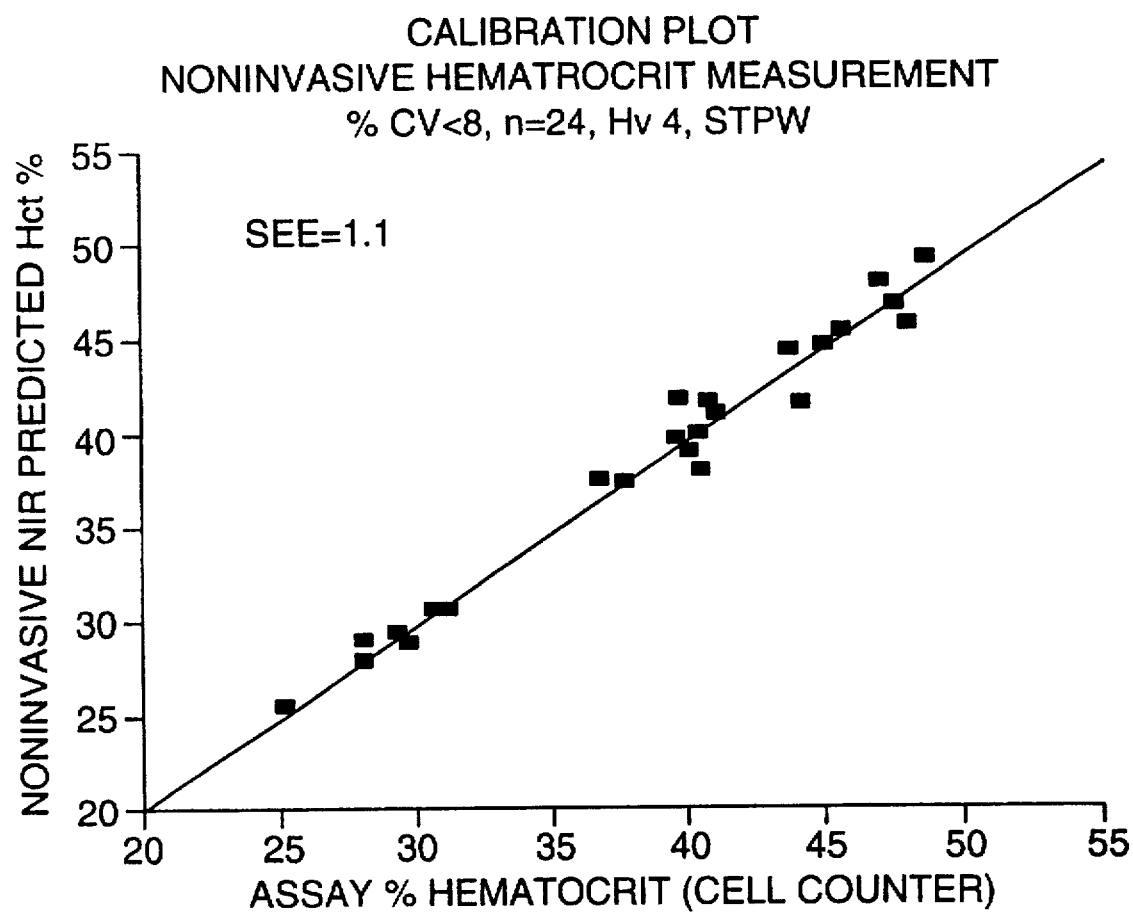
FIG. 28 is a calibration plot of results using a third equation used according to the present invention.

Another example of a calibration plot is shown in FIG. 28. Data was taken on subjects and the data set reduced to include those with H Values corresponding to a H Value Coefficient of Variation of less than 8 percent. Statistical analysis using a stepwise regression was used, resulting in the following multiple wavelength calibration equation shown below with $R^2 = 0.97$.

$$HCT = -126(HV4_{805,660}) - 573(HV4_{1302,680}) - 1366(HV4_{1302,837}) +$$
$$1966(HV4_{1302,805}) - 643(HV4_{680,837}) - 1209(HV4_{837,910}) +$$
$$2297(HV4_{805,910}) - 123(HV4_{978,680}) - 259(HV4_{805,905}) + 1483.$$

It is understood that although nine wavelength ratios are used, a correlation coefficient $R^2$ of about 0.9 can obtained with only four of the nine ratios, i.e., the ratios vary in their contribution to the final correlation coefficient.

It is also understood that a cross validation of this equation may not produce hematocrit predictions of satisfactory accuracy because the small number sample of data points do not adequately represent the population. Nevertheless, this equation shows that data collected over a larger population with care to provide a low H Value coefficient of variation should provide a hematocrit prediction with low error.

Yet another example of a calibration equation was obtained with a data sample of a percent H Value Coefficient of Variation of less than 8, n (number of data points)=24, and $R^2 = 0.92$, utilizing the MAXR procedure to produce the following equation.

$$HCT = -17.6(HV1_{1163,820}) - 166(HV2_{820,910}) + 22(HV2_{1302,805}) + 50.4(HV2_{805,910}) + 15.2(HV2_{978,680}) + 22.$$

Determination of Confidence Level Calculation of Coefficient of Variation

Once the hematocrit is predicted, a measure of the level of confidence of the prediction is desired. The reason for this is that there is uncertainty in the calculation. This variability, while ignored in many devices, can be used to indicate the confidence of the measurement.

One such method of estimating the confidence is to compute the distribution of a measured parameter about the mean a measured parameter. As an example, assume the measure of parameter measurement is normally distributed about the mean (v) with a standard deviation ($\sigma$). This is given by:

$$N(v,\sigma) = e^{-(x-v)^2/(2\sigma^2)}$$

$$\text{where } v = \frac{1}{n} \sum_{i=1}^{n} HV[i]$$

$$\text{and } \sigma = \left\{ 1/n \sum_{i=1}^{n} (HV[i] - v)^2 \right\}^{0.5}$$

Assuming a distribution about a central value, a valuable measure of the distribution of data about that value is the standard deviation ($\sigma$) or the standard deviation normalized to the mean and converted to a percentage, assuming a normal distribution. When the standard deviation is normalized to the mean the measurement is called the coefficient of variation (CV). The CV is computed as follows:

$$CV = \frac{\sigma}{v} \times 100\%$$

The CV provides an average of the measured parameter and number indicative of the distribution of the measured parameter about the average. For example, for a normal distribution, a CV=5% means that 68.27% of the measured parameter (the data +/−1 standard deviation) lie in a band +/−5% of the measured parameter value.

For purposes of the present invention, the CV of several different parameters are applicable. One is the coefficient of variation of one or more H Values used to predict hematocrit. The preferred H Value for coefficient of variation purposes corresponds to the ratio of an isosbestic wavelength and the upper water band. Since an isosbestic wavelength and the upper water band are typically the strongest and weakest signals, respectively, the corresponding H Value is preferred since that ratio will generally give the worst case coefficient of variation.

Another useful measure which can be used is the CV of hematocrit prediction.

The significance of this calculation is not limited to normal distributions of data and coefficient of variation. In fact, the distribution about the mean of the preferred H Value in the present invention is not a normal distribution. However, the calculated CV is nevertheless a reliable indicator of the confidence level of the hematocrit prediction.

The CV of the preferred H Value is displayed as shown in FIG. 28. If this CB exceeds the threshold specified by the user as described above with respect to FIG. 14, a "REJECT" message will be displayed. If the CV does not exceed the user specified threshold, an ACCEPT message, as shown in FIG. 14, is displayed. The displayed CV value, in combination with the ACCEPT or REJECT message and peak to peak voltages which are also displayed as described herein, allow the user to make a value judgment concerning the confidence of the hematocrit prediction.

Display of Waveforms and Results

The waveforms and computed results such as hematocrit, coefficient of variation, oxygen saturation, peak to peak voltages, etc. are displayed at control block 422 of FIG. 15.

Figure 29:
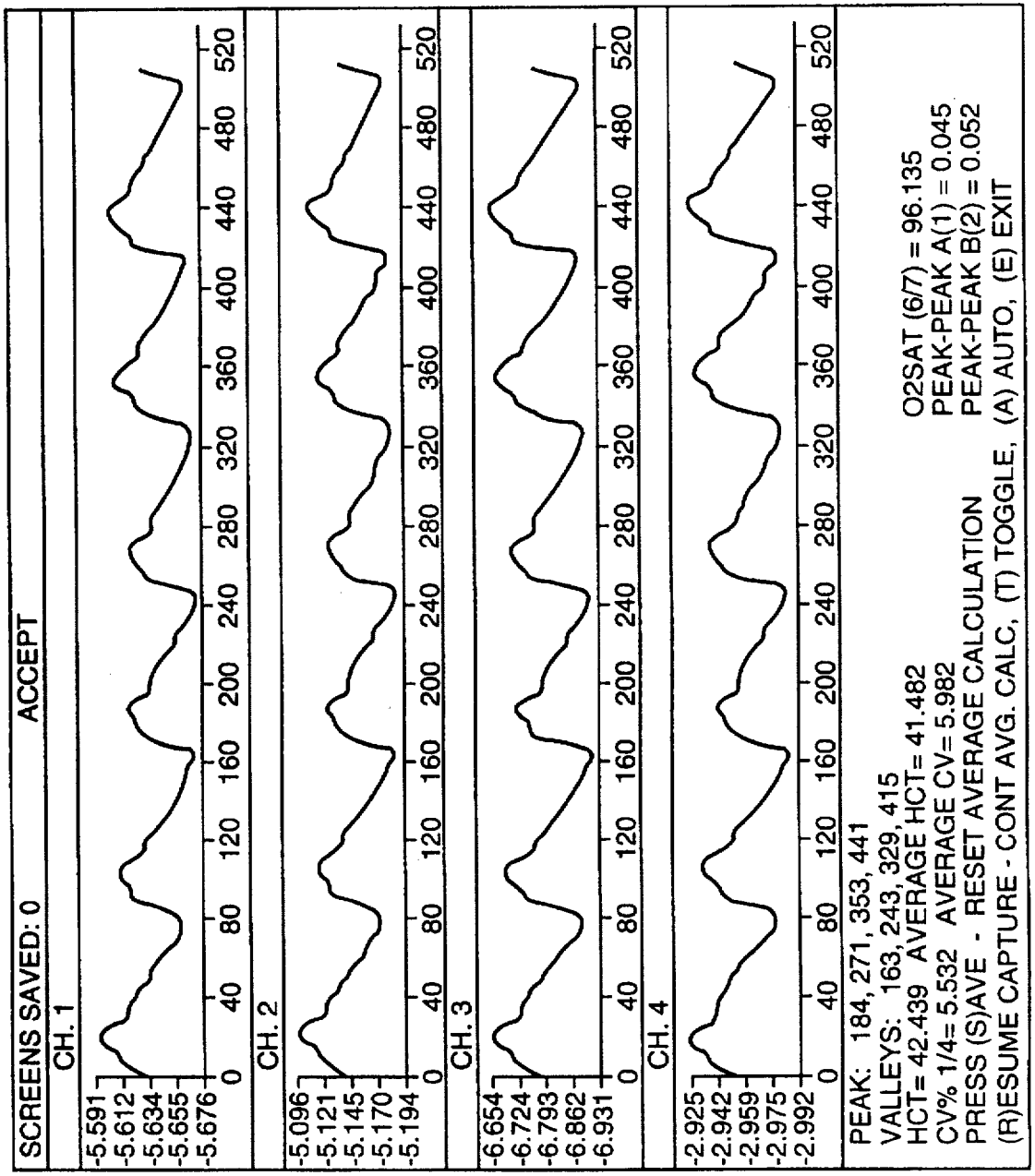
FIG. 29 shows an exemplary display screen of the present invention.

FIG. 29 shows an exemplary screen display of the apparatus of the present invention. The, display includes a plot of channels 1–4. The waveforms are plotted as amplitude (volts) vs. time (hundredths of seconds). Also displayed are the locations of the peaks and valleys, the hematocrit prediction (HCT) for the currently displayed screen, the average hematocrit over all screens obtained, the coefficient of variation of the preferred H Value ($HV_{1,4}$ in FIG. 28). The oxygen saturation and peak to peak voltages of channels 1 and 2 are also shown on the exemplary display of FIG. 29.

The minimum peak to peak values (AC pulsatile component) of two channels and maximum CV of the H Values are configurable by the clinician as described above with respect to FIG. 14. If, the peak to peak values are below the minimum, then a REJECT message is displayed. Similarly, if the CV is greater than the user specified threshold, then the data set is rejected. Thus, when used together, the displayed CV, Peak to Peak measurements and the ACCEPT/REJECT message form a figure of merit measurement which can be used to assess the quality of the hematocrit prediction.

Figure 30A:
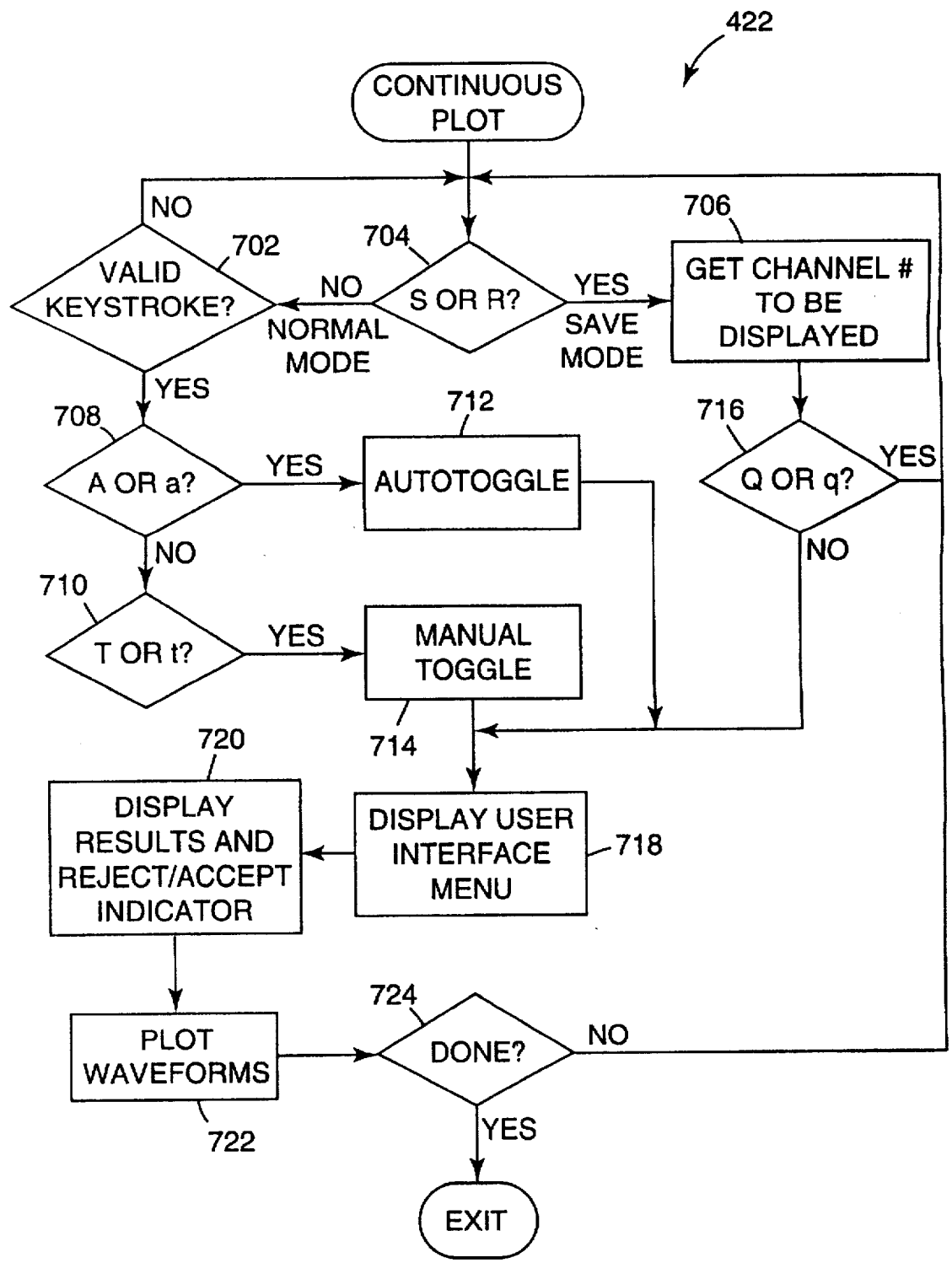
FIGS. 30A and 30B show control flow for continuous display of waveforms and interactive display, respectively.

FIG. 30A shows the process by which waveforms are displayed to the screen during continuous capture of photoplethysmographic data. There are two display modes, normal display mode and save mode.

When in normal display mode, a number of saving and displaying options are available through a combination of keystrokes. The user is allowed to change the actual channels that are displayed while sampling (due to screen size limitations, a maximum of five waveforms can be displayed at a time while sampling). The user can select "autotoggle", at blocks 709 and 172 during which the system will display different sets of channels on each loop through the procedure. For instance, if there are eight total channels after the first 512 samples for each channel are obtained, a group of channels including the designated peak channel, will be displayed. When the next complete sample is obtained, a group of four channels will be displayed. The second group of four channels will include the four channels which were not displayed the first time, and the designated peak channel. Preferably, the designated peak is always displayed for reference purposes.

The user can also manually toggle the display by pressing "T" or "t" at block 170 to toggle the channels to be displayed at block 714. Every time the user enters a "t" or "T", the next displayed channels will be the previous undisplayed channels. Manual toggling basically performs the same function as autotoggle except that the user indicates when the display should be toggled.

The procedure also constructs a basic menu of commands at block 718 the user can enter to manipulate both the screen output and actual saving of the captured data. This menu is displayed at block 720 on the screen as shown in FIG. 28.

Once one has entered "S" or "R" at block 704 to enter save mode, a different display is shown. In save mode, only two channels are displayed on the screen. The first channel is always the channel that was used to find the peaks and valleys. The second channel is user selectable at block 706. While in save mode the user can also enter a "Q" to quit saving at block 716.

Figure 30B:
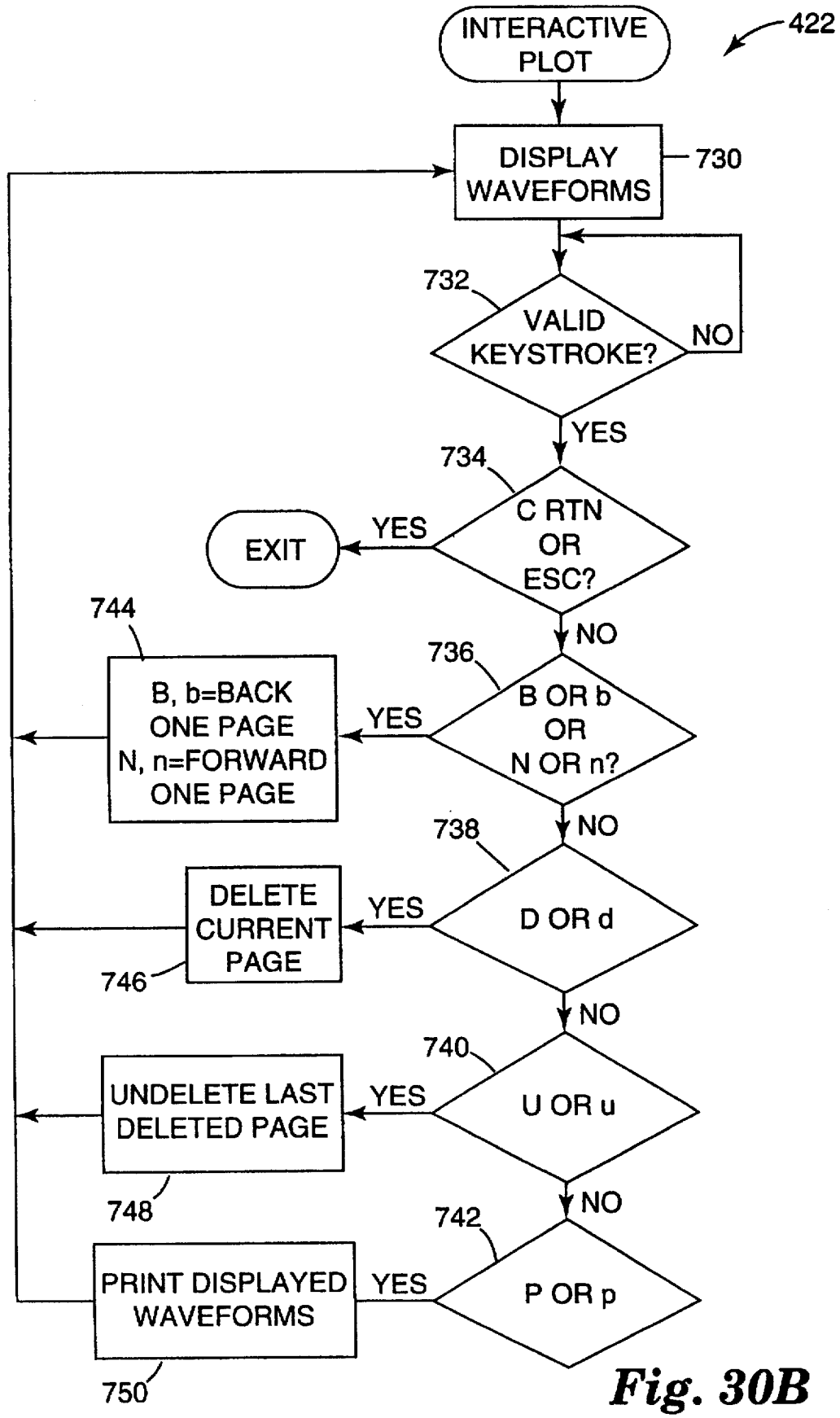

An actual plot at block 722 to the screen consists of one page of data or 512 data points in the preferred embodiment. However, a complete waveform will consist of many more stored data points. The procedure of FIG. 30B allows the user to interactively scroll back and forth through the file. The user can page backward through the waveform by pressing "B" or "b", or forward through the waveform by pressing "N" or "n" at block 736. The user is also able to print a waveform or waveforms at blocks 742 and 750 or interactively edit the waveforms by deleting pages (defined as 512 data points) from the plot at blocks 738 and 746. An undelete option is also available for those instances where pages are mistakenly deleted at blocks 740 and 748.

Prediction of Other Analytes of Interest

As mentioned previously, other analytes of interest in mammalian blood can be predicted using the method and apparatus of the present invention. The most common prediction conventionally employed is that of oxygen saturation. Because some of the eight wavelengths preferably employed can provide a ratio of wavelength absorbances at 660 nm and 910 nm, percent oxygen saturation can be readily predicted modifying to or adding electronic circuitry known to those skilled in the art. In that instance, a single apparatus can be used to predict both hematocrit and percent oxygen saturation, providing in a single noninvasive, transcutaneous device the ability to predict accurately and precisely two of the more important "blood gases" used in diagnosis or monitoring of the physiological conditions of mammalian patients.

Also as mentioned previously, one can combine a prediction of hematocrit with a prediction of methemoglobin to noninvasively monitor the physiological condition of mammalian blood stored for transfusion into mammalian patients.

In an alternative embodiment of the present invention, it was observed that stored blood ages in a manner that can be measured by the changes in hematocrit content and in methemoglobin. Specifically, it is an aspect of the present invention that the content of methemoglobin rises and hematrocrit also increases as stored blood ages. Those changes can be quantified according to the techniques of the invention as applied to a noninvasive interrogation of a storage bag of blood. In this embodiment, due to the desire for noncontact with the stored blood, the same considerations of noninvasiveness prediction apply. For example, the mean cell volume of a constant volume of blood stored at 4° C., as measured after equilibration at room temperature over an interval of two weeks increased from 86.9 cubic micrometers to 100.7 cubic micrometers.

Specifically, the quality of stored blood can be assessed by predicting changes in hematocrit and methemoglobin using the same wavelengths as described above for hematocrit and adding one or more or some combination of the wavelengths of about 420 nm, 540 nm, 580 nm, 630 nm, and 1224 nm; the individual wavelengths may represent peaks and valleys or the isosbestic point(s) of the absorption spectrum of methemoglobin (in its acid and base form) and the spectra of various forms of hemoglobin such as oxydeoxy-, carboxy-, and sulfhemoglobin, to predict methemoglobin. The use of the same statistical analysis can be employed, with a possible equation used as follows:

$$HCT = \alpha'HV_{n,y} + \beta'HV_{n1,y1} + \chi'HV_{n2,y2} + \delta'HV_{n3,y3} + \epsilon'HV_{n4,y4} + \phi$$

where the terms have the same meaning as in Equation 5 above but now in addition employ the above cited wavelengths for methemoglobin to form the HV ratios.

It is important in this embodiment when using the blood in the storage bag of blood to pulsate the blood in order to generate peaks and valleys for proper calculation. One method is to make two measurements, one at each of two different distances between the light source and light collecting fibers. The storage bag of blood is between the fibers.

The utility of this embodiment of the present invention can be vital to supply of mammalian blood to a patient in emergency conditions. Also inventories of stored blood can be analyzed for shelf life prior to use. Because methemoglobin affects human blood by increasing the fraction of the ferric form of iron over the ferrous form and thereby decreasing the ability of hemoglobin to combine with oxygen, this embodiment has significant physiological value to a health care practitioner.

Within the scope of this aspect of the invention, other wavelengths sensitive to absorption changes due to the changes in scattering as a result of the increased size (or volume) of red blood cells due to aging of the stored blood can also be measured.

Because of the variable nature of the human population, and their habit of ingesting tobacco for relaxation or recreation, and/or inhaling smoke involuntarily, other mathematical variations can be introduced in the prediction equations in order to compensate for the presence of carboxyhemoglobin. For example, one can add to a prediction equation a correcting variable corresponding to the value for carboxyhemoglobin as provided by a co-oximeter or add additional wavelengths. A representative equation follows:

$$HCT = \alpha''HV_{n,y} + \beta''HV_{n1,y1} + \chi''HV_{n2,y2} + \delta''HV_{n3,y3} + \epsilon''HV_{n4,y4} + \phi$$

where the terms have the same meaning as in Equation 13 above but now in addition employ wavelengths to include carboxyhemoglobin (between about 450 nm and 1000 nm and preferably between 480 nm and 650 nm) and to form the HV ratios.

As justification for this alternative embodiment, it was found that the smoking population had a carboxyhemoglobin content of between 1–10% of total hemoglobin, whereas the non-smoking population had a carboxyhemoglobin content of less than 1%–2%.

People exposed to smoke from fires, for example, may have elevated carboxyhemoglobin values of up to 15 to 30%.

Usefulness of the Invention

As stated previously, embodiments of the invention have great advantage in the ability to accurately and precisely predict hematocrit, methemoglobin, percent oxygen saturation in a noninvasive, nonintrusive manner.

Health care practitioners can employ the method and apparatus of the present invention to predict hematocrit and other optional analytes of interest within acceptable levels of prediction in substitution for more costly, more intrusive, more painful, and more dangerous conventional techniques.

Because of the truly noninvasive, painless method of the invention, a health care practitioner can continuously or periodically monitor hematocrit of a patient for changes or trends in physiological condition or can rapidly diagnose the immediate condition of a patient under severe trauma in a civilian or military situation.

The invention is not limited to embodiments described above. The following claims and their operative equivalents identify the scope of the invention.

What is claimed is:

1. An apparatus for the noninvasive prediction of hematocrit within mammalian tissue, comprising:

(a) a light source adapted to noninvasively interrogate the mammalian tissue with light of at least two wavelengths, wherein the at least two wavelengths are selected according to wavelength selection criteria, and wherein the wavelength selection criteria comprise:

(1) a wavelength where absorbance of water is at or near a measurable peak;

(2) at least one wavelength where absorbance of oxyhemoglobin and deoxyhemoglobin are predictable and represent total hemoglobin content;

(3) a wavelength where the absorbance of water greatly exceeds the absorbance of all forms of hemoglobin; and (4) a wavelength where the absorbance of all forms of hemoglobin greatly exceeds the absorbance of water;

wherein each of the wavelength selection criteria must be satisfied, wherein each selected wavelength can satisfy one or more than one of the wavelength selection criteria, and wherein at least one of the selected wavelengths is in the range 1150–2100 nm;

(b) at least one detector adapted to receive light of the selected wavelengths transmitted through the mammalian tissue, the detector further adapted to convert the transmitted light of each selected wavelength from optical signals into electrical signals; and (c) processing means, connected to receive the electrical signals from the detector, the processing means for:

determining the intensity of at least one peak, the intensity of at least one valley, and the intensity of at least one direct current value for the transmitted light of each selected wavelength;

determining at least one pseudo-absorption H Value for each selected wavelength, wherein each H Value is based on the intensities of the at least one peak, at least one valley, and the at least one direct current value; and determining a prediction equation for the noninvasive prediction of hematocrit, wherein the prediction equation is based on true hematocrit values and the pseudo-absorption H Values determined for each selected wavelength.

2. The apparatus of claim 1, wherein the processing means is further adapted for noninvasively predicting hematocrit using the prediction equation.

3. The apparatus of claim 2, further comprising:
   (a) means for calculating a coefficient of variation of the at least one H Value.

4. The apparatus according to claim 2, further comprising:
   (d) means for displaying the prediction of hematocrit.

5. The apparatus of claim 1, wherein the modulated light source maintains relative spectral intensity.

6. The apparatus according to claim 1, wherein the wavelength selection criteria further comprises:
   (5) a wavelength where the absorbance of oxyhemoglobin greatly exceeds the absorbance of deoxyhemoglobin; and
   (6) a wavelength where the absorbance of deoxyhemoglobin greatly exceeds the absorbance of oxyhemoglobin.

7. The apparatus according to claim 6, wherein the wavelength selection criteria further comprises:
   (7) at least one different wavelength from selection criteria (1) where the absorbance of water is at or near a measurable peak or shoulder and is subjected to differing interferences than selection criteria (1); and
   (8) a wavelength where the absorbance of water is in or near a valley between peaks and where the absorbance of hemoglobin is minimal.

8. The apparatus according to claim 7, wherein the wavelength selection criteria further comprises:
   (9) a wavelength where water and hemoglobin are in an isosbestic relationship.

9. The apparatus according to claim 8, wherein the wavelength selection criteria (1) has a range of about 1160–1230 nm; wherein the wavelength selection criteria (2) has a range of about 800–850 nm; wherein the wavelength selection criteria (3) has a range of about 1150–2100 nm; wherein the wavelength selection criteria (4) has a range of about 450–690 nm; wherein the wavelength selection criteria (5) has a range of about 650–690 nm; wherein the wavelength selection criteria (6) has a range of about 890–920 nm; wherein the wavelength selection criteria (7) has a range of about 960–990 nm; and wherein the wavelength selection criteria (8) has a range of about 1100–1120 nm.

10. The apparatus according to claim 1, further comprising a fresnel lens to shape the transmitted light of each selected wavelength.

11. The apparatus according to claim 1, further comprising
    a high common mode rejection amplifier for amplifying and filtering the transmitted light of each selected wavelength.

* * * * *

UNITED STATES PATENT AND TRADEMARK OFFICE
CERTIFICATE OF CORRECTION

PATENT NO. : 5,755,226
DATED : May 26, 1998
INVENTOR(S) : Hatim M. Carim, et al.

It is certified that error appears in the above-identified patent and that said Letters Patent is hereby corrected as shown below:

On the title page, item [75] Inventors: Add Dirk R. Smith, Ramsey, MN.

Signed and Sealed this

Eleventh Day of May, 1999

*Attest:*

Q. TODD DICKINSON

*Attesting Officer*     *Acting Commissioner of Patents and Trademarks*